United States Patent
Matsui

(10) Patent No.: US 9,006,256 B2
(45) Date of Patent: Apr. 14, 2015

(54) ANTITUMOR AGENT FOR THYROID CANCER

(75) Inventor: Junji Matsui, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 71 days.

(21) Appl. No.: 13/083,338

(22) Filed: Apr. 8, 2011

(65) Prior Publication Data

US 2011/0207756 A1 Aug. 25, 2011

Related U.S. Application Data

(62) Division of application No. 12/301,353, filed as application No. PCT/JP2007/060560 on May 17, 2007, now abandoned.

(60) Provisional application No. 60/747,570, filed on May 18, 2006.

(51) Int. Cl.

| | | |
|---|---|---|
| A01N 43/54 | (2006.01) | |
| A61K 31/517 | (2006.01) | |
| A01N 43/40 | (2006.01) | |
| A61K 31/47 | (2006.01) | |
| A01N 43/38 | (2006.01) | |
| A61K 31/405 | (2006.01) | |
| C12Q 1/68 | (2006.01) | |
| C07D 215/22 | (2006.01) | |

(52) U.S. Cl.
CPC .............. *C12Q 1/6886* (2013.01); *A61K 31/47* (2013.01); *C07D 215/22* (2013.01); *C12Q 2600/106* (2013.01)

(58) Field of Classification Search
USPC .................... 514/266.2, 312; 312/414
See application file for complete search history.

(56) References Cited

U.S. PATENT DOCUMENTS

| | | |
|---|---|---|
| 4,526,988 A | 7/1985 | Hertel et al. |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,445,934 A | 8/1995 | Fodor et al. |
| 5,464,826 A | 11/1995 | Grindey et al. |
| 5,487,889 A | 1/1996 | Eckert et al. |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |

(Continued)

FOREIGN PATENT DOCUMENTS

| | | |
|---|---|---|
| CN | 1473041 A | 2/2004 |
| CN | 1478078 | 2/2004 |

(Continued)

OTHER PUBLICATIONS

Carlomagno et al. (Cancer Research 62, 7284-7290, Dec. 15, 2002).*
Santoro et al. Ann. N.Y. Acad. Sci. 963: 116-121 (2002).*
Bernex et al. Development 122, 3023-3033 (1996).*
Boissan et al. (J. leucocyte biology ; 67, (2000); 135-148).*
Clinical Trials (2005).*
Polverino et al. Cancer Res 2006;66:8715-8721.*
Ko et al., 'Stomach Cancer', Cancer supportive care.com, published online Feb. 2003, pp. 1-4.
Kleespies et al., Tyrosine kinase inhibitors and gemcitabine: New treatment options in pancreatic cancer?, Drug Resistance Updates 9:1-19 (2006).
Okura et al., "Effects of monoclonal anti-c-kit antibody (ACK2) on melanocytes in newborn mice", J. Invest. Dermatol., 105(3): 322-328 (1995).

(Continued)

*Primary Examiner* — Shirley V Gembeh

(74) *Attorney, Agent, or Firm* — Fish & Richardson P.C.

(57) ABSTRACT

The present invention provides pharmaceutical compositions and therapeutic methods for treating diseases such as multiple endocrine neoplasia type IIA, multiple endocrine neoplasia type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract. The therapeutic methods and pharmaceutical compositions use a RET kinase inhibiting substance, such as 4-(3-chloro-4-(cyclopropylaminocarbonyl)aminophenoxy)-7-methoxy-6-quinolinecarboxamide and pharmacologically acceptable salts thereof, and involve a step of administering the RET kinase inhibiting substance to a patient.

6 Claims, 3 Drawing Sheets

(56) References Cited

U.S. PATENT DOCUMENTS

| | | |
|---|---|---|
| 7,253,286 B2 | 8/2007 | Funahashi et al. |
| 7,435,590 B2 | 10/2008 | Komurasaki |
| 7,485,658 B2 * | 2/2009 | Bolger et al. ............... 514/394 |
| 7,495,104 B2 | 2/2009 | Miwa et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,759,518 B2 | 7/2010 | Maderna et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0202541 A1 | 8/2009 | Bruns et al. |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0293615 A1 | 12/2011 | Yamamoto |
| 2012/0022076 A1 | 1/2012 | Maderna et al. |
| 2012/0077842 A1 | 3/2012 | Bando |
| 2012/0207753 A1 | 8/2012 | Yu et al. |
| 2012/0219522 A1 | 8/2012 | Xl |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CN | 1890220 A | 1/2007 |
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 0 297 580 | 1/1989 |
| EP | 0405425 | 1/1991 |
| EP | 0602851 | 6/1994 |
| EP | 0684820 | 6/1995 |
| EP | 0795556 | 9/1997 |
| EP | 0837063 | 4/1998 |
| EP | 0870842 | 10/1998 |
| EP | 930305 | 7/1999 |
| EP | 930310 | 7/1999 |
| EP | 1029853 | 8/2000 |
| EP | 1044969 | 10/2000 |
| EP | 543942 | 1/2001 |
| EP | 1153920 | 11/2001 |
| EP | 0712863 | 2/2002 |
| EP | 1331005 | 7/2003 |
| EP | 1382604 | 1/2004 |
| EP | 1411046 | 4/2004 |
| EP | 1415987 | 5/2004 |
| EP | 1447405 | 1/2005 |
| EP | 1506962 | 2/2005 |
| EP | 1 522 540 | 4/2005 |
| EP | 1 535 910 | 6/2005 |
| EP | 1552833 | 7/2005 |
| EP | 1566379 | 8/2005 |
| EP | 1604665 | 12/2005 |
| EP | 1683785 | 7/2006 |
| EP | 1698623 | 9/2006 |
| EP | 1797877 | 6/2007 |
| EP | 1797881 | 6/2007 |
| EP | 1859797 | 11/2007 |
| EP | 1894918 | 3/2008 |
| EP | 1925676 | 5/2008 |
| EP | 1925941 | 5/2008 |
| EP | 1949902 | 7/2008 |
| EP | 1964837 | 9/2008 |
| EP | 2116246 | 11/2009 |
| EP | 2119707 | 11/2009 |
| EP | 2133094 | 12/2009 |
| EP | 2133095 | 12/2009 |
| EP | 2218712 | 8/2010 |
| GB | 2253848 | 9/1992 |
| IN | 236500 | 11/2009 |
| JP | S63-028427 | 2/1988 |
| JP | 01-022874 | 1/1989 |

(56) References Cited

FOREIGN PATENT DOCUMENTS

| | | |
|---|---|---|
| JP | 02-291295 | 12/1990 |
| JP | 04-341454 | 11/1992 |
| JP | 06-153952 | 6/1994 |
| JP | 07-176103 | 7/1995 |
| JP | 08-045927 | 2/1996 |
| JP | 08-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 3/2000 |
| JP | 3088018 | 7/2000 |
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 3420549 | 4/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 3712393 | 8/2005 |
| JP | 2005-272474 | 10/2005 |
| JP | 2006-508981 | 3/2006 |
| JP | 2006-515884 | 6/2006 |
| KR | 10-0589032 | 6/2006 |
| WO | 86/03222 | 6/1986 |
| WO | WO 92/20642 | 11/1992 |
| WO | WO9409010 A1 | 4/1994 |
| WO | WO 95/15758 | 6/1995 |
| WO | WO 95/19774 | 7/1995 |
| WO | WO 96/09294 | 3/1996 |
| WO | WO 96/26997 | 9/1996 |
| WO | 96/30347 | 10/1996 |
| WO | 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | 97/17329 | 5/1997 |
| WO | WO 97/21437 | 6/1997 |
| WO | WO 97/38984 | 10/1997 |
| WO | 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | 98/14437 | 4/1998 |
| WO | WO 98/13350 | 4/1998 |
| WO | WO 98/23613 | 6/1998 |
| WO | WO 98/32436 | 7/1998 |
| WO | 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | 99/35146 | 7/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/43654 | 9/1999 |
| WO | 99/62890 | 12/1999 |
| WO | 00/31048 | 6/2000 |
| WO | 00/42012 | 7/2000 |
| WO | 00/43366 | 7/2000 |
| WO | WO 00/43384 | 7/2000 |
| WO | 00/47212 | 8/2000 |
| WO | WO 00/44728 | 8/2000 |
| WO | WO 00/50405 | 8/2000 |
| WO | WO 00/71097 | 11/2000 |
| WO | 01/02369 | 1/2001 |
| WO | 01/23375 | 4/2001 |
| WO | 01/27081 | 4/2001 |
| WO | 01/32926 | 5/2001 |
| WO | WO 01/36403 | 5/2001 |
| WO | 01/40217 | 6/2001 |
| WO | WO 01/45689 | 6/2001 |
| WO | 01/47890 | 7/2001 |
| WO | WO 01/47931 | 7/2001 |
| WO | 01/60814 | 8/2001 |
| WO | WO 02/16348 | 2/2002 |
| WO | 02/32872 | 4/2002 |
| WO | 02/36117 | 5/2002 |
| WO | 02/41882 | 5/2002 |
| WO | WO 02/44156 | 6/2002 |
| WO | 02/072578 | 9/2002 |
| WO | 02/080975 | 10/2002 |
| WO | 02/088110 | 11/2002 |
| WO | 02/092091 | 11/2002 |
| WO | 03/006462 | 1/2003 |
| WO | WO 03/013529 | 2/2003 |
| WO | WO 03/024386 | 3/2003 |
| WO | 03/027102 | 4/2003 |
| WO | 03/028711 | 4/2003 |
| WO | 03/033472 | 4/2003 |
| WO | 2003-033472 | 4/2003 |
| WO | 03/050090 | 6/2003 |
| WO | 03/074045 | 9/2003 |
| WO | 03/079020 | 9/2003 |
| WO | 2004/006862 | 1/2004 |
| WO | 2004/020434 | 3/2004 |
| WO | 2004/032872 | 4/2004 |
| WO | 2004/032937 | 4/2004 |
| WO | WO 2004/035052 | 4/2004 |
| WO | 2004/041308 | 5/2004 |
| WO | 2004/043472 | 5/2004 |
| WO | WO 2004/039782 | 5/2004 |
| WO | 2004045523 | 6/2004 |
| WO | WO 2004/064730 | 8/2004 |
| WO | 2004/078144 | 9/2004 |
| WO | 2004/080462 | 9/2004 |
| WO | WO 2004/080966 | 9/2004 |
| WO | 2004/101526 | 11/2004 |
| WO | 2005/004870 | 1/2005 |
| WO | 2005/021537 | 3/2005 |
| WO | 2005/027972 | 3/2005 |
| WO | 2005/030140 | 4/2005 |
| WO | 2005/044788 | 5/2005 |
| WO | 2005/051366 | 6/2005 |
| WO | 2005/056764 | 6/2005 |
| WO | 2005/063713 | 7/2005 |
| WO | 2005/082854 | 9/2005 |
| WO | 2005/092896 | 10/2005 |
| WO | 2005/117887 | 12/2005 |
| WO | 2006/030826 | 3/2006 |
| WO | 2006/030941 | 3/2006 |
| WO | 2006/030947 | 3/2006 |
| WO | 2006/062984 | 6/2006 |
| WO | 2006/090930 | 8/2006 |
| WO | 2006/090931 | 8/2006 |
| WO | 2006/036941 | 12/2006 |
| WO | 2006/137474 | 12/2006 |
| WO | 2007/000347 | 1/2007 |
| WO | 2007/014335 | 2/2007 |
| WO | 2007/015569 | 2/2007 |
| WO | 2007/015578 | 2/2007 |
| WO | 2007/023768 | 3/2007 |
| WO | 2007/040565 | 4/2007 |
| WO | 2007/052849 | 5/2007 |
| WO | 2007/052850 | 5/2007 |
| WO | 2007/061127 | 5/2007 |
| WO | 2007/061130 | 5/2007 |
| WO | 2007/136103 | 11/2007 |

(56) References Cited

FOREIGN PATENT DOCUMENTS

| WO | 2008/023698 | 2/2008 |
|---|---|---|
| WO | WO2008026748 A1 | 3/2008 |
| WO | 2008/088088 | 7/2008 |
| WO | 2008/093855 | 8/2008 |
| WO | 2009/060945 | 5/2009 |
| WO | 2009/077874 | 6/2009 |
| WO | 2009/096377 | 8/2009 |
| WO | WO2009140549 A1 | 11/2009 |
| WO | 2010/006225 | 1/2010 |
| WO | 2011/017583 | 2/2011 |
| WO | 2011/022335 | 2/2011 |

OTHER PUBLICATIONS

Final Office Action for U.S. Appl. No. 12/523,495 dated Dec. 27, 2011.
Final Office Action for U.S. Appl. No. 11/997,719 issued on Apr. 6, 2011.
Office Action for U.S. Appl. No. 13/205,325 dated Jan. 12, 2012.
Final Office Action for U.S. Appl. No. 11/997,543 dated Nov. 9, 2011.
Office Action for U.S. Appl. No. 12/524,754 dated Dec. 19, 2011.
Nishikawa et al., "Cys611Ser mutation in RET proto-oncogene in a kindred with medullary thryroid carcinoma and Hirschsprung's disease", European Journal of Human Genetics, 11, 364-368 (2003).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Carniti et al., "The RetC62OR Mutation Affects Renal and Enteric Development in a mouse Model of Hirschprung's Disease", American Journal of Pathology, 168, 1262-1275, (2006).
Asai et al., "Mechanism of Ret Activation by a Mutation of Aspartic Acid 631 Identified in Sporadic Pheochromocytoma", Biochemical and Biophysical Research Communications, 255, 587-590 (1999).
Carlomagno et al., "Point Mutation of the RET Proto-Oncogene in the TT Human Medullary Thyroid Carcinoma cell Line", Biochemical and Biophysical Research Communications, 207, 1022-1028 (1995).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Miyauchi et al., "Two Germline Missense Mutations of Codons 804 and 806 of the RET proto-oncogene in the Same Allele in a Patient with Multiple Endocrine Neoplasia Type 2B without Codon 915 Mutation", Japanese Journal of Cancer Research, 90, 1-5, (1999).
Joao et al., "Somatic trinucleotide change encompassing codons 882 and 883 of the RET proto-oncogene in a patient with sporadic medullary thyroid carcinoma", European Journal of Endocrinology, 142, 573-575, (2000).
Kim et al., "RET Oligonucleotide Microarray for the Detection of RET Mutations in Multiple Endocrine Neoplasia Type 2 Syndromes", Clinical Cancer Research, 8, 457-463, (2002).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Lam et al., "High prevalence of RET proto-oncogene activation (RET/PTC) in papillary thyroid carcinomas", Eur J Endocrinology, 147: 741-745 (2002).
Klugbauer et al., "Detection of a Novel Type of RET Rearrangement (PTC5) in Thyroid Carcinomas after Chernobyl and Analysis of the Involved RET-fused Gene RFG5", Cancer Research, 58: 198-203 (1998).
Klugbauer and Rabes, "The transcription coactivator HT1F1 and a related protein are fused to the RET receptor tyrosine kinase in childhood papillary thyroid carcinomas", Oncogene, 18: 4388-4393 (1999).
Salassidis et al., "Translocation t(10; 14) (q11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Nakata et al., "Fusion of a Novel Gene, ELKS, to RET Due to Translocation t(10; 12) (q11; p13) in a Papillary Thyroid Carcinoma", Genes Chromosomes Cancer, 25: 97-103 (1999).
Corvi et al., "RET/PCM-1: a novel fusion gene in papillary thyroid carcinoma", Oncogene, 19: 4236-4242 (2000).
Sanger et al., DNA sequencing with chain-terminating inhibitors, Proc. Natl. Acad. Sci. USA 74: 5463 (1977).
Sun et al., "Discovery of . . . Receptor Tyrosine Kinase", Journal of Medicinal Chemistry., 46: 1116-9 (2003).
Written Opinion of the International Searching Authority for PCT/JP2007/060560 mailed on Sep. 11, 2007 with English translation.
International Preliminary Report of Patentability issued for PCT/JP2007/060560 on Nov. 18, 2008 with English translation.
Australian Office Action directed at Appl. No. 2007252506 issued on Nov. 7, 2011.
Australian Response to Office Action directed at Appl. No. 2007252506 filed on Jan. 4, 2012.
Australian Office Action directed at Appl. No. 2007252506 issued on Jan. 13, 2012.
Chinese Office Action directed at Appl. No. 200780017371.9 mailed on Oct. 20, 2010 with English translation.
Chinese Response to Office Action directed at Appl. No. 200780017371.9 filed on Feb. 24, 2011 with English translation.
European Response to EESR directed at Appl. No. 07743994.1-2123 filed on Nov. 23, 2010.
Israel Office Action directed at Appl. No. 195282 issued on Jan. 26, 2010 with English translation.
Israel Response (IDS List) to Office Action directed at Appl. No. 195282 filed on May 3, 2010 with English translation.
Israel Appl. No. 195282 IDS List filed on Jul. 1, 2010.
Russian Office Action directed at Appl. No. 2008149948/15(065561) issued on May 24, 2011 with English translation.
Russian Response to Office Action directed at Appl. No. 2008149948/15(065561) filed on Jul. 27, 2011 with English translation.
Russian Decision of Grant directed at Appl. No. 2008149948/15(065561) with English translation.
US Office Action directed at U.S. Appl. No. 12/301,353 issued on Oct. 29, 2010.
US Response to Office Action directed at U.S. Appl. No. 12/301,353, filed Nov. 23, 2010.
Australian Response to Office Action directed at Appl. No. 2007252506 filed on Mar. 2, 2012.
Response to the OA issued for U.S. Appl. No. 11/997,543 filed on Mar. 22, 2011.
Response to the OA issued for U.S. Appl. No. 11/997,543 filed on Aug. 19, 2011.
Response to the OA issued for U.S. Appl. No. 11/997,543 filed on Jan. 9, 2012.
Response to the OA issued for U.S. Appl. No. 11/997,719 filed on Dec. 23, 2010.
Response to the Final OA issued for U.S. Appl. No. 11/997,719 filed on Jul. 6, 2011.
Response to Office Action issued for U.S. Appl. No. 12/092,539 filed on Nov. 22, 2010.
Response to Office Action issued for U.S. Appl. No. 12/092,539 filed on Mar. 11, 2011.
Response to Final Office Action issued for U.S. Appl. No. 12/092,539 filed on Jun. 15, 2011.
Response to OA issued for U.S. Appl. No. 13/205,328 filed on Apr. 11, 2012.
Response to Office Action directed at U.S. Appl. No. 12/301,353 filed on Nov. 23, 2010.
Response to the OA for U.S. Appl. No. 12/439,339 filed on Aug. 10, 2011.

(56) References Cited

OTHER PUBLICATIONS

Response to the OA for U.S. Appl. No. 12/439,339 filed on Feb. 7, 2012.
Response to the OA for U.S. Appl. No. 12/523,495 filed on Dec. 7, 2011.
Response to the OA for U.S. Appl. No. 12/524,754 filed on Dec. 1, 2011.
Response to the OA for U.S. Appl. No. 12/524,754 filed on Feb. 17, 2012.
Response to the OA for U.S. Appl. No. 12/864,817 filed on Aug. 9, 2011.
Response to the OA of U.S. Appl. No. 12/864,817 filed on Dec. 5, 2011.
Response to the OA for U.S. Appl. No. 12/864,817 filed on Dec. 22, 2011.
Response to Office Action for AU 2006309551 filed on Mar. 28, 2012.
CN Office Action issued for CN 200880002425.9 on Mar. 7, 2012.
AU Office Action issued for AU 2008211952 on Apr. 3, 2012.
CN Office Action directed at Appl. No. 200780017371.9 mailed on Mar. 7, 2012.
IL Office Action issued for IL 195282 on Feb. 5, 2012.
CN Office Action issued for CN 200880115011.7 on Feb. 20, 2012.
Response to IL OA directed at Appl. No. 205512 filed on Mar. 11, 2012.
Response to IL OA directed at Appl. No. 207089 filed on Mar. 11, 2012.
AU Office Action issued for AU 2008205847 on Apr. 11, 2012.
Office Action issued for U.S. Appl. No. 10/797,903 on Apr. 1, 2010.
Office Action issued for U.S. Appl. No. 10/797,903 on Sep. 1, 2010.
Office Action (Decision to refuse) issued for EP 04807580.8 on Oct. 25, 2011.
Forbes et al., "Dissolution kinetics and solubilities of p-aminosalicyclic acid and its salts", International Journal of Pharmaceutics, Elsevier Science BV, 126:199-208 (1995).
Ernst Mutschler et al., Arzneimittel-Wlrkungen Lehrbuch Der Pharmakologie Und Toxikologie, Wissenschaftliche Verlagsgesellschaft, Stuttgart, Jan. 1, 1999, p. 1-5.
Rudolf Voight et al., Pharmazeutische Technologie Fuer Studium Und Beruf,DT. Apotheker-Verl, Stuttgart; DE, Jan. 1, 2000, p. 40-52. XP008143620.
Lennartsson et al., "The Stem Cell Factor Receptor/c-Kit as a Drug Target in Cancer", Current Cancer Drug Targets, 6:561-571 (2006).
N. Turner and R. Grose, "Fibroblast growth factor signalling: form development to cancer", Nature Reviews, Cancer,10:116-129 (2010).
S. Wells and M. Santoro, "Targeting the RET Pathway in Thyroid Cancer", Clinical Cancer Research, 15:7119-7123 (2009).
Giuseppe Di Lorenzo et al., "Targeted Therapy in the Treatment of Metastatic Renal Cell Cancer", Oncology, 77 (Suppl.1):122-131 (2010).
Abby B.-Siegel et al., "Sorafenib: Where Do We Go from Here?" Hepatology, 52:360-369 (2010).
Kanai et al., "Development Status and Future Prospects of Novel Molecular Target Drugs for Hepatocellular Carcinoma", Journal of the Japanese Society of Gastroenterology, 106:1727-1735 (2009).
National Institutes of Health, Food and Drug Administration, National Library of Medicine, http://clinicaltrials.gov/ct2/show/study /NCT01136733, Sep. 27, 2010.
Office Action issued for EP application No. 04818213.3 on Feb. 2, 2012.
Kitteringham et al., "A Simple Method for the Synthesis of Unsymmetrical Ureas", Synthetic Communications, 30 (11):1937-1943 (2000).
Notice of Allowance issued for U.S. Appl. No. 12/986,638 on Mar. 22, 2012.
International Preliminary Examination Report and Patentability and Written Opinion for International Application No. PCT/2010/063804 dated Mar. 22, 2012.
Restriction Requirement issued for U.S. Appl. No. 11/997,543 dated Feb. 23, 2011.
Restriction Requirement issued for U.S. Appl. No. 12/092,539 dated Oct. 29, 2010.
Restriction Requirement issued for U.S. Appl. No. 12/301,353 dated Oct. 29, 2010.
Restriction Requirement issued for U.S. Appl. No. 12/439,339 dated Jul. 29, 2011.
Restriction Requirement issued for U.S. Appl. No. 12/524,754, filed Nov. 3, 2011.
Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology 18:317-323 (2007).
Asuno-Shinyaku, "The New Drugs of Tomorrow", Update Summary Dec. 2006 with English translation (14 pages).
Agarwal et al., "Binding of Discoidin Domain Receptor 2 to Collagen I: An Atomic Force Microscopy Investigation", Biochemistry 41:11091-11098 (2002).
Shimizu et al., "Orally active anti-proliferation agents: novel diphenylamine derivatives as FGF-R2 autophosphorylation inhibitors", Bioorganic & Medicinal Chem. Letters 14:875-879 (2004).
Plowright et al., "Ectopic expression of fibroblast growth factor receptor 3 promotes myeloma cell proliferation and prevents apoptosis" Neoplasia, Blood, 95(3): 992-998 (2000).
Heinrich et al., "Inhibition of c-kit receptor tyrosine kinase activity by STI 571, a selective tyrosine kinase inhibitor", Hematopoeisis, Blood 96(3):925-932 (2000).
Trudel et al., "Inhibition of fibroblast growth factor receptor 3 induces differentiation and apoptosis in t(4;14) myeloma", Neoplasia, Blood, 103(9): 3521-3528 (2004).
Trudel et al., "CHIR-258, a novel, multitargeted tyrosine kinase inhibitor for the potential treatment of t(4;14) multiple myeloma", Neoplasia, Blood 105(7):2941-2948 (2005).
Paterson et al., "Preclinical studies of fibroblast growth factor receptor 3 as a therapeutic target in multiple myeloma", Blackwell Publishing Ltd, British Journal of Haematology, 124: 595-603 (2004).
Wang et al., "Phase II study of gemcitabine and carboplatin in patients with advanced non-small-cell lung cancer", Cancer Chemother Pharmacol, 60:601-607 (2007).
Salmon et al., "Anti-Angiogenic Treatment of Gastrointestinal Malignancies", New Drugs, Cancer Investigation 23:712-726 (2005).
Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).
Itoh et al., "Preferential Alternative Splicing in Cancer Generates a K-sam Messenger RNA with Higher Transforming Activity", Cancer Research 54: 3237-3241(2002).
Ueda et al., "Deletion of the Carboxyl-Terminal Exons of K-sam/FGFR2 by Short omologymediated Recombination, Generating Preferential Expression of Specific Messenger RNAs", Cancer Research, 59:6080-6086 (1999).
Lin et al., "The Vascular Endothelias Growth Factor Receptor Tyrosine Kinase Inhibitor PTK787/ZK222584 Inhibits Growth and Migration of Mutiple Myeloma Cells in the Bone Marrow Microenvironment", Cancer Research, 62:5019-5026 (2002).
Lesueur et al., "Polymorphisms in RET and Its Coreceptors and Ligands as Genetic Modifiers of Multiple Endocrine Neoplasia Type 2A", Cancer Research 66(2):1177-1180 (2006).
Yanagihara et al., "Development and biological analysis of peritoneal metastasis mouse models for human scirrhous stomach cancer", Cancer Sci, 96(6):323-332 (2005).
Kim et al., "A Phase II Study of Irinotecan Plus Cisplatin for Patients With Advanced Stage IIIB or IV NSCLC Previously Treated With Nonplatinum-Based Chemotherapy", American Cancer Socieity, pp. 799-805 (2006).

(56) References Cited

OTHER PUBLICATIONS

Shiang et al., "Mutations in the Transmembrane Domain of FGFR3 Cause the Most Common Genetic Form of Dwarfism, Achondroplasia", Cell 78:335-342 (1994).
Vogel et al., "Sensing extracellular matrix: An update on discoidin domain receptor function", Cellular Signalling 18:1108-1116 (2006).
Hattori et al., "Immunohistochemical Detection of K-sam Protein in Stomach Cancer", Clinical Cancer Research, 2:1373-1381 (1996).
Zieger et al., "Role of Activating Fibroblast Growth Factor Receptor 3 Mutations in the Development of Bladder Tumors", Clin Cancer Res 11(21):7709-7719 (2005).
Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).
Santoro et al., "Minireview: RET: Normal and Abnormal Functions", Endocrinology 145(12):5448-5451 (2004).
Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).
Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamon, Oxford, GB XP004639590 abstract, 2006.
Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).
Haymo et al., "Pericytes in experimental MDA-MB231 tumor angiogenesis", Histochemistry and Cell Biology, 117(6):527-534 (2002).
Logie et al., "Activating mutations of the tyrosine kinase receptor FGFR3 are associated with benign skin tumors in mice and humans", Human Molecular Genetics, 14(9):1153-1160 (2005).
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).
Haller, D., "Chemotherapy for Advanced Pancreatic Cancer", Int. J. Radiation Oncology Biol. Phys., 56(4): Supplement, pp. 16-23 (2003).
Wakui , "Chemotherapy of scirrhous gastric cancer ", JP Journal of Cancer and Chemotherapy, 21(14): 2398-2406 (1994).
Takahashi et al., "A case of inoperable scirrhous gastric cancer that responded remarkably to a combination of TS-1 +paclitaxel and showed complete loss of ascites", JP Journal of Cancer and Chemotherapy, 31(7):1093-1095 (2004).
Werner et al., "Gastric adenocarcinoma: pathormorphology and molecular pathology", J. Cancer Res. Clin. Oncol. 127:207-216 (2001).
Jimenez et al., "Pheochromocytoma and Medullary Thyroid Carcinoma:A New Genotype-Phenotype Correlation of the *RET* Protooncogene 891 Germline Mutation", The Journal of Clinical Endocrinology & Metabolism 89(8):4142-4145 (2004).
Elisei et al., "Identification of a Novel Point Mutation in the RET Gene (Ala883Thr), Which Is Associated with Medullary Thyroid Carcinoma Phenotype Only in Homozygous Condition", The Journal of Clinical Endocrinology & Metabolism 89(11):5823-5827 (2004).
Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).
Johnson et al., "Paclitaxel Plus Carboplatin in Advanced Non-Small-Cell Lung Cancer: A Phase II Trial", Journal of Clinical Oncology 14(7):2054-2060 (1996).
Wozniak et al., "Randomized Trial Comparing Cisplatin With Cisplathn Plus Vinorelbine in the Treatment of Advanced Non-Small•Cell Lung. Cancer: A Southwest Oncology Group Study", Journal of Clinical Oncology 16(7):2459-2465 (1998).
Sandler et al., "Phase III Trial of Gemcitabine Plus Cisplatin Versus Cisplatin Alone in Patients With Locally Advanced or Metastatic Non-Small-Cell Lung Cancer", Journal of Clinical Oncology 18(1):122-130 (2000).
Gatzemeier et al., "Phase III Comparative Study of High-Dose Cisplatin Versus a Combination of Paclitaxel and Cisplatin in Patients With Advanced Non-Small-Cell Lung Cancer", Journal of Clinical Oncology 18(19):3390-3399 (2000).
Kelly et al., "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial", Journal of Clinical Oncology 19(13):3210-3218 (2001).
Heinrich et al., "Inhibition of KIT Tyrosine Kinase Activity: A Novel Molecular Approach to the Treatment of KIT-Positive Malignancies", Journal of Oncology 20(6):1692-1703 (2002).
Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).
Morgan et al., "Dynamic Contrast-Enhanced Magnetic Resonance Imaging As a Biomarker for the Pharmacological Response of PTK787/ZK 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).
McCulloch et al., "*Astragalus*-Based Chinese Herbs and Platinum-Based Chemotherapy for Advanced Non-Small-Cell Lung Cancer: Meta-Analysis of Randomized Trials", Journal of Clinical Oncology 24(3):419-430 (2006).
Mologni et al., "Inhibition of RET tyrosine kinase by SU5416", Journal of Mol. Endo., 37:199-212 (2006).
Carlomagno et al., "BAY 43/9006 Inhibition of Oncogenic RET Mutants", Journal of the National Cancer Institute 98(5):326-334 (2006).
Carlomagno et al., "ZD6474, an Orally Available Inhibitor of KDR Tyrosine Kinase Actvity, Efficiently Blocks Oncogenic RET Kinases", Cancer Research 62:7284-7290 (2002).
Tan et al., "Randomized study of vinorelbine-gemcitabine versus vinorelbine-carboplatin in patients with advanced non-small cell lung cancer", Lung Cancer, 49:233-240 (2005).
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).
Zhu et al., "Fibroblast growth factor receptor 3 inhibition by short hairpin RNAs leads to apoptosis in multiple myeloma", Mol Cancer Ther 4(5):787-798 (2005).
Santoro et al., "Drug Insight: small-molecule inhibitors of protein kinases in the treatment of thyroid cancer", Nature Clinical Practice Endocrinology & Metabolism 2(1):42-52 (2006).
Naski et al., "Graded activation of fibroblast growth factor receptor 3 by mutations causing achondroplasia and thanatophoric dysplasia", Nature Genetics 13:233-237 (1996).
Chesi et al., "Frequent translocation t(4;14)(p16.3;q32.3) in multiple myeloma is associated with increased expression and activating mutations of fibroblast growth factor receptor ", Nature Genetics, 3 16:260-264 (1997).
Capellen et al., "Frequent activating mutations of FGFR3 in human bladder and cervix carcinomas", Nature Genetics, 23:18-20 (1999).
Willett et al., "Direct evidence that the VEGF-specific antibody bevacizumab has antivascular effects in human rectal cancer", Nature Medicine 10(2):145-147 (2004).
Hurwitz et al., "Bevacizumab plus Irinotecan, Fluorouracil, and Leucovorin for Metastatic Colorectal Cancer", The New England Journal of Medicine, 350(23):2335-2342 (2004).
Miller et al., "Paclitaxel plus Bevacizumab versus Paclitaxel Alone for Metastatic Breast Cancer", The New England Journal of Medicine, 357:2666-76 (2007).

(56) References Cited

OTHER PUBLICATIONS

Jhiang, S., "The RET proto-oncogene in human cancers", Oncogene 19:5590-5597 (2000).
Chen et al., "FGFR3 as a therapeutic target of the small molecule inhibitor PKC412 in hematopoietic malignancies", Oncogene 24:8259-8267 (2005).
Experimental and Molecular Therapeutices 30, Proceedings of the American Association for Cancer Research, vol. 47 (2006).
Kashuk et al., "Phenotype-genotype correlation in Hirschsprung disease is illuminated by comparative analysis of the RET protein sequence", PNAS 102(25):8949-8954 (2005).
Morikawa et al., Angiogenesis and Pericytes, Putative Positive Function of Pericytes in Angiogenesis, Course of Cellular Biology, 13 pages, with English translation, (2005).
Benjamin et al., "Selective ablation of immature blood vessels in established human tumors follows vascular endothelial growth factor withdrawal", The J. of Clin. Invest. 103(2):159-165 (1999).
Olaso et al., "DDR2 receptor promotes MMP-2-mediated proliferation and invasion by hepatic stellate cells", The Journal of Clinical Investigation, 108( 9):1369-1378 (2001).
Bergers et al., "Benefits of targeting both pericytes and endothelial cells in the tumor vasculature with kinase inhibitors", The Journal of Clinical Investigation 111(9):1287-1295 (2003).
Inoue et al., "Molecular Target Therapy Targeting Angiogenesis Pathways", The Nishinihon J. Urol., 66:425-432 (2004).
Giles, F., "The Vascular Endothelial Growth Factor (VEGF) Signaling Pathway: A Therapeutic Target in Patients with Hematologic Malignancies", The Oncologists 6(supp15):32-39 (2001).
Hannequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).
Micke et al., "Characterization of c-kit expression in small cell lung cancer: prognostic and therapeutic implications", Clinical Cancer Res. 9:188-194(2003).
Office Action dated Oct. 30, 2009 for EP Appl. No. 04719054.1.
European Search Report for EP Appl. No. 06782407, Jul. 23, 2010.
ISR (PCT/JP2006/315563) dated Sep. 5, 2006.
ISR (PCT/JP2006/315698) dated Oct. 17, 2006.
ISR (PCT/JP2006/322514) dated Jan. 23, 2007.
ISR (PCT/JP2006/323881) dated Jan. 23, 2007.
ISR (PCT/JP2007/060560) dated Sep. 11, 2007.
ISR (PCT/JP2007/063525) dated Sep. 4, 2007.
ISR (PCT/JP2007/067088) dated Nov. 20, 2007.
ISR (PCT/JP2008/051024) dated Apr. 1, 2008.
ISR (PCT/JP2008/051697) dated Mar. 4, 2008.
ISR (PCT/JP2008/070321) dated Jan. 20, 2009.
ISR (PCT/JP2009/051244) dated Mar. 24, 2009.
Wang and Schwabacher, "A Convenient Set of Bidentate Pyridine Ligands for Combinatorial Synthesis", Tetrahedron Lett.40, 1999, p. 4779-p. 4782.
Taguchi et al., "A novel orally active inhibitor of VEGF rector tyrosine kinases KRN951: Anti-angiogenic and anti-tumor activity against human solid tumors.", Proceedings of the AACR annual meeting., vol. 45, Mar. 2004, p. 595, XP002536608.
Lev et al., "A Specific Combination of Substrates is Involved in Signal Transduction by the Kit-Encoded Rector", The EMBO Journa1,10(3), 1991, p. 647-p. 654.
Li et al., "Abrogation of c-kit/Steel factor-dendent tumorigenesis by kinase defective mutants of the c-kit rector: c-kit kinase defective mutants as candidate tools for cancer gene therapy, Cancer Research vol. 56", Oct. 1, 1996, p. 4343-p. 4346, XP002522473.
Gall-Istok, et al., "Abstract of Acta Chimica Hungarica", Inst. Exp. Med., Hung. Avad. Svi., Budapest, 1983, p. 112(2)-p. 241-7.
Tian, et al., "Activating c-kit Gene Mutations in Human Germ Cell Tumors", American Journal of Pathology, 154(6), 1999, p. 1643-p. 1647.
Okayama, et al., "Activation of Eosinophils with Cytokines Produced by Lung Mast Cells", Int Arch Allergy Immuno1.114:(suppl 1), 1997, p. 75-p. 77.

Blume-Jensen, et al., "Activation of the Human c-kit Product by Ligand-Induced Dimerization Mediates Circular Actin Reorganization and Chemotaxis", The EMBO Journal, 10(13), 1991, p. 4121-p. 4128.
Miyazaki et al., Synthesis, Structure and Biological Activity Relationship of . . . PDGF Receptor, AIMECS 03, 5th AFMC International Medicinal Chem. Symposium, Oct. 2003, Kyoto Japan, 1 page.
Longley, et al., "Altered Metabolism of Mast-Cell Growth Factor (c-kit Ligand) in Cutaneous Mastocytosis", The New England Journal of Medicine, 328(18), 1993, p. 1302-p. 1307.
Hayek, et al., "An In Vivo Model for Study of the Angiogenic Effects of Basic Fibroblast Growth Factor", Biochemical and Biophysical Research Communications, 147(2), 1987, p. 876-p. 880.
Folkman, et al., "Angiogenesis", The Journal of Biological Chemistry, 267(16), 1992, p. 10931-p. 10934.
Gerald B. Dermer, "Another anniversary for the war on cancer", Bio/Technology, vol. 12, 1994, p. 320.
Deplanque, et al., "Anti-Angiogenic Agents: Clinical Trial Design and Therapies in Development", European Journal of Cancer, 36, 2000, p. 1713-p. 1724.
Wedge et al., "AZD2171: A Highly Potent, Orally Bio available, Vascular Endothelial Growth Factor Rector-2 Tyrosine Kinase Inhibitor for the Treatment of Cancer", Cancer Res., vol. 65(10), p. 4389-4400, 2005.
Natali, et al., "Breast Cancer is Associated with Loss of the c-kit Oncogene Product", Int. J. Cancer, 52, 1992, p. 713-p. 717.
Trisha Gura, "Cancer Models Systems for Identifying new drugs are often faulty", Science, vol. 278, Nov. 7, 1997, p. 1041-p. 1042.
Wakeling, et al., ZD1839 (Iressa): An Orally Active Inhibitor of Epidermal Growth Factor Signalling with Potential for Cancer Therapy, Cancer Res.,62:5749-5754 ( 2002).
Ikeda, et al., "Changes in Phenotype and Proliferative Potential of Human Acute Myeloblastic Leukemia Cells in Culture with Stem Cell Factor", Experimental Hematology, 21, 1993, p. 1686-p. 1694.
J. Haleblian, Characterization of Habits and Crystalline Modification of Solids and Their Pharmaceutical Applications", Journal of Pharmaceutical Sciences", 64(8):1269-1288 (1975).
Metcalfe, D., "Classification and Diagnosis of Mastocytosis: Current Status", J. Invest. Dermatol, 96, 1991, p. 2S-p. 4S.
Folkman, et al., "Clinical Applications of Research on Angiogenesis", The New England Journal of Medicine, 333(26), 1995, p. 1757-p. 1763.
Hines, et al., "Coexpression of the c-kit and Stem Cell Factor Genes in Breast Carcinomas", Cell Growth & Differentiation, 6, 1995, p. 769-p. 779.
Hibi, et al., "Coexpression of the Stem Cell Factor and the c-kit Genes in Small-Cell Lung Cancer", Oncogene, 6, 1991, p. 2291-p. 2296.
R. Ian Freshney, Alan R. Liss, "Culture of Animal Cells, A Manual of Basic Technique", New York, 1983, p. 4.
Jakeman, et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2), 1993, p. 848-p. 859.
Matsui et al., "E7080 (ER-203492-00), a Novel VEGF Rector Tyrosine Kinase Inhibitor-I. Characterization as an Angiogenesis Inhibitor.", Abstract # 51, AACR, Toronto, Canada, Apr. 5-9, 2003.
Nakamura et al., "E7080 (ER-203492-00), a Novel VEGF Rector Tyrosine Kinase Inhibitor-II. Effects on Growth of Human Tumor Xenografts and Life Span of Mice in Colon 38 Orthotopic Transplantation Model." Abstract # 52, AACR, Toronto, Canada, Apr. 5-9, 2003.
Yamamoto et al., "A Novel VEGF Receptor Tyrosine Kinase Inhibitor-III. Significant prolongation of life span in mice transplanted with human ovarian carcinoma based on inhibition of VEGF signaling", Abstract # 50, AACR, Toronto, Canada, Apr. 5-9, 2003.
Yamamoto et al., "E7080 a novel multitargeted tyrosine kinase inhibitor, has direct anti-tumor activity via inhibition of KIT signaling in small cell lung cancer", Yamamoto et al., Abstract #4636, AACR, Orlando, FL, Mar. 27-31, 2004.
Matsui et al., "E7080, a novel inhibitor that targets multiple kinases, has potent antitumor activities against stem cell factor producing human small cell lung cancer H146, based on angionenesis inhibition", Int. J. Cancer 122:664-671 (2008).

(56) References Cited

OTHER PUBLICATIONS

Matsui et al., "E7080, a novel multi-rector Tyrosine Kinase Inhibitor, inhibited in vitro / in vivo VEGF- and SCF-driven angiogenesis SCLC cell line", Abstract #146, EORTC-NCI-AACR, Geneva, Switzerland, Sep. 28-Oct. 1, 2004.
Yamamoto et al., "E7080, an oral multi-targeted tyrosine kinase inhibitor, has direct anti-tumor efficacy via inhibition of KIT signaling in gastrointestinal stromal tumor (GIST)" Abstract #40358, 97th annual meeting AACR, Washington, DC., Apr. 1-5, 2006.
Taniguchi, et al., "Effect of c-kit Mutation on Prognosis of Gastrointestinal Stromal Tumors", Cancer Research, 59, 1999, p. 4297-p. 4300.
Nagata, et al., "Elevated Expression of the Proto-Oncogene c-kit in Patients with Mastocytosis", Leukemia, 12, 1998, p. 175-p. 181.
Kay, et al., "Eosinophils and Eosinophil-Associated Cytokines in Allergic Inflammation", Int. Arch. Allergy Immunol. 113, 1997, p. 196-p. 199.
Ikeda, et al., "Expression and Functional Role of the Proto-Oncogene c-kit in Acute Myeloblastic Leukemia Cells", Blood, 78(11), 1991, p. 2962-p. 2968.
Karl Nocka, et al., "Expression of c-kit gene products in known cellular targets of W mutations in normal and W mutant mice-evidence for an impaired c-kit kinase mutant mice", Genes & Development, Cold Spring Harbor Laboratory Press, 3:816-826, (1989).
Cohen, et al., "Expression of Stem Cell Factor and c-kit in Human Neuroblastoma", Blood, 84(10):3465-3472 (1994).
Strohmeyer, et al., "Expression of the hst-1 and c-kit Protoonocogenes in Human Testicular Germ Cell Tumors", Cancer Research, 51, 1991, p. 1811-p. 1816.
Kanakura, et al., "Expression, Function and Activation of the Proto-Oncogene c-kit Product in Human Leukemia Cells", Leukemia and Lymphorma, 10, 1993, p. 35-p. 41.
Bellone, et al., "Growh Stimulation of Colorectal Carcinoma Cells via the c-kit Rector is Inhibited by TGF-β-1", Journal of Cellular Physiology,172, 1997, p. 1-p. 11.
Okayama, et al., "Human Lung Mast Cells are Enriched in the Capacity to Produce Granulocyte-Macrophage Colony-Stimulating Factor in Response to IgE-Dendent Stimulation", Eur. J. Immunol 28, 1998, p. 708-p. 715.
Furitsu, et al., "Identification of Mutations in the Coding Sequence of the Proto-Oncogene c-kit in a Human Mast Cell Leukemia Cell Line Causing Ligand-Indendent Activation of c-kit Product", J. Clin. Invest. 92, 1993, p. 1736-p. 1744.
Croom, et al., "Imatinib mesylate in the Treatment of Gastrointestinal Stromal Tumours", Drugs, 63(5), 2003, p. 513-p. 522.
Mendel et al., "In Vivo Antitumor Activity of SU11248, a Novel Tyrosine Kinase Inhibitor Targeting Vascular Endothelial Growth Factor and Platelet-derived Growth Factor Rectors: Determination of a Pharmacokinetic/Pharmacodynamic Relationship" Clin. Cancer Res., 9: 327-337, (2003).
Spacey, et al., "Indolocarbazoles, Potent and Selective Inhibitors of Platelet-Derived Growth Factor Rector Autophosphorylation", Biochemical Pharmacology, 55:261-271, (1998).
Ciardiello, et al., "ZD1839 (IRESSA), An EGFR-Selective Tyrosine Kinase Inhibitor, Enhances Taxane Activity in BCL-2 Overexpressing, Multidrug Resistant MCF-7 ADR Human Breast Cancer Cells", Int. J. Cancer, 98:463-469, (2002).
Naruse, et al., "Antitumor Activity of the Selective Epidermal Growth Factor Receptor-Tyrosine Kinase Inhibitor (EGFR-TKI) IRESSA . . . In Vivo", Int. J. Cancer, 98:310-315, (2002).
International Search Report issued for related PCT application PCT/JP01/09221, Jan. 15, 2002.
International Search Report issued for related PCT application PCT/JP2004/003087, Jul. 13. 2004.
Boissan, et al., "c-Kit and c-kit mutations in mastocytosis and other hematological diseaseas", J. Leukocyte Biol., 67:135-148, (2000).
Nugiel et al., "Synthesis and Evaluation of Indenopyrazoles as Cyclin-Dependent Kinase Inhibitors. 2. Probing the Indeno Ring Substituent Pattern", Journal of Medical Chemistry, 45(24):5224-5232, (2002).
Tonary, et al., "Lack of Expression of c-KIT in Ovarian Cancers is Associated with Poor Prognosis", Int. J. Cancer (Pred. Oncol) 89, 2000, p. 242-p. 250.
Longley, et al., "Classes of c-Kit activating mutations: proposed mechanisms of action and implications for disease classification and therapy", Leukemia Res., 25:571-576, (2001).
Metcalf, et al., "Lineage Commitment in the Progeny of Murine Hematopoietic Prrogenitor Cells: Influence of Thrombopoietin and Interleukin 5", Proc. Nat'l Acad. Sci. USA, 95, 1998, p. 6408-p. 6412.
Metcalfe, et al., "Mast Cells", Physiological Reviews, 77(4), 1997, p. 1033-p. 1079.
Golkar, et al., "Mastocytosis", Lancet, 349, 1997, p. 1379-p. 1385.
Lasota, et al., "Mutations in Exons 9 and 13 of KIT Gene Are Rare Events in Gastrointestinal Stromal Tumors", American Journal of Pathology, 157(4), 2000, p. 1091-p. 1095.
"NCBI GenBank Accession No. NM_000222", Feb. 11, 2008.
Cairns et al., "New antiallergic pyrano[3,2g]quinoline-2,8-dicarboxylic acids with potential for the topical treatment of asthma", Cairns et al, Journal of Medicinal Chemistry 8(12), 1985, p. 1832-p. 1842.
Folkman, J., "New Perspective in Clinical Oncology From Angiogenesis Research", Eur J. Cancer. 32A(14), 1996, p. 2534-p. 2539.
Hogaboam, et al."Novel Role of Transmembrane SCF for Mast Cell Activation and Eotaxin Production in Mast Cell-Fibroblast Interactions", The Journal of Immunology, 160, 1998, p. 6166-p. 6171.
Gardner et al., "In Vitro Activity of Sorghum-Selective Fluorophenyl Urea Herbicides", Pesticide Biochemistry and Physiology, 24(3):285-297, (1985).
Sekido, et al., "Preferential Expression of c-kit Protooncogene Transcripts in Small Cell Lung Cancer", Cancer Research, 51, 1991, p. 2416-p. 2418.
"Proceedings of the American Association for Cancer Research", vol. 45, Mar. 2004, p. 1070-p. 1071.
Kolibaba, et al., "Protein Tyrosine Kinases and Cancer", Biochimica et Biophysica Acta, 1333, 1997, p. F217-p. F248.
Matsui et al., "Quantitative analysis of the profile of tumor vessels may be useful as predictive biomarkers for E7080", Abstract #4631, 98th AACR annual meeting, Los Angeles, CA,, Apr. 14-18, 2007.
Berdel, et al, "Recombinant Human Stem Cell Factor Stimulates Growth of a Human Glioblastoma Cell Line Expressing c-kit Protooncogene", Cancer Research, 52, 1992, p. 3498-p. 3502.
"Redefining the Frontiers of Science 94th Annual Meeting", American Association for Cancer Research, 2003, vol. 44, Washington D.C., USA, Jul. 11-14, 2003.
Kitamura, et al., "Regulation of Development, Survival and Neoplastic Growth of Mast Cells through the c-kit Rector", Int Arch Allergy Immunol , 107, 1995, p. 54-p. 56.
Naclerio, et al., "Rhinitis and Inhalant Allergens", JAMA, 278(22), 1997, p. 1842-p. 1848.
Bussolino, et al, "Role of Soluble Mediators in Angiogenesis", Eur. J. Cancer, 32A(14): , 1996, p. 2401-p. 2412.
Clark et al., "Safety and Pharmacokinetics of the Dual Action Raf Kinase and Vascular Endothelial Growth Factor Rector Inhibitor, BAY43-9006, in Patients with Advanced Refractory Solid Tumors", Clin. Cancer Res. (2005)11:, 2005, p. 5472-p. 5480.
Longley, et al., "Somatic c-KIT Activating Mutation in Urticaria Pigmentosa and Aggressive Mastocytosis: Establishment of Clonality in a Human Mast Cell Neoplasm", Nature Genetics, 12, 1996, p. 312-p. 314.
Furitsu et al., "Stable medicinal compositions of quinolinecarboxamide derivative", Database Caplus Chemical Abstracts Service, Columbus, Ohio, US, 2006, XP002520305.
Lukacs, et al., "Stem Cell Factor (c-kit Ligand) Influences Eosinophil Recruitment and Histamine Levels in Allergic Airway Inflammation", The Journal of Immunology, 156, 1996, p. 3945-p. 3951.
Kotva, et al., "Substances with Antineoplastic Activity, LIII. N-(δ-(4-Pyrrolo[2,3-d]Pyrimidinylthio) Valery] } Amino Acids and Analogous Derivatives of Di-and Triglycine", Collection Czechoslov. Chem. Commun 38, 1973, p. 1438-p. 1444.

(56) References Cited

OTHER PUBLICATIONS

Abuzar, S. et al., "Synthesis of some new 7-chloro-4-substituted quinolines as potential antiparasitic agents", Eur. J. Med. Chem.,vol. 21,No. 1, 1986, p. 5-p. 8.
Miyazaki et al., "Synthesis, Structure and Biological Activity Relationship of E7080 and its Derivatives as Novel and Potent Antiangiogenic Protein Tyrosine Kinase Inhibitors Including the VEGF Rectors, FGFR1 Rector and PDGF Rector." Abstract B-15, AIMECS03, Kyoto, Japan, Oct. 14-17, 2003.
Thomas et al., "The Eosinophil and its Role in Asthma", Gen. Pharmac. 27(4), 1996, p. 593-p. 597.
Wang, et al., "The Expression of the Proto-Oncogene C-Kit in the Blast Cells of Acute Myeloblastic Leukemia", Leukemia, 3(10), 1989, p. 699-p. 702.
Meltzer, E.O., "The Pharmacological Basis for the Treatment of Perennial Allergic Rhinitis and Non-Allergic Rhinitis with Topical Corticosteroids", Allergy, 52, 1997, p. 33-p. 40.
Myers, et al., "The Praration and SAR of 4-(Anilino), 4-(Phenoxy), and 4-(Thiophenoxy)-Quinazolines: Inhibitors of p561ck and EGF-R Tyrosine Kinase Activity", Bioorgan. & Med. Chem. Letters, 7, 1997, p. 417-p. 420.
Hamel, et al., "The Road Less Travelled: c-kit and Stem Cell Factor", Journal of Neuro-Oncology, 35, 1997, p. 327-p. 333.
Takano et al., "Thermal recording materials with improved background stability", Database CA(Online) Chemical Abstracts Service, Columbus, Ohio, US, Feb. 20, 1996, XP002443195.
Scheijen et al."Tryosine Kinase Oncogenes in Normal Hematopoiesis and Hematological Disease", Oncogene, 21, 2002, p. 3314-p. 3333.
"Types of Lung Cancer", Cancer care, Inc., Cancer care, Inc., Aug. 13, 2009.
Matsui et al., "VEGFRs inhibitor E7080 inhibits lymph node metastasis of human breast carcinoma, by preventing murine lymphatic endothelial cells from lymphangiogenesis.", Abstract # PD12-8, 18th EORTC-NCI-AACR symposium on "Molecular Targets and Cancer Therapeutics", Prague, Czech rublic, Nov. 7-10, 2006.
Folkman, J., "What is the Evidence That Tumors are Angiogenesis Dendent?", Journal of the National Cancer Institute, 82(1), 1990, p. 4-p. 6.
Takeda et al., "AZD2171 shows potent anti-tumor activity against gastric cancer expressing variant K-SAM/FGFR2", Proceeding of the American Association for Cancer Research, 47:890 (2006) #3785.
CN Office Action directed at application No. 200580026468.7 issued on Jun. 26, 2009, 6 pages.
CN Office Action directed at application No. 200710007097.9 issued on Mar. 6, 2009, 5 pages.
EESR directed at application No. 06832529.9 issued on Jul. 29, 2009, 6 pages.
Office Action directed at application No. 4025700.8 issued on Apr. 10, 2006, 3 pages.
Search Report directed at application No. 4719054.1 issued on Apr. 17, 2009, 4 pages.
Search Report directed at application No. 4818213.3 issued on Jul. 30, 2007, 3 pages.
JP Allowance directed at application No. P2005-515330 issued on Apr. 21, 2009, 2 pages.
KR Office Action directed at application No. 10-2006-7013993 issued on Jul. 31, 2007 (with English translation), 9 pages.
US Office Action directed at U.S. Appl. No. 10/577,531 issued on Sep. 23, 2008, 17 pages.
US Office Action directed at U.S. Appl. No. 10/797,903 issued on Aug. 20, 2009, 12 pages.
US Office Action directed at U.S. Appl. No. 10/797,903 issued on Dec. 11, 2007, 12 pages.
US Office Action directed at U.S. Appl. No. 11/347,749 issued on Feb. 9, 2009, 6 pages.
US Office Action directed at U.S. Appl. No. 11/997,719 issued on Sep. 3, 2010, 10 pages.
WO IPRP directed at application No. PCT/JP2004/003087 issued on Feb. 23, 2006, 5 pages.
WO IPRP directed at application No. PCT/JP2006/312487 issued on Jan. 10, 2008, 7 pages.
Anderson et al., "Preparation of Water-soluble Compounds through Salt Formation", The Practice of Medicinal Chemistry, Technomics, pp. 347-349, 355-356 (1999).
Japanese Office Action for Application No. 2005-516605, Jun. 1, 2010 (with partial translation).
Traxler et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity", Cancer Research 64:4931-4941 (2004).
European Search Report for Application No. 06768437.3 dated Oct. 11, 2010 (10 pages).
Vippagunta et al., "Crystalline solids", Advanced Drug Delivery Reviews 48:3-26 (2001).
Juurikivi et al., "Inhibition of c-kit tyrosine kinase by imatinib mesylate induces apoptosis in mast cells in rheumatoid synovia: a potential approach to the treatment of arthritis", Ann. Rheum. Dis., 64:1126-1131 (2005).
US Office Action directed at U.S. Appl. No. 12/092,539 issued on Jan. 7, 2011, 74 pages.
European Search Report for Application No. 06833681.7 dated Nov. 24, 2010.
US Office Action directed at U.S. Appl. No. 12/301,353 issued on Jan. 24, 2011.
Zhang et al., "Overexpression of Platelet-Derived Growth Factor Receptor $\alpha$ in Endothelial Cells of Hepatocellular Carcinoma Associated with High Metastatic Potential", Clinical Cancer Research 11:8557-8563 (2005).
European Search Report for Appln No. 07806561.2 dated Jan. 19, 2011.
Anonymous, Scientific Discussion, Internet Citation, Jan. 1, 2004, p. 1/61-p. 61/61, XP007918143.
Bastin et al., "Salt Selection and Optimisation for Pharmaceutical New Chemical Entities," Organic Process Research and Development, Cambridge, GB, vol. 4, No. 5, Jan. 1, 2000, p. 427-p. 435, XP002228592.
Berge et al., Journal of Pharmaceutical Sciences, American Pharmaceutical Association, Washington, US, vol. 66, No. 1, Jan. 1, 1977, p. 1-p. 19, XP002550655.
Gould et al., International Journal of Pharmaceutics, Elsevier, BV, NL, vol. 33, No. 1-3, Nov. 1, 1986, p. 201-p. 217, XP025813036.
Morris et al., "An integrated approach to the selection of optimal salt form for a new drug candidate," International Journal of Pharmaceutics, Elsevier, BV, NL, vol. 105, No. 3, May 9, 1994, p. 209-p. 217, XP023724810.
Ocqueteau et al., "Expression of the CD117 Antigen (C-Kit) on Normal and Myelomatous Plasma cells", British Journal of Haematology, 95:489-493 (1996).
Paz and Zhu, "Development of Angiogenesis Inhibitors to Vascular Endothelial Growth Factor Receptor 2. Current Status and Future Perspectiv", Frontiers in Bioscience 10:1415-1439 (2005).
Pritzker, "Cancer Biomarkers: Easier Said Than Done", Clinical Chemistry 48(8):1147-1150 (2002).
Raimondo et al., "Angiogenic factors in multiple myeloma: higher levels in bone marrow than in peripheral blood", Haematologica, 85:800-805 (2000).
Tong et al., "Vascular Normalization by Vascular Endothelial Growth Factor Receptor 2 Blockade Induces a Pressure Gradient Across the Vasculature and Improves Drug Penetration in Tumors", Cancer Research 64:3731-3736 (2004).
US Office Action directed at U.S. Appl. No. 11/997,543 issued May 19, 2011.
US Office Action directed at U.S. Appl. No. 12/094,492 issued on Mar. 24, 2011.
US Office Action directed at U.S. Appl. No. 12/864,817 issued on May 19, 2011.
Zhu et al., Molecular Targets for Therapy (MTT), "Inhibition of human leukemia in an animal . . . activity", Leukemia 17:604-611 (2003).

(56) References Cited

OTHER PUBLICATIONS

Chesi et al., "Activated fibroblast growth factor receptor 3 is an oncogene that contributes to tumor progression in multiple myeloma", Blood 97(3):729-736 (2001).
Search report directed at EP application No. 03791389.4, issued on Jul. 7, 2011, 3 pages.
European Search Report for Application No. 04807580.8 dated Apr. 18, 2011 (9 pages).
European Search Report for Application No. 06767145.3 dated May 23, 2011 (7 pages).
Yu, Lian, "Amorphous pharmaceutical solids: preparation, characterization and stabilization", Adv. Drug Delivery Reviews, Elsevier, Amsterdam, NL, 48(1):27-42 (2001).
Chinese Office Action directed at application No. 200880003336.6, issued on May 24, 2011, pages (with English Translation).
European Search Report for Application No. 10015141.4 dated Sep. 9, 2011.
US Office Action directed a U.S. Appl. No. 12/523,495 issued on Sep. 30, 2011.
US Office Action directed at U.S. Appl. No. 12/439,339 issued Nov. 14, 2011.
Zhou et al., "Correlation Research on VEGF Testing in Primary Gastric Cancer and Clinical Pathology Factor", Journal of Practical Oncology, 20(2):103-105 (2006) with English translation.
Response to Chinese Office Action filed for CN 200880115011.7 dated Jul. 5, 2012, with English translation.
Japanese Office Action for JP2009-123432 dated Sep. 4, 2012, with English translation.
Response to Chinese Office Action for CN 200680020317.5 dated Sep. 11, 2012, with English translation.
Official Letter for CA Patent Application No. 2627598 dated Sep. 19, 2012.
Schlumberger et al., "A Phase 2 Trial of the Multi-Targeted Kinase Inhibitor Lenvatinib(E7080) in Advanced Medullary Thyroid Cancer (MTC)", 2012 ASCO Annual Meeting, Poster Presentation, Jun. 1-5, 2012.
Funahashi et al., "P-2123, Lenvatinib treatment of differentiated thyroid cancer (DTC): Analysis to identify biomarkers associated with response", The 71$^{st}$ Annual Meeting of the Japanese Cancer Association, p. 339, Sep. 19-21, 2012.
Tohyama et al., "P-3111, Preclinical effect of lenvatinib on human thyroid cancer targeting angiogenesis and receptor tyrosine kinase signaling", The 71$^{st}$ Annual Meeting of the Japanese Cancer Association, p. 502, Sep. 19-21, 2012.
Chinese Office Action for CN 200880003336.6 dated Sep. 5, 2012, with English translation.
Chinese Office Action for CN 200880115011.7 dated Sep. 5, 2012, with English translation.
Notice of Allowance for U.S. Appl. No. 12/986,638, Sep. 25, 2012.
Submission of Documents re Claim 3 and Figure 3 for KR App. Ser. No. 10-2009-7005657, filed on Jul. 13, 2012.
Official Letter for AU2008211952 dated Jul. 10, 2012.
Response to Office Action for U.S. Appl. No. 12/741,682, filed Jul. 30, 2012.
Communication (Notice of Allowance) for JP2011-527665 dated Jul. 17, 2012 (with English translation).
Communication (Notice of Allowance) for EP07806561.2 dated Jun. 25, 2012.
Communication (Notice of Allowance) for EP06782407.8 dated Jun. 20, 2012.
Submission of Documents re UAa201203132, dated May 22, 2012 with English translation.
Office Letter for ZA 2011/08697, dated May 25, 2012.
Response to OA for U.S. Appl. No. 12/439,339 filed Jul. 30, 2012.
Submission of Documents for CO 12-022608 dated Jun. 12, 2012.
Chinese Office Action for CN 200680020317.5 dated Aug. 3, 2012 with English translation.
Sihto, H., "KIT and Platelet-Derived Growth Factor Receptor Alpha Tyrosine Kinase Gene Mutations and KIT Amplifications in Human Solid Tumors", 23 J. Clin. Oncol. 49-57 (Jan. 1, 2005).

Official Letter for SG 201108602-2 dated Aug. 8, 2012.
Alvares Da Silva et al., "A Novel Germ-Line Point Mutation in RET Exon 8 (Gly533Cys) in a Large Kindred with Familial Medullary Thyroid Carcinoma" The Journal of Clinical Endocrinology & Metabolism 88(11):5438-5443 (Nov. 2003).
Yamada et al., "New Technique for Staining", Monthly Medical Technology, Supplementary Volume, Apr. 1999.
European Search Report for EP Appl. No. 07743994.1 dated May 12, 2010.
Furuta, et al., "Synthesis and Biological Evaluation of Selective Inhibitors of PDGF Rector Auto Phosphorylation", Pharmaceutical Research Laboratories, Kirin Brewery Co., Ltd. Takasaki, Gunma, Japan (Sep. 7, 2003).
European Search Report for EP 08846814.5 dated Jun. 18, 2012.
Office Action for JP2007-529565 dated Aug. 7, 2012 with English translation.
Noriyuki et al., "Anti-tumor effect of E7080, a novel angiogenesis inhibitor", Database Biosis (online) Biosciences Information Service, Philadelphia, PA, US., Database Accession No. PREV200800475929 (abstract), Aug. 2008, XP002677323.
European Search Report for EP 08704376.6 dated Jun. 14, 2012.
De Lange et al., "Phase II trial of cisplatin and gemcitabine in patients with advanced gastric cancer", Annals of Oncology, Kluwer, Dordrecht, NL1, 15(3): 484-488, Mar. 1, 2004, XP002511249.
Office Action for IL 199907 issued on Apr. 22, 2012 with English translation.
Office Action for IL 200090 dated Oct. 15, 2012 with English translation.
Office Action (Notice of Allowance) for EP 06782407.8 dated Nov. 2, 2012.
Office Action (Notice of Allowance) for EP 07806561.2 dated Nov. 2, 2012.
Office Action for JP 2008-532141 dated Nov. 13, 2012 with English translation.
Office Action for CN 200980103218.7 dated Sep. 29, 2012 with English translation.
Examination Report for NZ Patent Application No. 598291 dated Oct. 15, 2012.
Response to Office Action for CN200880115011.7 dated Nov. 20, 2012 with English translation.
Response to Office Action for JP2011-527665 dated May 10, 2012 with English translation.
Explanation of Circumstances re Accelerated Examination filed for JP2011-527665 dated May 10, 2012 with English translation.
Office Action for IN 1571/CHENP/2007 dated Oct. 30, 2012.
Office Action for AU 2008325608 dated Nov. 24, 2012.
Office Action for EP 07743994.1 dated Oct. 10, 2012.
Office Action for CN 200780017371.9 dated Sep. 28, 2012 with English translation.
Office Action for JP 2008-516724 dated Oct. 9, 2012 with English translation.
Office Action for CN 201080030508.6 dated Nov. 30, 2012 with English translation.
Response to Office Action for EP 08704376.6 dated Jan. 2, 2013.
Response to Office Action for EP 08846814.5 dated Jan. 3, 2013.
Office Action for IL 205512 dated Dec. 20, 2012 with English translation.
Submission to European Patent Office for EP03791389.4 dated Dec. 20, 2012.
Communication from Israel Patent Office for IL 175363 dated Jan. 2, 2013 with English translation.
Notice of Allowance for U.S. Appl. No. 12/524,754 dated Jan. 18, 2013.
Amendment submitted for Korean Application No. 10-2009-7017694 dated Jan. 18, 2013 with English translation.
Response to Office Action for U.S. Appl. No. 13/322,961 dated Jan. 25, 2013.
Decision of Patent Grant for JP2008-516724 dated Jan. 22, 2013 with English translation.
Office Action for JP2008-556208 dated Jan. 22, 2013 with English translation.
International Preliminary Report on Patentability for PCT/JP2011/064430 dated Jan. 24, 2013.

(56) References Cited

OTHER PUBLICATIONS

Response to Office Action for Canadian Patent Application No. 2627598 dated Jan. 25, 2013.
Office Action for Australian Patent Application No. 2009210098 dated Jan. 30, 2013.
Response to Office Action for European Application No. 07743994.1 dated Feb. 8, 2013.
Request to amend specification for Australian Patent Application No. 2008325608 dated Feb. 15, 2013.
Response to Office Action for Chinese Patent Application No. 200780017371.9 dated Nov. 30, 2012.
European Search Report for Ep 12195436.6 dated Feb. 21, 2013.
English language translation of Office Action dated Jan. 2, 2013 for Israel Patent Application No. 175363.
Amendment for New Zealand Patent Application No. 598291 dated Jan. 30, 2013.
Amendment for Chinese Patent Application No. 201080030508.6 dated Feb. 7, 2013 with English translation.
Response to Office Action for IL Patent Application No. 175363 dated Feb. 27, 2013.
Notice of Allowance for AU Application No. 2008325608 dated Feb. 27, 2013.
Notice of Allowance for U.S. Appl. No. 12/741,682 dated Feb. 19, 2013.
M. Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a Radioresistant Tumor Type, 57 Cancer Res. 5309-5319 (Dec. 1, 1997).
Highlights of Prescribing Information: GLEEVEC® (imatinib mesylate) Tablets for Oral Use (Initial U.S. Approval 2001; Label Revised Jan. 2012).
Response to Office Action for IL Application No. 205512 dated Mar. 14, 2013.
Communication (Notification on Defects in application) for IL Application No. 207089 dated Jan. 6, 2013.
Office Action from CN Patent Application No. 200880115011.7 dated Feb. 25, 2013.
Communication (Notice of Allowance) for CA Patent Application No. 2627598 dated Mar. 8, 2013.
Notice of Acceptance for NZ Application No. 598291 dated Feb. 15, 2013.
Kawano et al., "Presentation Abstract, Abstract Number; 1619,— Combination of VEGFR inhibitor lenvatinib (E7080) and Met/EphB4 inhibitor golvatinib (E7050) overcomes VEGFR inhibitor—resistant I tumor vascular", Annual Meeting 2013, Walter E. Washington Convention Center, Washington, DC, Apr. 6-10, 2013.
Response to Office Action for CN Application No. 200980103218.7 dated Feb. 16, 2013.
Office Action for U.S. Appl. No. 13/624,278 dated Mar. 29, 2013.
Preliminary Amendment for U.S. Appl. No. 13/624,278 filed Sep. 21, 2012.
Response to Chinese Office Action filed for CN 200880003336.6 dated Jul. 11, 2012, with English translation.
Office Action for U.S. Appl. No. 13/322,961 dated Sep. 25, 2012.
Notice of Allowance for U.S. Appl. No. 12/524,754 dated Oct. 9, 2012.
Australian Office Action for Application No. AU2006309551 issued on Apr. 28, 2011.
Australian Response to Office Action for Application No. 2006309551 filed on Jan. 27, 2012.
Australian Office Action for Application No. 2006309551 issued on Feb. 2, 2012.
Chinese Office Action for Application No. 200680041355.9 issued on Mar. 5, 2010 with English translation.
Chinese Response to Office Action for Application No. 200680041355.9 filed on Jul. 19, 2010 with English translation.
Chinese Office Action for Application No. 200680041355.9 issued on Aug. 24, 2010 with English translation.
Chinese Response to Office Action for Application No. 200680041355.9 filed on Nov. 8, 2010 with English translation.
Abrams et al., "SU11248 Inhibits KIT and Platelet-derived Growth Factor Receptor Beta in Preclinical Models of Human Small Cell Lung Cancer", Molecular Cancer Therapeutics., 2: 471-478, 2003.
Carter et al, "Inhibition of drug-resistant mutants of ABL, KIT and EGF receptor kinases", Proceedings of the National Academy of Sciences of the United States of America., 102, 11011-11016, 2005.
CN200780032071.8 Office Action issued on Oct. 13, 2010 with English translation.
CN200780032071.8 Response to Office Action filed on Feb. 16, 2011 with English translation.
Corbin et al., "Sensitivity of oncogenic KIT mutants to the kinase inhibitors MLN518 and PD180970", Blood., 104, 3754-3757, 2004.
EP07806561.2 Office Actions issued on Jan. 19 and Feb. 7, 2011.
EP07806561.2 Response to Office Action filed on Aug. 9, 2011.
EP07806561.2 Office Action issued on Dec. 9, 2011.
European Office Action for Application No. 06832529.9 issued on Oct. 15, 2009.
European Response to Office Action for Application No. 06832529.9 filed on Apr. 22, 2010.
European Office Action for Application No. 06832529.9 issued on Sep. 12, 2011.
European Response to Office Action for Application No. 06832529.9 filed on Oct. 4, 2011.
EP Communication under Rule 71(3) EPC for Application No. 06832529.9 issued on Nov. 25, 2011.
Genitourinary Cancers, Prostate Cancer Genitourinary, http://www.merkmanuals.com/professional/print/sec17/ch241/ch241e.html Mar. 16, 2011.
Guo et al., "Expression of gastric cancer-associated MG7 antigen in gastric cancer, precancerous lesions and *H. pylori*-associated gastric diseases", Word J. Gastroenterol, 8(6):1009-1013 (2002).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
IPRP (PCT/JP2007/067088) dated Mar. 3, 2009 with English translation.
Japanese Publication of Patent Application No. H11-322596 with English translation, Nov. 24, 1999.
Japanese Patent Application No. 2006-230816 (English translation).
Krystal et al., "Indolinone Tyrosine Kinase Inhibitors Block Kit Activation and Growth of Small Cell Lung Cancer Cells", Cancer Research., 61, 3660-3668, 2001.
Leukemias, Hematology and Oncology, http://www.merkmanuals.com/professional/print/sec11/ch142/ch142a.html Mar. 16, 2011.
Nakamura et al., "KRN633: A Selective inhibitor of vascular endothelial growth factor receptor-2 tyrosine kinase that suppresses tumor angiogenesis and growth", Molecular Cancer Therapeutics., 3: 1639-49, 2004.
Pandey et al., "Identification of Orally Active, Potent, and Selective 4-Piperazinylquinazolines as Antagonists of the Platelet-Derived Growth Factor Tyrosine Kinase Family", Journal of Medicinal Chemistry., 45, 3772-3793, 2002.
PCT/JP2006/322514 International Preliminary Report on Patentability issued on May 7, 2008.
PCT/JP2006/322516 International Search Report issued on Jan. 23, 2007.
PCT/JP2006/322516 International Preliminary Report on Patentability issued on May 7, 2008.
Shibata et al., "Rapid Communication Association of Epstein-Barr Virus with Undifferentiated Gastric Carcinomas with Intense Lymphoid Infiltration", American Journal of Pahthology 139(3):469-473 (1991).
Thyroid Cancers, Endocrine and Metabolic Disorders, http://www.merkmanuals.com/professional/print/sec12/ch152/ch152j.html Mar. 16, 2011.
Office Action for U.S. Appl. No. 12/092,539 issued on Oct. 29, 2010.

(56) References Cited

OTHER PUBLICATIONS

Final Office Action for U.S. Appl. No. 12/092,539 issued on May 9, 2011.
Advisory Action for U.S. Appl. No. 12/092,539 issued on Jun. 28, 2011.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Wisniewski et al.,"Characterization of Potent Inhibitors of the Bcr-Abl and the c-Kit Receptor Tyrosine Kinases", Cancer Research., 62, 4244-4255, 2002.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Yigitbasi et al., "Tumor Cell and Endothelial Cell Therapy of Oral Cancer by Dual Tyrosine Kinase Receptor Blockade", Cancer Research, 64, 7977-7984, 2004.
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Sun et al., "Design, synthesis, and evaluations of substituted 3-[(3-or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Bankston et al., "A Scaleable synthesis of BAY 43/9006: A Potent Raf Kinase Inhibitor for the Treatment of Cancer", Organic Process Res Dev., 6:777-81 (2002).
Response to the European Search Report for European Application No. 06782407 filed on Nov. 8, 2010.
Office Action issued for European Search Report for European Application No. 06782407 on Sep. 29, 2011.
Response to the Office Action for European Application No. 06782407 filed on Jan. 23, 2012.
Office Action issued for Japanese Application No. 2007-529565 issued on Dec. 13, 2011 with English translation.
Response to the Office Action issued for Japanese Application No. 2007-529565 filed on Feb. 3, 2012 with English full translation.
Office Action directed at Israel Application No. 207089 issued on Nov. 13, 2011 (with English translation).
Written Opinion of the International Searching Authority directed at PCT/JP2009/051244 issued on Mar. 24, 2009 (with English translation).
International Preliminary Report directed at PCT/JP2009/051244 issued on Aug. 31, 2010 (with English translation).
Office Action for U.S. Appl. No. 13/205,328 dated Jan. 12, 2012.
Israel Office Action directed at Appl. No. 205512 issued on Nov. 13, 2011 with English translation.
PCT/JP2008/070321 Written Opinion of the International Searching Authority issued on Jan. 20, 2009 with English translation.
PCT/JP2008/070321 International Preliminary Report on Patentability issued on May 11, 2010 with English translation.
Sanger et al., "DNA sequencing with chain-terminating inhibitors", Proc. Natl. Acad. Sci. USA 74: 5463 (1977).
Wakui, "Chemotherapy for Scirrhous Gastric Cancer", Japanese Journal of Cancer and Chemotherapy, 21:(14): 2398-2406 (1994) (English translation only).
Takahashi et al., "A Case of Inoperable Scirrhous Gastric Cancer that Responded Remarkably to a Combination . . . Loss of Ascites", Japanese Journal of Cancer and Chemotherapy, 31(7):1093-1095 (2004) (English translation only).
PCT/JP2008/051697 Written Opinion of the International Searching Authority issued on Mar. 4, 2008.
PCT/JP2008/051697 International Preliminary Report on Patentability issued on Aug. 4, 2009.
CN200880003336.6 Response to Office Action filed on Oct. 8, 2011.
Israel 200090 Office Actions issued on Jun. 22, 2010.
Israel 200090 Response to Office Action filed on Oct. 12, 2010.
Office Action issued for EP application No. 07806561.2 on Dec. 9, 2011.
Response to Office Action directed at Australain Appl. No. 2006309551 filed on Mar. 30, 2012.
US Final Office Action for U.S. Appl. No. 12/439,339 dated Mar. 30, 2012.
Zimmermann et al., "Potent and Selective Inhibitors of the ABL-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
"Current Protocols in Molecular Biology", John Wiley & Sons Section 11.4-11.13 (1987).
Antibodies: A Laboratory Manual, E. Harlow and D. Lane, ed.. Cold Spring Harbor Laboratory (Cold Spring Harbour, NY, 1988).
First Office Action issued on Mar. 6, 2012 for the corresponding JP application, JP2007-542863, and English translation.
Amendment and Argument filed on Apr. 27, 2012 in response to the JP Office Action for JP2007- 542863 and English translation.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Paulus, "Preparation and Biomedical Applications of Bispecific Antibodies", Behring Inst. Mitt. 78: 118-132 (1985).
Waterman, M., "Computer Analysis of Nucleic Acid Sequences", Methods in Enzymology, 164:765-793 (1988).
Wilbur, W.J. and Lipman, D.J., "Rapid similarity searches of nucleic acid and protein data banks", Natl. Acad. Sci, U.S.A. 80:726-730 (1983).
Altschul et al., "Basic Local Alignment Search Tool", J. Mol. Biol. 215:403-410 (1990).
Pearson, "Rapid and Sensitive Sequence Comparison with FASTP and FASTA", Methods in Enzymology 183:63-98 (1990).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Classification of Gastric Carcinoma "Igan-Toriatsukai Kiyaku" (Jun. 1999, 13th ed.) and an English translation.
Voluntary Amendment filed on Feb. 17, 2012 for TH patent appl. No. 1201000221 with English translation.
Office Action dated Apr. 11, 2012 for RU patent appl. No. 2012103471 with English translation.
Office Action dated Apr. 27, 2012 for KR patent appl. No. 10-2007-7001347 with English translation.
Office Action dated May 3, 2012 for IN patent appl. No. 383/CHENP/2008.
Examination Report dated May 9, 2012 for PK patent appl. No. 94/2011.
Office Action dated Jun. 5, 2012 for JP patent appl. No. 2009-123432 with English translation.
Response to the OA filed on May 29, 2012 for RU patent appl. No. 2012103471 with English translation.
Examiner's Report dated Sep. 20, 2005 for AU Patent Application No. 2001295986.
Response filed on Apr. 27, 2006 for AU Patent Application No. 2001295986.
Examiner's Report dated May 4, 2006 for AU Patent Application No. 2001295986.
Response filed on Jul. 26, 2006 for AU Patent Application No. 2001295986.

(56) References Cited

OTHER PUBLICATIONS

Notice of Acceptance dated Aug. 3, 2006 for AU Patent Application No. 2001295986.
Voluntary Amendment filed on Aug. 30, 2006 for AU Patent Application No. 2006203099.
Examiner's Report dated Feb. 21, 2008 for AU Patent Application No. 2006203099.
Voluntary Amendment filed on Feb. 21, 2007 for AU Patent Application No. 2006203099.
Voluntary Amendment filed on Feb. 27, 2007 for AU Patent Application No. 2006236039.
Examiner's Report dated Mar. 26, 2008 for AU Patent Application No. 2006236039.
Response filed on May 8, 2008 for AU Patent Application No. 2006236039.
Notice of Acceptance dated May 13, 2008 for AU Patent Application No. 2006236039.
Office Action dated Dec. 6, 2007 for CA Patent Application No. 2426461.
Response filed on May 16, 2008 for CA Patent Application No. 2426461.
Office Action dated Nov. 20, 2008 for CA Patent Application No. 2426461.
Response filed on Feb. 23, 2009 for CA Patent Application No. 2426461.
Office Action dated May 8, 2009 for CA Patent Application No. 2426461.
Response filed on Aug. 13, 2009 for CA Patent Application No. 2426461.
Office Action dated Feb. 10, 2010 for CA Patent Application No. 2426461.
Response filed on May 20, 2010 for CA Patent Application No. 2426461.
Voluntary Amendment filed on Aug. 19, 2010 for CA Patent Application No. 2426461.
Notice of Allowance dated Oct. 14, 2010 for CA Patent Application No. 2426461.
Amendment after Allowance filed on Jan. 4, 2011 for CA Patent Application No. 2426461.
Office Letter Confirmation of Amendment After Allowance dated Jan. 11, 2011 for CA Patent Application No. 2426461.
Amendment filed on May 28, 2003 for CN Patent Application No. 01819710.8 with English translation.
Office Action dated May 13, 2005 for CN Patent Application No. 01819710.8 with English translation.
Response filed on Sep. 13, 2005 for CN Patent Application No. 01819710.8 with English translation.
Amendment filed on Sep. 13, 2005 for CN Patent Application No. 01819710.8 with English translation.
Office Action dated Feb. 10, 2006 for CN Patent Application No. 01819710.8 with English translation.
Response filed on Apr. 11, 2006 for CN Patent Application No. 01819710.8 with English translation.
Amendment filed on Apr. 11, 2006 for CN Patent Application No. 01819710.8 with English translation.
Office Action dated Aug. 11, 2006 for CN Patent Application No. 01819710.8 with English translation.
Response filed on Oct. 9, 2006 for CN Patent Application No. 01819710.8.
Amendment filed on Oct. 9, 2006 for CN Patent Application No. 01819710.8.
Notice of Allowance dated Dec. 15, 2006 for CN Patent Application No. 01819710.8 with.
Office Action dated Jul. 24, 2009 for CN Patent Application No. 200710007096.4.
Office Action dated Mar. 6, 2009 for CN Patent Application No. 200710007097.9.
Response filed on Jul. 2, 2009 for CN Patent Application No. 200710007097.9.
Amendment filed on Jul. 2, 2009 for CN Patent Application No. 200710007097.9.
Office Action dated Sep. 11, 2009 for CN Patent Application No. 200710007097.9 with.
Response filed on Nov. 19, 2009 for CN Patent Application No. 200710007097.9 with English translation.
Amendment filed on Nov. 19, 2009 for CN Patent Application No. 200710007097.9 with English translation.
Office Action dated Dec. 25, 2009 for CN Patent Application No. 200710007097.9 with English translation.
Response filed on Jan. 26, 2010 for CN Patent Application No. 200710007097.9 with English translation.
Amendment filed on Jan. 26, 2010 for CN Patent Application No. 200710007097.9 with English translation.
Office Action dated Apr. 27, 2010 for CN Patent Application No. 200710007097.9 with English translation.
Response filed on Jun. 22, 2010 for CN Patent Application No. 200710007097.9 with English translation.
Amendment filed on Jun. 22, 2010 for CN Patent Application No. 200710007097.9 with English translation.
Voluntary Amendment filed on Aug. 11, 2010 for CN Patent Application No. 200710007097.9 with English translation.
Notice of Allowance dated Oct. 9, 2010 for CN Patent Application No. 200710007097.9 with English translation.
Partial European Search Report for EP Patent Application No. 01976786.2; Apr. 6, 2004.
Supplementary European Search Report for EP Patent Application No. 01976786.2; Jul. 6, 2004.
Invitation to declare maintenance of the application for EP Patent Application No. 01976786.2; Jul. 12, 2004.
Maintenance of the application for EP Patent Application No. 01976786.2; Sep. 6, 2004.
Amendments received before examination for EP Patent Application No. 01976786.2; Sep. 10, 2004.
Communication from the Examining Division for EP Patent Application No. 01976786.2; Aug. 17, 2004.
Brief communication to applicant for EP Patent Application No. 01976786.2; Sep. 9, 2005.
Communication from the Examining Division for EP Patent Application No. 01976786.2; Sep. 19, 2005.
Reply to communication from the Examining Division for EP Patent Application No. 01976786.2; Jan. 25, 2006.
Communication from the Examining Division for EP Patent Application No. 01976786.2; Mar. 21, 2006.
Reply to communication from the Examining Division for EP Patent Application No. 01976786.2; Jul. 19, 2006.
Communication about intention to grant a European patent for EP Patent Application No. 01976786.2; Sep. 4, 2006.
Decision to want a European patent for EP Patent Application No. 01976786.2; Feb. 1, 2007.
Communication regarding the expiry of opposition period for EP Patent Application No. 01976786.2; Jan. 4, 2008.
European search report for EP Patent Application No. 04025700.8; Jan. 13, 2005.
Communication from the Examining Division for EP Patent Application No. 04025700.8; Apr. 10, 2006.
Reply to communication from the Examining Division for EP Patent Application No. 04025700.8; Sep. 12, 2006.
Communication from the Examining Division for EP Patent Application No. 04025700.8; Oct. 23, 2006.
Reply to communication from the Examining Division for EP Patent Application No. 04025700.8; Jan. 26, 2007.
Reply to communication from the Examining Division for EP Patent Application No. 04025700.8; Feb. 15, 2007.
Communication about intention to grant a European patent for EP Patent Application No. 04025700.8; Oct. 15, 2007.
Request for amendment of the text intended for grant and translation of claims for EP Patent Application No. 04025700.8; Feb. 1, 2008.
Approval of request for amendments for EP Patent Application No. 04025700.8; Mar. 13, 2008.
Decision to grant a European patent for EP Patent Application No. 04025700.8; Jun. 5, 2008.

(56) References Cited

OTHER PUBLICATIONS

Communication regarding the expiry of opposition period for EP Patent Application No. 04025700.8; May 7, 2009.
Deficiencies in sequence listing for EP Patent Application No. 06023078.6; Dec. 5, 2006.
Reply to the invitation to remedy deficiencies for EP Patent Application No. 06023078.6; Jan. 11, 2007.
Request for correction of errors in filed documents for EP Patent Application No. 06023078.6; Feb. 13, 2007.
European Search Report for EP Patent Application No. 06023078.6; Mar. 16, 2007.
Information about decision on request for EP Patent Application No. 06023078.6; Mar. 21, 2007.
Invitation to declare maintenance of the application for EP Patent Application No. 06023078.6; May 2, 2007.
Maintenance of the application for EP Patent Application No. 06023078.6; Jun. 19, 2007.
Communication from Examining Division for EP Patent Application No. 06023078.6; Aug. 2, 2007.
Reply to communication from the Examining Division for EP Patent Application No. 06023078.6; Sep. 11, 2007.
Communication from the Examining Division for EP Patent Application No. 06023078.6; Sep. 26, 2007.
Reply to communication from the Examining Division for EP Patent Application No. 06023078.6; Feb. 4, 2008.
Communication about intention to grant a European patent for EP Patent Application No. 06023078.6; Jul. 18, 2008.
Request for amendment of the text intended for grant and translation of claims for EP Patent Application No. 06023078.6; Nov. 5, 2008.
Decision to grant a European patent for EP Patent Application No. 06023078.6; Dec. 4, 2008.
Communication regarding the expiry of opposition period for EP Patent Application No. 06023078.6; Nov. 4, 2009.
"Voluntary Amendment filed on Sep. 10, 2010 for HU Patent Application No. P0302603" with English translation.
"Office Action dated Oct. 16, 2007 for IL Patent Application No. 155447" with English translation.
"Response filed on Dec. 4, 2007 for IL Patent Application No. 155447" with English translation.
"Notice of Allowance dated Dec. 26, 2007 for IL Patent Application No. 155447" with English translation.
"Notice Prior to Examination dated Jun. 29, 2008 for IL Patent Application No. 189677" with English translation.
"Response to Notice Prior to Examination filed on Jan. 11, 2009 for IL Patent Application No. 189677" with English translation.
"Office Action dated Feb. 18, 2009 for IL Patent Application No. 189677" with English translation.
"Response filed on May 13, 2009 for IL Patent Application No. 189677"with English translation.
"Notice of Allowance dated Mar. 14, 2010 for IL Patent Application No. 189677" with English translation.
"Amendment filed on Mar. 7, 2005 for JP Patent Application No. 2002-536056" with English translation.
"Office Action dated Apr. 11, 2005 for JP Patent Application No. 2002-536056" with English translation.
"Argument filed on Apr. 19, 2005 for JP Patent Application No. 2002-536056" with English translation.
"Amendment filed on Apr. 19, 2005 for JP Patent Application No. 2002-536056" with English translation.
"Notice of Allowance dated Aug. 2, 2005 for JP Patent Application No. 2002-536056" with English translation.
"Office Action dated Jan. 27, 2009 for JP Patent Application No. 2005-124034" with English translation.
Japanese Patent Application Laid-Open No. H11-158149 with English translation.
"Argument filed on Mar. 23, 2009 for JP Patent Application No. 2005-124034" with English translation.
"Amendment filed on Mar. 23, 2009 for JP Patent Application No. 2005-124034" with English translation.
"Office Action dated Apr. 28, 2009 for JP Patent Application No. 2005-124034" with English translation.
"Argument filed on May 21, 2009 for JP Patent Application No. 2005-124034" with English translation.
"Amendment filed on May 21, 2009 for JP Patent Application No. 2005-124034" with English translation.
"Notice of Allowance dated Jul. 21, 2009 for JP Patent Application No. 2005-124034" with English translation.
"Written Amendment filed on Jun. 16, 2009 for JP Patent Application No. 2009-123432" with English translation.
"Written Statement filed on Jun. 16, 2009 for JP Patent Application No. 2009-123432" with English translation.
"Preliminary Amendment filed on May 23, 2003 for KR Patent Application No. 10-2003-7005506" with English translation.
"Office Action dated Jul. 27, 2005 for KR Patent Application No. 10-2003-7005506" with English translation.
"Argument Brief filed on Oct. 25, 2005 for KR Patent Application No. 10-2003-7005506" with English translation.
"Amendment filed on Oct. 25, 2005 for KR Patent Application No. 10-2003-7005506" with English translation.
"Office Action dated Jan. 5, 2006 for KR Patent Application No. 10-2003-7005506" with English translation.
"Argument Brief filed on Mar. 6, 2006 for KR Patent Application No. 10-2003-7005506" with English translation.
"Amendment filed on Mar. 6, 2006 for KR Patent Application No. 10-2003-7005506" with English translation.
"Notice of decision for patent dated Jun. 12, 2006 for KR Patent Application No. 10-2003-7005506" with English translation.
"Office Action dated Dec. 8, 2005 for KR Patent Application No. 10-2005-7020292" with English translation.
"Argument Brief filed on Mar. 8, 2006 for KR Patent Application No. 102005-7020292" with English translation.
"Amendment filed on Mar. 8, 2006 for KR Patent Application No. 10-2005-7020292" with English translation.
"Notice of decision for patent dated Apr. 17, 2006 for KR Patent Application No. 10-2005-7020292" with English translation.
"Office Action dated Oct. 4, 2005 for MX Patent Application No. PA/a/2003/003362" with English translation.
"Response filed on Dec. 15, 2005 for MX Patent Application No. PA/a/2003/003362" with English translation.
"Office Action dated Jun. 7, 2006 for MX Patent Application No. PA/a/2003/003362" with English translation.
"Response filed on Aug. 21, 2006 for MX Patent Application No. PA/a/2003/003362" with English translation.
"Notice of Allowance dated Oct. 18, 2006 for MX Patent Application No. PA/a/2003/003362" with English translation.
"Office Action dated Nov. 26, 2007 for MX Patent Application No. PA/a/2005/013764" with English translation.
"Office Action dated Mar. 7, 2007 for NO Patent Application No. 20031731" with English translation.
"Response filed on Sep. 10, 2007 for NO Patent Application No. 20031731" with English translation.
"Office Action dated Oct. 4, 2007 for NO Patent Application No. 20031731" with English translation.
"Response filed on May 7, 2008 for NO Patent Application No. 20031731" with English translation.
"Office Action dated May 16, 2008 for NO Patent Application No. 20031731" with English translation.
"Response filed on Aug. 18, 2008 for NO Patent Application No. 20031731" with English translation.
"Office Action dated Sep. 5, 2008 for NO Patent Application No. 20031731" with English translation.
"Response filed on Oct. 13, 2008 for NO Patent Application No. 20031731" with English translation.
"Notice of Allowance dated Oct. 31, 2008 for NO Patent Application No. 20031731" with English translation.
"Examination Report dated Oct. 13, 2003 for NZ Patent Application No. 525324".
"Response filed on Aug. 26, 2004 for NZ Patent Application No. 525324".
"Examination Report dated Sep. 2, 2004 for NZ Patent Application No. 525324".

(56) References Cited

OTHER PUBLICATIONS

"Response filed on Jan. 21, 2005 for NZ Patent Application No. 525324".
"Examination Report dated Feb. 18, 2005 for NZ Patent Application No. 525324".
"Notice of Acceptance of Complete Specification dated Mar. 4, 2005 for NZ Patent Application No. 525324".
"Formality Requirement dated Jun. 18, 2003 for PH Patent Application No. 1-2003-500266".
"Response filed on Aug. 5, 2003 for PH Patent Application No. 1-2003-500266".
"Office Action dated Aug. 8, 2003 for PH Patent Application No. 1-2003-500266".
"Response filed on Sep. 8, 2003 for PH Patent Application No. 1-2003-500266".
"Response filed on Sep. 15, 2003 for PH Patent Application No. 1-2003-500266".
"Office Action dated Jul. 21, 2006 for PH Patent Application No. 1-2003-500266".
"Response filed on Aug. 14, 2006 for PH Patent Application No. 1-2003-500266".
"Office Action dated Mar. 21, 2007 for PH Patent Application No. 1-2003-500266".
"Response filed on Apr. 17, 2007 for PH Patent Application No. 1-2003-500266".
"Office Action dated Jun. 27, 2007 for PH Patent Application No. 1-2003-500266".
"Response filed on Jul. 31, 2007 for PH Patent Application No. 1-2003-500266".
"Office Action dated Sep. 7, 2007 for PH Patent Application No. 1-2003-500266".
"Response filed on Oct. 15, 2007 for PH Patent Application No. 1-2003-500266".
"Notice of Allowability dated Nov. 28, 2007 for PH Patent Application No. 1-2003-500266".
"Response to the Notice of Allowability filed on Dec. 13, 2007 for Ph Patent Application No. 1-2003-500266".
"Notification dated Apr. 25, 2008 for PH Patent Application No. 1-2003-500266".
"Response filed on Apr. 30, 2008 for PH Patent Application No. 1-2003-500266".
"Registered dated Feb. 24, 2009 for PH Patent Application No. 1-2003-500266".
"Office Action dated Jun. 29, 2004 for RU Patent Application No. 2003114740" with English translation.
"Response filed on Nov. 30, 2004 for RU Patent Application No. 2003114740" with English translation.
"Office Action dated Jan. 19, 2005 for RU Patent Application No. 2003114740" with English translation.
"Response filed on Mar. 17, 2005 for RU Patent Application No. 2003114740" with English translation.
"Notice of Allowance dated Apr. 19, 2005 for RU Patent Application No. 2003114740" with English translation.
"Amendment filed on Apr. 17, 2002 for TW Patent Application No. 90125928" with English translation.
"Rejection dated Apr. 26, 2004 for TW Patent Application No. 90125928" with English translation.
"Reexamination filed on Nov. 25, 2004 for TW Patent Application No. 90125928" with English translation.
"Office Action dated Oct. 11, 2007 for TW Patent Application No. 90125928" with English translation.
"Response filed on Dec. 11, 2007 for TW Patent Application No. 90125928" with English translation.
"Notice of Allowance dated Oct. 20, 2008 for TW Patent Application No. 90125928" with English translation.
"Notice of Allowance dated Jun. 3, 2008 for U.S. Appl. No. 11/293,785".
"Notice of Allowance dated Nov. 19, 2008 for U.S. Appl. No. 11/293,785".
"Notice of Allowance dated Feb. 27, 2009 for U.S. Appl. No. 11/293,785".
"Notice of Allowance dated May 18, 2009 for U.S. Appl. No. 11/293,785".
"Preliminary Amendment filed on Apr. 18, 2003 for U.S. Appl. No. 10/420,466".
"Office Action dated Apr. 13, 2005 for U.S. Appl. No. 10/420,466".
"Response filed on Jul. 1, 2005 for U.S. Appl. No. 10/420,466".
"Notice of Allowance dated Sep. 12, 2005 for U.S. Appl. No. 10/420,466".
"Notice of Allowance dated Jun. 13, 2006 for U.S. Appl. No. 10/420,466".
"Notice of Allowance dated Mar. 16, 2007 for U.S. Appl. No. 10/420,466".
Preliminary Amendment filed on Dec. 2, 2005 for U.S. Appl. No. 11/293,785.
"Preliminary Amendment filed on Feb. 3, 2006 for U.S. Appl. No. 11/293,785".
"Office Action dated Sep. 4, 2007 for U.S. Appl. No. 11/293,785".
"Response filed on Feb. 26, 2008 for U.S. Appl. No. 11/293,785".
"Notification of Non-Compliant Amendment filed on Jan. 13, 2005 for U.S. Appl. No. 10/420,466".
"Office Communication concerning dated Sep. 13, 2004 for U.S. Appl. No. 10/420,466".
"Response filed on Oct. 8, 2004 for U.S. Appl. No. 10/420,466".
"Preliminary Amendment filed on Oct. 27, 2003 for U.S. Appl. No. 10/420,517".
ISR dated Jan. 15, 2002 for International Patent Application No. PCT/JP01/09221.
IPRP dated Jan. 8, 2003 for International Patent Application No. PCT/JP01/09221.
Amendment filed on Aug. 4, 2004 for ZA Patent Application No. 2003/3567.
Notice of Acceptance dated Aug. 10, 2004 for ZA Patent Application No. 2003/3567.
Amendment filed on Aug. 17, 2004 for ZA Patent Application No. 2003/3567.
Amended description filed after receipt of search report for EP Patent Application No. 10809938.3; Dec. 8, 2011.
"Amendment filed on Dec. 12, 2011 for JO Patent Application No. 55/2011" with English translation.
"Written Amendment filed on Sep. 21, 2011 for JP Patent Application No. 2011-527665" with English translation.
"Written Statement filed on Sep. 21, 2011 for JP Patent Application No. 2011-527665" with English translation.
Amendment filed on Oct. 28, 2011 for LB Patent Application No. 9292.
Amendment filed on Feb. 9, 2011 for TW Patent Application No. 100104281.
"Amendment filed on Dec. 15, 2011 for VN Patent Application No. 1-2011-03484" with English translation.
"ISR dated Sep. 14, 2010 for International Patent Application No. PCT/JP2010/063804".
"IPRP dated Mar. 13, 2012 for International Patent Application No. PCT/JP2010/063804".
Amendment filed on Dec. 22, 2011 for ZA Patent Application No. 2011/08697.
"Voluntary Amendment filed on Feb. 9, 2010 for AU Patent Application No. 2005283422".
"Notice of Allowance dated Apr. 29, 2010 for AU Patent Application No. 2005283422".
"Voluntary Amendment filed on Jul. 6, 2010 for AU Patent Application No. 2005283422".
"Office Action dated Jul. 15, 2011 for CA Patent Application No. 2579810".
"Response filed on Sep. 21, 2011 for CA Patent Application No. 2579810".
"Notice of Allowance dated Oct. 17, 2011 for CA Patent Application No. 2579810".
"Office Action dated Jun. 26, 2009 for CN Patent Application No. 200580026468.7" with English translation.
"Response filed on Sep. 23, 2009 for CN Patent Application No. 200580026468.7" with English translation.

(56) References Cited

OTHER PUBLICATIONS

"Amendment filed on Sep. 23, 2009 for CN Patent Application No. 200580026468.7" with English translation.
"Office Action dated Nov. 20, 2009 for CN Patent Application No. 200580026468.7" with English translation.
"Response filed on Jan. 11, 2010 for CN Patent Application No. 200580026468.7" with English translation.
"Amendment filed on Jan. 11, 2010 for CN Patent Application No. 200580026468.7" with English translation.
"Notice of Allowance dated Feb. 5, 2010 for CN Patent Application No. 200580026468.7" with English translation.
Communication regarding the expiry of opposition period for EP Patent Application No. 05783232.1; Feb. 19, 2010.
"Decision to grant a European patent for EP Patent Application No. 05783232.1; Mar. 19, 2009".
"Communication about intention to grant a European patent for EP Patent Application No. 05783232.1; Nov. 20, 2008".
"Reply to official communication for EP Patent Application No. 05783232.1; Apr. 30, 2008".
"Communication from the Examining Division for EP Patent Application No. 05783232.1; Feb. 7, 2008".
"Maintainance of the application for EP Patent Application No. 05783232.1; Nov. 9, 2007".
Invitation to declare maintenance of the application for EP Patent Application No. 05783232.1; Sep. 25, 2007.
"European Search Report for EP Patent Application No. 05783232.1; Sep. 7, 2007".
"Notice Prior to Examination dated Mar. 9, 2009 for IL Patent Application No. 181697" with English translation.
"Response to Notice Prior to Examination filed on Apr. 22, 2009 for IL Patent Application No. 181697" with English translation.
"Office Action dated Dec. 20, 2010 for IL Patent Application No. 181697" with English translation.
"Response filed on Jan. 26, 2011 for IL Patent Application No. 181697" with English translation.
"Notice of Allowance dated Nov. 14, 2011 for IL Patent Application No. 181697" with English translation.
"Notice of Allowance dated Sep. 20, 2011 for JP Patent Application No. 2006-535174" with English translation.
Japanese Patent Application Laid-Open No. S63-028427 with English translation, Feb. 6, 1988.
Japanese Patent Application Laid-Open No. 2003-026576 with English translation, Jan. 29, 2003.
WO00/071097 with English translation, Nov. 30, 200.
"Office Action dated Sep. 28, 2011 for KR Patent Application No. 102007-7001347" with English translation.
"Amendment filed on Nov. 24, 2011 for KR Patent Application No. 10-2007-7001347" with English translation.
"Argument Brief filed on Nov. 24, 2011 for KR Patent Application No. 10-2007-7001347" with English translation.
"ISR dated Nov. 15, 2005 for International Patent Application No. PCT/JP2005/016941".
"IPRP dated Mar. 20, 2007 for International Patent Application No. PCT/JP2005/016941".
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Hori et al., "Suppression of Solid Tumor Growth by Immunoneutralizing Monoclonal Antibody against Human Basic Fibroblast Growth Factor", Cancer Research., 51, 6180-4, 1991.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Dias et al., "IL-12 Regulates VEGF and MMPs in a Murine Breast Cancer Model", International J. Cancer., 78, 361-5, 1998.
Liu et al., "Structure of Human Methionine Aminopeptidase-2 Complexed with Fumagillin", Science., 282, 1324-1327, 1998.

Wedge et al., "ZD4190: An Orally Active Inhibitor of Vascular Endothelial Growth Factor Signaling with Broad-Spectrum Antitumor Efficacy", Cancer Research., 60, 970-975, 2000.
Hannequin et al., "Design and Structure-Activity Relationship of a New Class of Potent VEGF Receptor Tyrosine Kinase Inhibitors", Journal of Medicinal Chemistry., 42: 5369-5389, 1999.
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Laird et al., "SU6668 Is a Potent Antiangiogenic and Antitumor Agent That Induces Regression of Established Tumors1", Cancer Research., 60, 4152-4160, 2000.
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.
Kubo et al., "Novel Potent Orally Active Selective VEGFR-2 Tyrosine Kinase Inhibitors: . . . ureas", Journal of Medicinal Chemistry., 48, 1359-1366, 2005.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Podar et al., "GW654652, the pan-inhibitor of VEGF receptors, blocks the growth and migration of multiple myeloma cells in the bone marrow microenvironment", Blood.,103, 3474-3479, 2004.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Ueda et al., "VGA1155, a Novel Binding Antagonist of VEGF, Inhibits Angiogenesis In Vitro and In Vivo", Anticancer Research., 24, 3009-3017, 2004.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Mohammadi et al., "Crystal structure of an angiogenesis inhibitor bound to the FGF receptor tyrosine kinase domain", EMBO J., 17, 5896-5904, 1998.
Roberts et al., "Antiangiogenic and Antitumor Activity of a Selective PDGFR Tyrosine Kinase Inhibitor, CP-673,451", Cancer Research., 65, 957-966, 2005.
Kubo et al., "A Novel Series of 4-Phenoxyquinolines: Potent and Highly Selective Inhibitors of PDGF Receptor Autophosphorylation", Bioorganic and Medicinal Chemistry Letters., 7, 2935-2940, 1997.
Wood et al., "A Unique Structure for Epidermal Growth Factor Receptor Bound to GW572016 (Lapatinib): Relationships among

(56) References Cited

OTHER PUBLICATIONS

Protein Conformation, Inhibitor Off-Rate, and Receptor Activity in Tumor Cells", Cancer Research., 64, 6652-6659. 2004.
Nyati et al., "Radiosensitization by Pan ErbB Inhibitor CI-1033 in Vitro and in Vivo", Clinical Cancer Research., 10:691-700, 2004.
El-Abseri et al., "Chemoprevention of UV Light-Induced Skin Tumorigenesis by Inhibition of the Epidermal Growth Factor Receptor", Cancer Research., 64, 3958-3965, 2004.
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Experimental Medicine, Supplementary Volume, "A New Handbook of Genetic Engineering", Section 4, Yodosha, 2003(Japanese).
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Masferrer et al., "COX-2 Inhibitors a New Class of Antiangiogenic Agents", Annals of N.Y. Acad. Science., 889:84-6, 1999.
Bramhall, S., "The Matrix Metalloproteinases and Their Inhibitors in Pancreatic Cancer", International J. Pancreatol., 21, 1-12, 1997.
AACR American Association Cancer Research, 92nd Annual Meeting, 42:583, Mar. 24-28, 2001, New Orleans, LA, USA, 3126.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
EORTC-NCI-AACR Symp Mol Targets Cancer Ther., 2, (Abstract 172), 2004.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
ZK304709 (Proceedings of the American Association for Cancer Research, 46, (Abstract 5842), 2005.
EORTC-NCI-AACR Symp Mol Targets Cancer Ther., (Abstract 134), 2004.
EORTC-NCI-AACR Symp Mol Targets Cancer Ther., 2, (Abstract 151), 2004.
Proceedings of the American Association for Cancer Research, 44, 9, (Abstract 39), 2003.
Proceedings of the American Association for Cancer Research, 44, 9, (Abstract 40), 2003.
Proceedings of the American Association for Cancer Research, 45, 694, (Abstract 3005), 2004.
Proceedings of the American Association for Cancer Research, 44, 1479, (Abstract 6454), 2003.
Proc. Am. Soc. Clin. Oncology, (Abstract 776), 2003.
Am. Assoc. Cancer Research, A3394, 2005.
Am. Assoc. Cancer Research, A3405, 2005.
"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.
Kim, T, "Technology evaluation: Matuzumab, Merck KGaA", Curr Opin Mol Ther. 2004; 6(1):96-103.
Am. Assoc. Cancer Research, Abstract 5353, 2005.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.

The Pharmacology of Monoclonal Antibody, vol. 113, Chapter 11, Rosenburg and Moore ed., Springer Verlag (1994) pp. 269-315.
LeDoussal et al. "Bispecific-Antibody-Mediated Targeting of Radiolabeled Bivalent Haptens: Theoretical, Experimental and Clinical Results", Int. J. Cancer Suppl. 7: 58-62, 1992.
Millstein and Cuello, "Hybrid hybridomas and their use in immunohistochemistry", Nature 305: 537-9, 1983.
Am. Assoc. Cancer Res. Abstract 3399, 2005.
Proceedings of the American Association for Cancer Research, 45, 594, (Abstract 2571), 2004.
Proceedings of the American Association for Cancer Research, 44, 865, (Abstract 3780), 2003.
Decision of Rejection issued on May 29, 2012 for JP No. 2007-542863 with English translation.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
Kinlaw et al., "Multiple endocrine neoplasia 2A due to a unique C609S RET mutation presents with pheochromocytoma and reduced penetrance of medullary thyroid carcinoma", Clin Endocrinol, 69, 676-682 2005.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Kruckeberg et al., "Pyrosequencing Technology as a Method for the Diagnosis of Multiple Endocrine Neoplasia Type 2", Clinical Chemistry, 50, 522-529, 2004.
Bartsch et al., "A RET double mutation in the germline of a kindred with FMTC", Exp. Clin Endocrinol Diabetes, 108, 128-132, 2000.
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Hara et al., "Amplification of c-myc, K-sam, and c-met in Gastric Cancers: Detection by Fluorescence in Situ Hybridization", Laboratory Investigation, 78, 1143-1153, 1998.
Office Action issued for JP Appl. No. 2007-529565 issued on May 8, 2012 with English translation.
Response to EP OA for EP 07806561.2 filed on Apr. 18, 2012.
Response to CN OA for CN200880003336.6 filed on May 3, 2012.
Response to IL OA for IL 195282 filed on May 28, 2012.
Response to AU OA for AU 2008211952 filed on Jun. 28, 2012.
Heinemann, V., et al., "Comparison of the Cellular Pharmacokinetics and Toxicity of . . . 1-beta-d-Arabinofuranosylcytosine", Cancer Research, 48, 4024-4031, 1988.
Hertel LW., et al., "Evaluation of the Antitumor Activity of Gemcitabine (2',2'-Difluoro-2'- deoxycytidine)", Cancer Research, 50, 4417-4422, 1990.
IPRP (PCT/JP2008/051024)dated Jul. 21, 2009, with English translation.
Office Action issued for CN 200880002425.9 on Mar. 2, 2011 with English translation.
Argument and Amendment for CN 200880002425.9 filed on Jul. 18, 2011 with English translation.
Office Action for CN 200880002425.9 issued on Mar. 7, 2012 with English translation.
Office Action for IL 199907 issued on Jun. 17, 2010 with English translation.
Response to Office Action for IL 199907 filed on Oct. 11, 2010 with English translation.
Office Action issued for EP06768437.3 (EPO Form1224) issued on Oct. 28, 2010.
Response to OA for EP10015141 filed on Mar. 5, 2012.
PCT/JP2006/0315563 Written Opinion of the International Searching Authority dated Feb. 5, 2008, with English translation.
PCT/JP2006/315563 International Preliminary Report on Patentability dated Feb. 5, 2008, with English translation.
PCT/JP2006/0315698 Written Opinion of the International Searching Authority, dated Feb. 5, 2008, with English translation.
PCT/JP2006/315698 International Preliminary Report on Patentability with dated Feb. 5, 2008, English translation.

(56) References Cited

OTHER PUBLICATIONS

Response to Office Action for IL 200090 dated Dec. 23, 2012 (with English translation).
European Search Report for EP 10809938.3 dated Jan. 2, 2013.
Office Action from CN Patent Application No. 200780017371.9 dated Mar. 14, 2013 (with English translation).
Response to Office Action for IN Patent Application No. 1571/CHENP/2007 dated Apr. 10, 2013.
Office Action for U.S. Appl. No. 11/997,719 dated Apr. 8, 2013.
Office Action for CN Patent Application No. 201080030508.6 dated Apr. 9, 2013 (with English translation).
Office Action for CA Application No. 2652442 dated Apr. 16, 2013.
Office Action for IL Patent Application No. 217197 dated Apr. 11, 2013 with English translation.
Response to Office Action for IL Application No. 207089 dated Apr. 22, 2013 (with English translation).
Preliminary Amendment for U.S. Appl. No. 13/870,507, filed Apr. 26, 2013.
Communication (Notice of Allowance) for EP Application No. 04818213.3 dated May 6, 2013.
Request to amend specification for Australian Patent Application No. 2009210098 dated May 9, 2013.
Amendment and RCE for U.S. Appl. No. 12/741,682 dated May 17, 2013.
Supplementary Observation for CN Application No. 200980103218.7 dated Mar. 13, 2013 (with English translation).
Response to Office Action for CN Application No. 200880115011.7 dated Apr. 11, 2013 (with English translation).
Office Action for EP08846814.5 dated Apr. 16, 2013.
Request for Continued Examination and Information Disclosure Statement for U.S. Appl. No. 12/524,754, filed Apr. 15, 2013.
Office Action for KR 10-2008-7013685 dated May 20, 2013 (with English translation).
Office Action for JP2008-532141 dated May 21, 2013 (with English translation).
Office Action for U.S. Appl. No. 12/439,339 dated May 23, 2013.
Applicant Interview Summary for U.S. Appl. No. 12/439,339 dated May 23, 2013.
Response to Office Action for CN201080030508.6 dated May 27, 2013 (with English translation).
Request for Substantive Examination for UA a201203132 dated Apr. 15, 2013 (with English translation).
Request for Substantive Examination for ID W-00201201031 dated Jun. 3, 2013 (with English translation).
Notice of Acceptance (Notice of Allowance) for AU2009210098 dated Jun. 4, 2013.
"Amendment and Response to Office Action Under 37 C.F.R. § 1.111" submitted for U.S. Appl. No. 13/624,278, dated Jun. 28, 2013.
Notice of Allowance for CN Patent Application No. 200980103218.7 dated May 27, 2013 (with English translation).
Office Action for IL Application No. 195282 dated Apr. 10, 2013 (with English translation).
Notice of Allowance for U.S. Appl. No. 13/205,328 dated Jun. 10, 2013.
U.S. Appl. 13/923,858, filed Jun. 21, 2013.
Koyama et al., "Anti-tumor effect of E7080, a novel angiogenesis inhibitor", Folia Pharmacol. Jpn. 132, Therapeutic Agents Series (28), Molecular Target Drugs-1-1, p. 100-p. 104, Apr. 18, 2008.
Haiyi Jiang, "ZD6474: an Agent That Selectively Targets Both VEGFR Tyrosine Kinase and EGFR Tyrosine Kinase", Japanese Journal of Lung Cancer, vol. 46, No. 3, Jun. 20, 2006, p. 283-p. 288.
Stefan Frings, "New Molecular Targeted Therapeutic Drugs Clinical Results of Bevacizumab in Non-Small Cell Lung Cancer (NSCLC)", Japanese Journal of Lung Cancer, vol. 46, No. 3 ,Jun. 20, 2006 , p. 277-p. 281.
Lumi Chikahisa et al., "TSU-68 JDR/flk-inhibitor, can modulate the anti-tumor activity of paclitaxel by the induction of endothelial cell and tumor cell apoptosis", 61st Annual Meeting of Japanese Cancer Association, 2002, vol. 61, No. 1374, 2002, p. 443.
Office Action for JP2009-551518 dated Jun. 18, 2013 (with English translation).
The Argument and the Amendment for JP Patent Application No. 2008-532141 filed on Nov. 29, 2012 (with English translation).
The Argument and the Amendment for JP Patent Application No. 2008-556208 filed on Mar. 21, 2013 (with English translation).
The Argument and the Amendment for JP Patent Application No. 2008-516724 filed on Nov. 28, 2012 (with English translation ).
The Explanation of Circumstances Concerning Accelerated Examination and the Amendment filed on May 10, 2012 for JP Patent Application No. 2011-527665 (with English translation).
The Argument and the Amendment for JP Patent Application No. 2009-123432 filed on Jun. 12, 2012 (with English translation).
The Argument and the Amendment for JP Patent Application No. 2009-529019 filed on Jul. 3, 2012 (with English translation).
Response to Office Action for CN Application No. 200780017371.9 dated May 29, 2013 (with English translation).
Response to Office Action for U.S. Appl. No. 11/997,543, filed Jul. 3, 2013.
Office Action for JP Application No. 2009-540099 dated Jul. 2, 2013 (with English translation).
Notice of Allowance for CN Patent Application No. 201080030508.6 dated Jul. 4, 2013 (with English translation).
Notice of Allowance for JP Patent Application No. P2008-0556208 dated Jul. 9, 2013 (with English translation).
Matsui et al., "Extracellular matrix of linitis plastica as possible new therapeutic target", Surgical treatment 89(3):301-306 (Sep. 1, 20113) (with English translation).
Amendment for Application No. IL Patent Application No. 195282 dated Jul. 11, 2013 (with English translation).
Amended Claims for KR Patent Applicaton 10-2010-7011023 dated Jul. 17, 2013 (with English translation).
Communication for EP Patent Application No. 10809938.3 dated Jul. 19, 2013.
Notice of Allowance for U.S. Appl. No. 12/524,754 dated Jul. 19, 2013.
Notice of Allowance for EP Patent Application No. 10015141.4 dated Jul. 1, 2013.
Response to Office Action for IL Patent Application No. 217197 dated Jul. 31, 2013 (with English translation).
Response to Communication for EP Patent Application No. 08846814.5 dated Aug. 1, 2013.
Office Action for CN Patent Application No. 200780017371.9 dated Jul. 3, 2013 (with English translation).
Office Action for MX Patent Application No. MX/a/2012/002011 dated Jul. 17, 2013 (with English translation).
Amendment (amending specification) for AU Patent Application No. 2012246490 dated Aug. 2, 2013.
Response to Office Action for U.S. Appl. No. 11/997,719, filed Jul. 3, 2013.
Response to Office Action for EP Application No. 11798224.9 dated Aug. 2, 2013.
Nishio et al., "Phase 1 study of lenvatinib combined with carboplatin and paclitaxel in patients with non-small-cell lung cancer", British Journal of Cancer (2013), 109:538-544.
Amendment submitted for Korean Application No. 10-2008-7013685 dated Jul. 5, 2013 (with English translation).
Voluntary amendment for CA Patent Application No. 2704000 dated Aug. 6, 2013.
Amendment filed for JP Patent Application 2008-532141 dated Jul. 5, 2013 (with English translation).
Demand for Appeal Trial for JP Patent Application 2008-532141 dated Jul. 5, 2013 (with English translation).
Notice of Allowance for IL Patent Application No. 175363 dated Aug. 13, 2013 (with English translation).
Amendment filed for EP Application No. 12774278.1 dated Aug. 13, 2013.
Office Action for IL Patent Application No. 200090 dated Jul. 24, 2013 (with English translation).
Response to Office Action for U.S. Appl. No. 12/439,339 dated Aug. 22, 2013.
Communication to the Patent Office for CL Application No. 2012-00412 dated Aug. 31, 2012 (with English translation).

(56) References Cited

OTHER PUBLICATIONS

Communication to the Patent Office for AR Application No. P110100513 dated Aug. 27, 2013 (with English translation).
Notice of Allowance for U.S. Appl. No. 12/741,682 dated Jun. 19, 2013.
Office Action for U.S. Appl. No. 13/238,085 dated Sep. 6, 2013.
Corrected English Translation for Office Action for JP Patent Application No. 2007-529565 dated Aug. 7, 2012.
Response to Office Action for MX Patent Application No. MX/a/2012/002011 dated Aug. 29, 2013 (with English Translation).
Final Office Action for U.S. Appl. No. 12/039,381 dated Sep. 12, 2013.
Preliminary Amendment for U.S. Appl. No. 14/002,018 filed Aug. 28, 2013.
Amended Claims for RU Patent Application No. 2013140169 dated Aug. 29, 2013 (with English translation).
Notice of Allowance for CN Application No. 200880115011.7 dated Aug. 5, 2013 (with English translation).
Amendment filed for JP Patent Application No. 2009-551518 dated Aug. 6, 2013 (with English translation).
Argument filed for JP Patent Application No. 2009-551518 dated Aug. 6, 2013 (partial English translation).
Response to Office Action for CA Patent Application No. 2652442 dated Sep. 5, 2013.
Amendment to claims for IN Patent Application No. 7026/CHENP/2013 dated Sep. 5, 2013.
Amendment filed for JP Patent Application No. 2009-540099 dated Aug. 13, 2013 (with English translation).
Argument filed for JP Patent Application No. 2009-540099 dated Aug. 13, 2013 (with partial English translation).
Preliminary Amendment filed for U.S. Appl. No. 13/805,826 dated Sep. 9, 2013.
Request for Continued Examination and Information Disclosure Statement for U.S. Appl. No. 13/205,328 dated Sep. 10, 2013.
Notice of Allowance for JP Patent Application No. P2008-532141 dated Sep. 10, 2013 (with English translation).
Amendments for Cn Patent Application No. 201280010898.X dated Aug. 29, 2013 (with English translation).
Notice of Allowance for U.S. Appl. No. 13/624,278 dated Sep. 16, 2013.
Notice of Allowance for EP Patent Application No. 04818213.3 dated Sep. 19, 2013.
Request for Continued Examination and Information Disclosure Statment for U.S. Appl. No. 12/741,682, filed Sep. 19, 2013.
Amendment of Specification for AU Patent Application No. 2011270165 dated Sep. 23, 2013.
Office Action for PH Application No. 1-2011-502441 dated Oct. 1, 2013.
Amendment for IN Patent Application No. 10502/CHENP/2012 dated Oct. 1, 2013.
Response to Opposition for CL Patent Application No. 2012-00412 dated Oct. 2, 2013 (with English translation).
Office Action for KR 10-2008-7029472 dated Sep. 30, 2013 (in Korean).
Office Action for KR 10-2008-7029472 dated Sep. 30, 2013 (with English translation).
Ezzat et al., "Dual Inhibition of RET and FGFR4 Restraints Medullary Thyroid Cancer Cell Growth", Clinical Cancer Research, 11:1336-1341 (2005).
Sattler et al., "Targeting c-Kit mutations: basic science to novel therapies", Leukemia Research, 28S1:S11-S20 (2004).
Office Action for KR 10-2009-7005657 dated Sep. 30, 2013 (with English translation).
Office Action for KR 10-2009-7005657 dated Sep. 30, 2013 (in Korean).
Notice of Allowance for U.S. Appl. No. 13/205,328 dated Oct. 3, 2013.
Response to Restriction Requirement for U.S. Appl. No. 13/238,085 filed Oct. 4, 2013.
Amendment for KR Patent Application No. 10-2012-7033886 dated Sep. 27, 2013 (with English translation).
Office Action for U.S. Appl. No. 11/997,543 dated Sep. 30, 2013.
Office Action for CO Patent Application No. 12/022,608 dated Oct. 7, 2013 (with English translation).
Amendment for IL Patent Application No. 200090 dated Oct. 2, 2013 in English.
St. Bernard et al., "Fibroblast Growth Factor Receptors as Molecular Targets in Thyroid Carcinoma", Endocrinology, 146(3):1145-1153 (2005).
Amendment filed for CA Patent Application No. 2828946 dated Aug. 30, 2013.
Notice of Allowance for U.S. Appl. No. 11/997,719 dated Sep. 13, 2013.
Amendment filed for RU Patent Application No. 2012158142 dated Oct. 17, 2013.
Amendment filed for MX Patent Application No. MX/a/2012/014776 dated Oct. 21, 2013.
Office Action for IN Application No. 6415/CHENP/2008 dated Oct. 3, 2013.
Request for Re-examination for CN Patent Application No. 200780017371.9 dated Oct. 11, 2013 (with English translation).
Office Action for MX Patent Application No. MX/a/2010/008187 dated Aug. 21, 2013.
RCE filed for U.S. Appl. No. 12/524,754, filed Oct. 18, 2013.
Request for Examination and Voluntary Amendment for CA Patent Application No. 2713930 dated Oct. 21, 2013.
Notice of Allowance for U.S. Appl. No. 12/741,682 dated Oct. 21, 2013.
Response to Office Action for IN Application No. 1571/CHENP/2007 dated Oct. 30, 2013.
Request for Continued Examination and Response to Final Office Action for U.S. Appl. No. 12/039,381 dated Oct. 23, 2013.
Response to Office Action for MX Patent Application No. MX/a/2010/008187 dated Nov. 4, 2013 (with English Translation).
Almarsson et al., "High-Throughput Surveys of Cyrstal Form Diversity of Highly Polymorphic Pharmaceutical Compounds", Crystal Growth & Design, pp. 927-933 (2003).
Amendment filed for EP Application No. 12793322.4 dated Nov. 28, 2013.
Amendment filed for KR Patent Application No. 10-2008-7029472 dated Nov. 20, 2013 (with English translation).
Amendment for BR Patent Application No. 112012032462-4 dated Nov. 4, 2013 (with English translation).
Amendment for CO Application No. 12-022608 dated Jan. 28, 2014 (with English translation).
Amendment for IN Patent Application No. 1571/CHENP/2007 dated Jan. 23, 2014.
Amendment for KR Patent Application No. 10-2013-7020616 dated Nov. 22, 2013 (with English translation).
Amendment to Specification for KR Patent Application No. 10-2009-7017694 dated Feb. 28, 2014 (with English translation).
Argument for KR Patent Application No. 10-2009-7017694 dated Feb. 28, 2014 (with English translation).
Decision of Patent Grant for KR Patent Application No. 10-2008-7013685 dated Nov. 29, 2013 with English translation.
European Search Report for EP 11798224.9 dated Mar. 4, 2014.
International Preliminary Report (IPRP) for PCT/US2012/040183 dated Apr. 3, 2014.
IPRP for PCT/JP2012/060279 dated Oct. 31, 2013.
IPRP of International Patent Application No. PCT-JP2012-062509 dated Nov. 28, 2013.
Notice of Allowance for IL Patent Application No. 200090 dated Nov. 18, 2013 (with English translation).
Notice of Allowance for JP Patent Application No. P2009-551518 dated Oct. 22, 2013 (with English translation).
Notice of Allowance for U.S. Appl. No. 12/439,339 dated Apr. 1, 2014.
Notice of Allowance for U.S. Appl. No. 12/439,339 dated Nov. 7, 2013.
Notice of Allowance for U.S. Appl. No. 12/524,754 dated Nov. 22, 2013.

(56) References Cited

OTHER PUBLICATIONS

Notice of Allowance for U.S. Appl. No. 13/205,328 dated Jan. 30, 2014.
Notice of Allowance for U.S. Appl. No. 12/741,682 dated Feb. 7, 2014.
Notice of Allowance for U.S. Appl. No. 12/524,754 dated Feb. 13, 2014.
Office Action for CA Application No. 2676796 dated Dec. 30, 2013.
Office Action for CA Patent Application No. 2652442 dated Oct. 4, 2013.
Office Action for CN Application No. 200680020317.5 dated Mar. 4, 2014 (with English translation).
Office Action for CN Application No. 201180030568.2 dated Mar. 24, 2014 (with English translation).
Office Action for CN Patent Application No. 200680020317.5 dated Nov. 28, 2013 dated Nov. 28, 2013 (with English translation).
Office Action for CN Patent Application No. 201180030568.2 dated Oct. 12, 2013 (with English translation).
Office Action for EP Application No. 04807580.8 dated Mar. 18, 2014.
Office Action for European Patent Application No. 08704376.6 dated Feb. 24, 2014.
Office Action for IL Patent Application No. 205512 dated Oct. 28, 2013 (with English translation).
Office Action for IN Patent Application No. 1571/CHENP/2007 dated Oct. 23, 2013.
Office Action for IN Patent Application No. 1571/CHENP/2007 dated Dec. 9, 2013.
Office Action for JP Application No. P2009-540099 dated Mar. 25, 2014 (with English translation).
Office Action for KR Application No. 10-2008-7029472 dated Mar. 28, 2014 (with English translation).
Office Action for KR Application No. 10-2009-7005657 dated Mar. 28, 2014 (with English translation).
Office Action for KR Application No. 10-2009-7017694 dated Jan. 29, 2014 (with English translation).
Office Action for MX Patent Application No. MX/a/2012/002011 dated Nov. 21, 2013 (with English translation).
Office Action for PH Application No. 1-2011-502441 dated Feb. 19, 2014.
Office Action for U.S. Appl. No. 12/039,381 dated Jan. 9, 2014.
Office Action for U.S. Appl. No. 13/238,085 dated Nov. 12, 2013.
Office Action for U.S. Appl. No. 13/805,826 dated Apr. 2, 2014.
Office Action for U.S. Appl. No. 13/923,858 dated Apr. 18, 2014.
Office Action for U.S. Appl. No. 14/002,018 dated Apr. 14, 2014.
Office Action for U.S. Appl. No. 11/997,543 dated Mar. 11, 2014.
Office Action for U.S. Appl. No. 11/662,425 dated Feb. 27, 2014.
Office Action for VN Application No. 1-2011-03484 dated Dec. 31, 2013 (with English translation).
Office Action of CO Patent Application No. 12-022608 Dec. 17, 2013 (with English translation).
Office Action of IL Patent Application No. 207089 dated Nov. 25, 2013 (with English translation).
Office Action of MX Patent Application No. MX-a-2010-008187 dated Dec. 5, 2013 (with English translation).
O'Reilly et al., "Hydrolysis of tert-Butyl Methyl Ether(MTBE) in Dilute-Aqueous Acid", Environ.Sci.Technol; 35, 2001, p. 3954-p. 3961.
Patel et al., "The effect of excipients on the stability of levothyroxine sodium pentahydrate tables", International Journal of Pharmaceutics; 264, p. 35-p. 43 (2003).
Preliminary Amendment filed for U.S. Appl. No. 14/122,339 dated Nov. 26, 2013.
Preliminary Amendment filed for EP Patent Application No. 12786619.2 dated Nov. 13, 2013.
Preliminary Amendment filed for U.S. Appl. No. 14/117,276 filed Nov. 12, 2013.
RCE filed for U.S. Appl. No. 13-205328 dated Dec. 30, 2013.
Request for Continued Examination filed for U.S. Appl. No. 11/997,719 dated Dec. 11, 2013.
Request for Continued Examination filed for U.S. Appl. No. 13/624,278 dated Dec. 13, 2013.
Request for Continued Examination for U.S. Appl. No. 12/439,339 dated Jan. 27, 2014.
Request for Continued Examination for U.S. Appl. No. 12/741,682 dated Jan. 17, 2014.
Request for Continued Examination for U.S. Appl. No. 12/524,754 dated Feb. 3, 2014.
Response filed for IN Patent Application No. 6415/CHENP/2008 dated Jan. 17, 2014.
Response filed for KR Application No. 10-2009-7005657 dated Nov. 21, 2013 (with English translation).
Response to CN Application No. 201180030568.2 dated Jan. 13, 2014 (with English translation).
Response to Office Action and Information Disclosure Statement filed for U.S. Appl. No. 11/997,543 dated Dec. 19, 2013.
Response to Office Action for CA Patent Application No. 2652442 dated Jan. 8, 2014.
Response to Office Action for CN 2006800203175 filed on Jan. 9, 2014 (with English translation).
Response to Office Action for CO Patent Application No. 12-022608 dated Nov. 13, 2013 (with English translation).
Response to Office Action for MX Patent Application No. MX/a/2010008187 dated Feb. 17, 2014 (with English translation).
Response to Office Action for MX-a-2012-002011 dated Jan. 16, 2014 (with English translation).
Response to Office Action for PH Application No. 1-2011-502441 dated Nov. 4, 2013.
Response to Office Action for Philippines Patent Application No. 1-2011-502441 dated Feb. 28, 2014.
Response to Office Action for U.S. Appl. No. 12/039,381 dated Apr. 3, 2014.
Search Report for EP Patent Application No. 11798224.9 dated Mar. 21, 2014.
Stahl and Wermuth, Handbook of Pharmaceutical Salts: Properties, Selection and Use, pp. 117-122 (2002).
Submission for VN Application No. 1-2011-03484 dated Feb. 28, 2014 (with English translation).
Voluntary amendment filed for CA Patent Application No. 2802644 dated Nov. 22, 2013.
Wang, Y., "Drugs of Today, Everolimus in renal cell carcinoma", Journals of the Web, 46(8): Abstract, Aug. 2010.
Winkler et al., "Kinetics of vascular normalization by VEGFR2 blockade governs brain tumor response to radiation: Role of oxygenation, angiopoietin-1, and matrix metalloproteinases", Cancer Cell vol. 6:553-563 (2004).
Xiaotian Zhang et al. "Synergic antiproliferative effect of DNA methyltransferase inhibitor in combination with anticancer drugs in gastric carcinoma", Cancer Science, vol. 97, No. 9, Sep. 2006, p. 938-p. 944.
Amendment for U.S. Appl. No. 11/662,425 dated Sep. 2, 2014.
Anderson et al, "Clinical, Safety, and Economic Evidence in Radioactive Iodine-Refractory Differentiated Thyroid Cancer: A Systematic Literature Review", Thyroid, volurne.23, No. 4, 2013, p. 392-p. 407.
Associate's comments about the Board of Appeal for EP Patent Application No. 04807580.8 dated Jul. 7, 2014.
Besson et al., "PTEN/MMAC1/TEP1 in signal transduction and tumorigenesis", European Journal of Biochemistry, 263:605-611 (1999).
Brose et al, "Sorafenib in radioactive iodine-refractory, locally advanced or metastatic differentiated thyroid cancer: a randomised, double-blind, phase 3 trial", The lancet, vol. 384, Jul. 26, 2014, p. 319-p. 328.
Dankort et al., "Braf$^{V600E}$ cooperates with *Pten* loss to induce metastatic melanoma", Nature Genetics, 41(5):544-552 (2009).
Davies et al., "Mutations of the BRAF gene in human cancer", Nature 417:949-954 (2002).
Elisei et al, "Subgroup Analyses of a Phase 3 -Mul Ticenter, Double-Blind, Placebo-Controlled Trial of Lenvatinib (E7080) in Patients With $^{131}$I-Refractory Differentiated Thyroid Cancer", 111e Poster, No. 1033P, presented at the European Society for Medical Oncology 2014, Congress, Sep. 26-30, 2014.

(56) References Cited

OTHER PUBLICATIONS

Erdem et al, "Correlation of E-cadherin, VEGF, COX-2 expression to prognostic parameters in papillary thyroid carcinoma", Experimental and Molecular Pathology, No. 90, Feb. 16, 2011, p. 312-p. 317.
European Search Report for EP 09705712.9 dated Aug. 7, 2014.
European Search Report for EP Patent Application No. 12774278.1 dated Aug. 14, 2014.
Final Office Action for U.S. Appl. No. 12/039,381 dated May 29, 2014.
Finn et al., "A multicenter, open-label, phase 3 trial to compare the efficacy and safety of lenvatinib (E7080) versus sorafenib in first-line treatment of subjects with unresectable hepatocellular carcinoma.", American Society of Clinical Oncology, Annual Meeting Abstract, May 31, 2014.
Fuji et al., Angiogenesis Inhibitor/Kekkan Shinsei Sogaiyaku, Clinical Gastroenterology, 19:220-227 (2004) (with English translation).
Gild et al, "Multikinase inhibitors: a new option for the treatment of thyroid cancer", Nature Reviews Endocrinology, vol. 7, Oct. 2011, p. 617-p. 624.
Havel et al., "E7080 (lenvatinib) in addition to best supportive care (BSC) versus BSC alone in third-line or greater nonsquamous, non-small cell lung cancer (NSCLC).", American Society of Clinical Oncology, Annual Meeting Abstract, May 31, 2014.
Ikuta et al., "E7080, a Multi-Tyrosine Kinase Inhibitor, Suppresses the Progression of Malignant Pleural Mesothelioma with Different Proangiogenic Cytokine Production Profiles", Clinical Cancer Research, 15(23):7229-7237 (2009).
Kremer, "Lenvatinib Advisory Board", The presentation document, American Society of Clinical Oncology, Annual meeting 2014, May 31, 2014.
Matsui et al., "Mechanism of antitumor activity of E70780, a selective VEGFR and FGFR tyrosine kinase inhibitor (TKI), in combination with selective mutant BRAF inhibition", Journal of Clinical Oncology, 29(15) (2011).
Matsui et al., "Multi-Kinase" Inhibitor E7080 Suppresses Lymph Node and Lung Metastases of Human Mammary Breast Tumor MDA-MB-231 via Inhibition of Vascular Endothelial Growth Factor•Receptor (VEGF-R) 2 and VEGF-R3 Kinase, Clinical Cancer Research, 14:459-465 (2008).
Nakagawa et al., E7050:A dual c-Met and VEGFR-2 tyrosine kinase inhibitor promotes tumor regression and prolongs survival in mouse xenograft models, Cancer Science 101(1):210-215 (2009).
Nakazawa et al., "Miximizing the efficacy of anti-angiogenesis cancer therapy: A multi-targeting strategy by tyrosine kinase inhibitors", Abstract No. 2980 Hall E-E, Poster Section 2 printed May 13, 2014.
Nakazawa et al., "Miximizing the efficacy of anti-angiogenesis cancer therapy: A multi-targeting strategy by tyrosine kinase inhibitors", AACR Annual Meeting, Abstract, Apr. 5-9, 2014.
Nakazawa, "Combination strategy of lenvatinib: Maximizing its anti-angiogenesis efficacy", Tsukuba Research Laboratory, Eisai Co., Ltd., Ibaraki, Japan, Jun. 27, 2014.
Notice of Allowance for KR Patent Application No. 10-2008-7029472 dated Sep. 16, 2014 (withEnglish translation).
Notice of Allowance for U.S. Appl. No. 13/624,278 dated Jun. 25, 2014.
Notice of Allowance for CA Application No. 2652442 dated Apr. 16, 2014.
Notice of Allowance for CN Application No. 201180030568.2 dated Sep. 9, 2014 (with English translation).
Notice of Allowance for EP Patent Application No. 08704376.6 dated Aug. 19, 2014.
Notice of Allowance for Israel Patent Application No. 195282 dated Aug. 11, 2014.
Notice of allowance for Korean Patent Application No. 10-2009-7017694 dated Jul. 28, 2014 (with English translation).
Notice of Allowance for KR Patent Application No. 10-2009-7005657 dated Sep. 19, 2014 (with English translation).
Notice of Allowance for Mexican Patent Application MX/a/2010/008187 dated Jul. 17, 2014 (with English translation).
Notice of Allowance for U.S. Appl. No. 11/997,719 dated Jun. 5, 2014.
Notice of Allowance for U.S. Appl. No. 12/524,754 dated Sep. 18, 2014.
Notice of Allowance for U.S. Appl. No. 12/741,682 dated May 15, 2014.
Notice of Allowance for U.S. Appl. No. 13/205,328 dated May 8, 2014.
Notice of Allowance for UA Patent Application No. a201203132 dated Mar. 21, 2014 (with English translation).
Notice of Allowance for VN Application No. 1-2011-03484 dated Apr. 28, 2014 (with English translation).
Office Action for MX/a/2012/014776 dated Apr. 4, 2014 (with English translation).
Office Action for AU Patent Application No. 2010285740 dated Aug. 22, 2014.
Office Action for CA Patent Application No. 2771403 dated Jul. 16, 2014.
Office Action for CN Patent Application No. 201280010898.X dated Aug. 11, 2014 (with English translation).
Office Action for EP Application No. 03791389.4 dated Jun. 10, 2014.
Office Action for EP Application No. 08846814.5 dated Jun. 4, 2014.
Office Action for EP Patent Application No. 07743994.1 dated Sep. 9, 2014.
Office Action for KR Patent Application No. 10-2010-7011023 dated Sep. 3, 2014 (with English translation).
Office Action for MX Application No. MX/a/2010/008187 dated Apr. 28, 2014 (with English translation).
Office Action for MX Application No. MX/a/2012/002011 dated Apr. 28, 2014 (with English translation).
Office Action for RU Application No. 2012103471 dated May 20, 2014 (with English translation).
Office Action for U.S. Appl. No. 11/662,425 dated Jun. 5, 2014.
Office Action for U.S. Appl. No. 11/662,425 dated Sep. 17, 2014.
Office Action for U.S. Appl. No. 12/864,817 dated Aug. 15, 2014.
Office Action for U.S. Appl. No. 13/805,826 dated Jul. 1, 2014.
Office Action for U.S. Appl. No. 13/805,826 dated Sep. 23, 2014.
Office Action for U.S. Appl. No. 14/002,018 dated Jul. 25, 2014.
Office Action for U.S. Appl. No. 14/002,018 dated Jun. 9, 2014.
Official Notification for EP 04807580.8 dated Jun. 16, 2014.
Official Notification for EP 04807580.8 dated Jun. 27, 2014.
Pacini, "38th Annual Meeting of the European Thyroid Association", European Thyroid Association, Santiago de Compostela, Spain, Aug. 15, 2014, p. 73-p. 226.
Request for Continued Examination filed for U.S. Appl. No. 12/741,682 dated May 6, 2014.
Request for Continued Examination for U.S. Appl. No. 13/205,328 dated Apr. 28, 2014.
Request for Continued Examination for U.S. Appl. No. 11/997,719 dated Aug. 29, 2014.
Request for Continued Examination for U.S. Appl. No. 12/741,682 dated Aug. 14, 2014.
Request for Continued Examination for U.S. Appl. No. 12/524,754 dated May 13, 2014.
Response filed for EP Patent Application No. 04807580.8 dated May 16, 2014.
Response filed for KR Patent Application No. 10-2008-7029472 dated May 1, 2014 (with English translation).
Response filed for KR Patent Application No. 10-2009-7005657 dated May 7, 2014 (with English translation).
Response filed for SG Patent Application No. 201108602-2 dated May 22, 2014.
Response to Office Action for U.S. Appl. No. 13/923,858 dated Aug. 8, 2014.
Response to Office Action for CA Patent Application No. 2771403 dated Sep. 10, 2014.
Response to Office Action for CN Application No. 201180030568.2 dated May 14, 2014 (with English translation).
Response to Office Action for EP Application No. 08704376.6 dated Apr. 30, 2014.
Response to Office Action for JP2009-540099 dated Apr. 28, 2014, (with English translation).

(56) References Cited

OTHER PUBLICATIONS

Response to Office Action for U.S. Appl. No. 11/662,425 dated May 20, 2014.
Response to Office Action for U.S. Appl. No. 14/002,018 dated May 28, 2014.
Response to Office Action for U.S. Appl. No. 14/002,018 dated Jul. 18, 2014.
Robinson et al, "Characterization of Tumor Size Changes Over Time From the Phase 3 Study of (E7080) Lenvatinib in Differentiated Cancer of the Thyroid (Select)", The Poster, No. 1031P, presented at the European Society for Medical Oncology 2014 Congress, Sep. 26-30, 2014.
Schlumberger et al., "A phase 3, multicenter, double-blind, placebo•controlled trial of lenvatinib (E7080) in patients with 131I refractory differentiated thyroid cancer (SELECT).", American Society of Clinical Oncology, Annual Meeting Abstract, Jun. 2, 2014.
Sennino and Donald M. McDonald, "Controlling escape from angiogenesis inhibitors", Nature Reviews Cancer, vol. 12, Oct. 2012, p. 699-p. 709.
Shumaker et al., "Effect of lenvatinib (E7080) on the QTc interval: results from a thorough QT study in healthy volunteers", Cancer Chemother Pharmacol, Springer-Verlag Berlin Heidelberg (2014) (online).
Søndergaard et al., "Differential sensitivity of melanoma cell lines with BRAFV600E mutation to the specific Raf inhibitor PLX4032", Journal of Translational Medicine, Biomed, Central London, GB 8(1):39 (2010).
Submission for EP 04807580.8 dated Jun. 13, 2014.
Submission for EP 04807580.8 dated Jun. 16, 2014.
Submission of Document for CA Application No. 2676796 dated Jun. 27, 2014.
Submission of document for EP Patent Application No. 117982249 dated Sep. 19, 2014.
Submission of document for MX Application No. MX/a/2014/010594 dated Sep. 4, 2014 (with English translation).
Submission of Document for U.S. Appl. No. 13/205,328 dated Jul. 8, 2014.
Submission of documents (Notice of Appeal) for U.S. Appl. No. 12/039,381 dated Aug. 29, 2014.
Submission of documents (Notice of Appeal) for U.S. Appl. No. 11/662,425 dated Sep. 5, 2014.
Submission of documents for CL Patent Application No. 2012-00412 dated Aug. 12, 2014 (with English translation).
Submission of documents for EP Patent Application No. 03791389.4 dated Jul. 25, 2014.
Submission of Documents for EP Patent Application No. 08846814.5 dated Jul. 24, 2014.
Submission of Documents for Korean Patent Application No. 10-2012-7003846 dated Jun. 18, 2014 (with English translation).
Submission of Documents for MX Application No. MX/a/2010/008187 dated Jun. 25, 2014 (with English translation).
Submission of Documents for MX Application No. MX/a/2012/014776 dated Jun. 20, 2014 (with English translation).
Submission of Documents for MY Patent Application No. PI2011700172 dated Jul. 3, 2014 (in English).
Submission of Documents for RU Patent Application No. 2012103471 dated Jul. 21, 2014.
Submission of Documents for U.S. Appl. No. 13/805,826 dated Jun. 2, 2014.
Submission of Documents for U.S. Appl. No. 13/805,826 dated Aug. 8, 2014.
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at the European Society for Medical Oncology 2014 Congress, Sep. 26-30, 2014.
Tahara et al., "Lenvatinib in radioactive-iodine-refractory differentiated thyroid cancer. Results of the Phase 3 trial (SELECT trial ), 1-81-1, Abstract and Presentation Document", The 12th Annual Meeting of Japanese Society of Medical Oncology, Jul. 17, 2014.
Takahashi et al, "Phase II Study of Lenvatinib, A Multitargeted Tyrosine With All Idstologic Subtypes Of Advanced Thyroid Cancer (Differentiated, Medullary, and Anaplastic)", The Poster, presented at the European Society for Medical Oncology 2014 Congress, Sep. 26-30, 2014.
Tamura et al., "Molecular Characterization of Undifferentiated-Type Gastric Carcinoma", Laboratory Investigation, 81(4):593-598 (2001).
Tohyama et al., "Antitumor Activity of Lenvatinib (E7080): An Angiogenesis Inhibitor That Targets Multiple Receptor Tyrosine Kinases in Preclinical Human Thyroid Cancer Models", Journal of Thyroid Research, vol. 2014, Sep. 10, 2014, p. 1-p. 13.
Vergote et al., "Prognostic and predictive role of circulating angiopoietin-2 in multiple solid tumors; An analysis of approximately 500 patients treated with lenvatinib across tumor types.", American Society of Clinical Oncology, Annual Meeting Abstract, May 31, 2014.
Wells Jr et al, "Vandetanib in Patients With Locally Advanced or Metastatic Medullary Thyroid Cancer: A Randomized, Double-Blind Phase III Trial", Journal of Clinical Oncology, vol. 30, No. 2, Jan. 10, 2012, p. 134-p. 141, corrections published Aug. 20, 2013, p. 3049.
Wirth et al, "Treatment-Emergent Hypertension and Efficacy in the Phase 3 Study of (E7080) Lenvatinib in Differentiated Cancer of the Thyroid (SELECT)", The Poster, No. 1030P, presented at the European Society for Medical Oncology 2014 Congress, Sep. 26-30, 2014.
Yamori et al., Current Treatment of Solid Tumors New Approaches of Treatment, Drug Treatment Kinase Inhibitors/Kokeigan no Saishin Chiryo Chiryo no Aratana Torikumi Yakubutsu Ryoho Kinase Inhibitors, Japanese Journal of Clinical Medicine 68(6):1059-1066 (2010) (with English translation).
Yang et al., "RG7204(PLX4032), a Selective BRAFv600E Inhibitor, Displays Potent Antitumor Activity in Melanoma Models", Cancer Research 70(13):5518-5527 (2010).
Yokota, "ASCO report: Gastrointestinal Cancer field/ASCO Hokoku Shokakigan Ryoiki", Gan Bunshi Hyoteki Chiryo, 8(4):271-283 (2010) (with English translation).
Zhong et al., "Mechanisms underlying the synergistic effect of SU5416 and cisplatin on cytotoxicity in human ovarian tumor cells", International Journal of Oncology, 25(2):445-451 (2004).

* cited by examiner

(A)
Phosphorylated RET

RET

Control | Test substance 10mg/kg | Test substance 30mg/kg | Test substance 100mg/kg

(B)
Phosphorylated RET

RET 2 hours after oral administration 0 hours    2 hours    8 hours    12 hours    24 hours Oral administration at 100 mg test substance/kg

ANTITUMOR AGENT FOR THYROID CANCER

CROSS REFERENCE TO PRIOR RELATED APPLICATIONS

This application is a divisional of copending U.S. patent application Ser. No. 12/301,353 filed Nov. 18, 2008, which is a U.S. national phase application under 35 U.S.C. §371 of International Patent Application No. PCT/JP2007/060560, filed on May 17, 2007, and claims the benefit of U.S. Provisional Patent Application No. 60/747,570, filed on May 18, 2006. Each of those prior application is incorporated herein by reference and in its entirety. The International Application was published in Japanese on Nov. 29, 2007, as International Publication No. WO 2007/136103 A1 under PCT Article 21(2).

REFERENCE TO SEQUENCE LISTING

A Sequence Listing is submitted herewith, pursuant to 37 C.F.R. 1.821(c), as an ASCII compliant text file named "SequenceListing.txt", which was created on May 3, 2011 and has a size of 33,334 bytes. The content of the aforementioned "SequenceListing.txt" file is hereby incorporated by reference in its entirety.

FIELD OF THE INVENTION

The present invention relates to a therapeutic agent and a method containing a substance that inhibits RET kinase activity (hereinafter, also referred to as an "RET kinase inhibiting substance") for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, to use of an RET kinase inhibiting substance for producing said therapeutic agent and to an RET kinase inhibiting substance for said therapeutic agent.

The present invention also relates to a therapeutic agent and a method containing an RET kinase inhibiting substance for treating thyroid carcinoma, to use of an RET kinase inhibiting substance for producing said therapeutic agent and to an RET kinase inhibiting substance for said therapeutic agent.

Moreover, the present invention relates to a pharmaceutical composition containing an RET kinase inhibiting substance for administering to an organism having a cell expressing mutant RET, to a method for treating a disease including administration to an organism having a cell expressing mutant RET, to use of an RET kinase inhibiting substance for producing said pharmaceutical composition and to an RET kinase inhibiting substance for said pharmaceutical composition.

The present invention also relates to an RET kinase inhibitor.

Furthermore, the present invention relates to a method for predicting the effect of an RET kinase inhibiting substance on a patient using the presence or the absence of RET mutation in the cell as an indication.

BACKGROUND OF THE INVENTION

RET is one of the receptor tyrosine kinases and is a cell surface molecule that transduces signals for cell growth and differentiation.

RET mutation is known to be involved in diseases such as multiple endocrine neoplasia, type IIA, multiple endocrine neoplasia, type IIB, familial medullary thyroid carcinoma, sporadic medullary thyroid carcinoma, papillary thyroid carcinoma and Hirschsprung disease. (Oncogene, 19, 5590-5597, 2000; Cancer Research, 15, 7284-7290, 2002.) RET kinase inhibiting substance has been suggested as a potentially effective therapeutic agent for said diseases. (Oncogene, 19, 5590-5597, 2000; Cancer Research, 15, 7284-7290, 2002.)

Mutation of one of five cysteine residues at codons 609, 611, 618, 620 and 634 of RET is found in 93-98% of the patients with multiple endocrine neoplasia, type IIA, where mutation at RET codon 634 is found most frequently. (Cancer Research, 66, 1177-1180, 2006; Journal of Clinical Endocrinology and Metabolism, 88, 5438-5443, 2003.)

On the other hand, mutation M918T (mutation from methionine to tyrosine at codon 918) of RET is found in 95% of the patients with multiple endocrine neoplasia, type IIB. (Journal of Clinical Endocrinology and Metabolism, 88, 5438-5443, 2003.)

Mutation at one of RET codons 609, 611, 618, 620, 634, 768, 790, 791, 804 and 891 is found in many of the patients with familial medullary thyroid carcinoma, (Journal of Clinical Endocrinology and Metabolism, 88, 5438-5443, 2003.)

All of these point mutations are known to cause constant ligand-independent RET activation. (Cancer Research, 66, 1177-1180, 2006; Journal of Clinical Endocrinology and Metabolism, 88, 5438-5443, 2003.)

A syndrome of multiple endocrine neoplasia, type IIA is characterized by medullary thyroid carcinoma, pheochromocytoma and parathyroid hyperplasia whereas a syndrome of multiple endocrine neoplasia, type IIB is associated with medullary thyroid carcinoma, pheochromocytoma and mucosal neuromas of the gastrointestinal tract. Chief symptom of syndrome of familial medullary thyroid carcinoma is medullary thyroid carcinoma. (Journal of Clinical Endocrinology and Metabolism, 89, 4142-4145, 2004.)

Point mutation of RET somatic cells is found in about 40% of the patients with sporadic medullary thyroid carcinoma while mutations are mostly found at codon 918. (Journal of Clinical Endocrinology and Metabolism, 89, 5823-5827, 2004.)

Moreover, a fusion gene of RET gene and other gene, namely, rearrangement of RET gene, is found in papillary thyroid carcinoma due to chromosomal inversions or chromosomal translocation. The fusion protein generated via RET gene rearrangement is known to lead to ligand-independent dimerization and constant RET activation. (Endocrinology, 145, 5448-5451, 2004.)

Hirschsprung disease is characterized by persistent constipation and intestinal dilatation in newborns caused by abnormal colonic nerve plexus. One of the causes of Hirschsprung disease is known to be RET mutation, (Proceedings of the National Academy of Sciences of the United States of America, 102, 8949-8954, 2005.)

RET mutation has been reported to cause scaffold-independent proliferation and tumorigenesis in NIH3T3 cells. (Cancer Research, 15, 7284-7290, 2002.)

RET kinase inhibiting substance ZD6474 has been reported to suppress scaffold-independent proliferation in NIH3T3 cells transformed with mutant RET and inhibited tumor formation after infusion of said cells into nude mice. (Cancer Research, 15, 7284-7290, 2002.)

RET kinase inhibiting substance BAY 43-9006 has been reported to reduce the size of tumor in a model for subcutaneous transplantation of human medullary thyroid carcinoma cell line (TT). (Journal of the National Cancer Institute, 98, 326-334, 2006.)

Hence, RET kinase inhibiting substances are suggested to induce cell growth inhibition for cells expressing mutant RET and show antitumor effect against these tumor cells. RET kinase inhibiting substances also appear to be effective against diseases caused by RET mutation.

Thus, RET kinase inhibiting substances are expected to be effective against multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia, mucosal neuromas of the gastrointestinal tract and thyroid carcinoma.

4-(3-chloro-4-(cyclopropyl aminocarbonyl)aminophenoxy)-7-methoxy-6-quinolinecarboxamide and analogs thereof are known as angiogenesis inhibiting substances. (International Publication No. 02/32872, pamphlet; International Publication No. 2004/080462, pamphlet; International Publication No. 2005/063713, pamphlet.) However, none has reported as to what 4-(3-chloro-4-(cyclopropylaminocarbonyl)aminophenoxy)-7-methoxy-6-quinolinecarboxamide and analogs thereof have RET kinase-inhibiting activity.

SUMMARY OF THE INVENTION

The present invention was achieved regarding the circumstances described above and the problems to be solved by the invention are to provide a therapeutic agent and a method for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract as well as thyroid carcinoma, and to provide a pharmaceutical composition and a therapeutic method highly effective for organisms including cells expressing mutant RET. Another problem to be solved by the invention is to provide an RET kinase inhibitor. Yet another problem to be solved by the invention is to provide a method for predicting the effect of 4-(3-chloro-4-(cyclopropylaminocarbonyl)aminophenoxy)-7-methoxy-6-quinolinecarboxamide and analogs thereof.

In order to solve the above-mentioned problems, the present inventors have gone through keen research and found that 4-(3-chloro-4-(cyclopropylaminocarbonyl)aminophenoxy)-7-methoxy-6-quinolinecarboxamide has RET kinase-inhibiting activity and that 4-(3-chloro-4-(cyclopropylaminocarbonyl)aminophenoxy)-7-methoxy-6-quinolinecarboxamide and analogs thereof are highly effective against at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract as well as thyroid carcinoma. The present inventors have also found that 4-(3-chloro-4-(cyclopropylaminocarbonyl) aminophenoxy)-7-methoxy-6-quinolinecarboxamide and analogs thereof are highly effective for organisms including cells expressing mutant RET and further found that the effect of 4-(3-chloro-4-(cyclopropylaminocarbonyl)aminophenoxy)-7-methoxy-6-quinolinecarboxamide and analogs thereof can be predicted using the presence or the absence of RET mutation in the cell as an indication.

Thus, the present invention relates to a therapeutic agent containing an RET kinase inhibiting substance for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It also relates to a therapeutic agent for treating thyroid carcinoma, containing an RET kinase inhibiting substance.

It further relates to a pharmaceutical composition containing an RET kinase inhibiting substance for administering to an organism containing a cell expressing mutant RET.

It further relates to a method for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, the method including administering an effective amount of an RET kinase inhibiting substance to a patient.

It further relates to a method for treating thyroid carcinoma, including administering an effective amount of an RET kinase inhibiting substance to a patient.

It further relates to a method for treating a disease, including administering an effective amount of an RET kinase inhibiting substance to an organism containing a cell expressing mutant RET.

It further relates to use of an RET kinase inhibiting substance for producing a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It further relates to use of an RET kinase inhibiting substance for producing a therapeutic agent for treating thyroid carcinoma.

It further relates to use of an RET kinase inhibiting substance for producing a pharmaceutical composition containing the RET kinase inhibiting substance, for administering to an organism containing a cell expressing mutant RET.

It further relates to an RET kinase inhibiting substance for a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It further relates to an RET kinase inhibiting substance for a therapeutic agent for treating thyroid carcinoma.

It further relates to an RET kinase inhibiting substance for a pharmaceutical composition containing the RET kinase inhibiting substance, for administering to an organism containing a cell expressing mutant RET.

It further relates to a method for predicting whether a patient is highly sensitive to an RET kinase inhibiting substance, including using the presence or the absence of RET mutation in the cell as an indication.

It further relates to a method for analyzing sensitivity of a cell to an RET kinase inhibiting substance, including determining the presence or the absence of RET mutation in the cell.

It further relates to a method for selecting a cell highly sensitive to an RET kinase inhibiting substance, including determining the presence or the absence of RET mutation in the cell.

It further relates to a method for selecting a patient highly sensitive to an RET kinase inhibiting substance, including determining the presence or the absence of RET mutation in the cell.

It further relates to a method for classifying a patient according to the result obtained from an analysis of sensitivity of the patient to an RET kinase inhibiting substance, including determining the presence or the absence of RET mutation in the cell.

It further relates to a method for selecting a patient intended for administration of an RET kinase inhibiting substance, including determining the presence or the absence of RET mutation in the cell, and selecting a patient containing a cell expressing mutant RET from the determination results.

It further relates to a method for predicting a therapeutic effect of an RET kinase inhibiting substance on a patient, including determining the presence or the absence of RET mutation in a cell.

It further relates to a method for determining the presence or the absence of RET mutation in the cell from a patient for predicting the sensitivity of the patient to an RET kinase inhibiting substance.

Said RET kinase inhibiting substance may be a compound represented by General Formula (I)

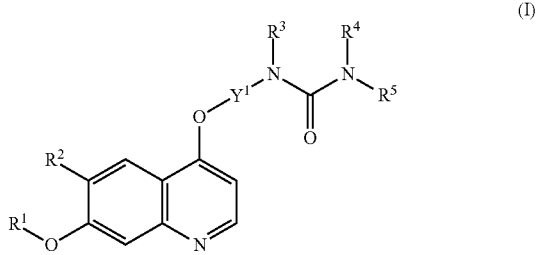

[wherein, $R^1$ represents a group represented by Formula —$V^1$—$V^2$—$V^3$ (wherein, $V^1$ represents $C_{1-6}$ alkylene group that may have a substituent; $V^2$ represents a single bond, an oxygen atom, a sulfur atom, carbonyl group, sulfinyl group, sulfonyl group, group represented by Formula —$CONR^6$—, group represented by Formula —$SO_2NR^6$—, group represented by Formula —$NR^6SO_2$—, group represented by Formula —$NR^6CO$— or group represented by Formula —$NR^6$— (wherein, $R^6$ represents a hydrogen atom, $C_{1-6}$ alkyl group that may have a substituent or $C_{3-8}$ cycloalkyl group that may have a substituent); $V^3$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent);

$R^2$ represents cyano group, $C_{1-6}$ alkoxy group that may have a substituent, carboxyl group, $C_{2-7}$ alkoxycarbonyl group that may have a substituent or group represented by Formula —$CONV^{a11}V^{a12}$ (wherein, $V^{a11}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent; $V^{a12}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent, 3-10-membered non-aromatic heterocyclic group that may have a substituent, hydroxyl group, $C_{1-6}$ alkoxy group that may have a substituent or $C_{3-8}$ cycloalkoxy group that may have a substituent);

$Y^1$ represents a group represented by Formula

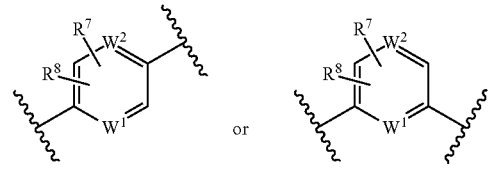

(wherein, $R^7$ and $R^8$ each independently represent a hydrogen atom, a halogen atom, cyano group, nitro group, amino group, $C_{1-6}$ alkyl group that may have a substituent, $C_{3-8}$ cycloalkyl group that may have a substituent, $C_{1-6}$ alkoxy group that may have a substituent, $C_{1-6}$ alkylthio group that may have a substituent, formyl group, $C_{2-7}$ acyl group that may have a substituent, $C_{2-7}$ alkoxycarbonyl group that may have a substituent or group represented by Formula —$CONV^{d1}V^{d2}$ (wherein, $V^{d1}$ and $V^{d2}$ each independently represent a hydrogen atom or $C_{1-6}$ alkyl group that may have a substituent);

$W^1$ and $W^2$ each independently represent a carbon atom or a nitrogen atom that may have a substituent);

$R^3$ and $R^4$ each independently represent a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{2-7}$ acyl group that may have a substituent or $C_{2-7}$ alkoxycarbonyl group that may have a substituent; and $R^5$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent], a pharmacologically acceptable salt thereof or a solvate thereof.

Moreover, the RET kinase inhibiting substance may be at least one compound selected from 5-(5-fluoro-2-oxo-1,2-dihydroindole-3-ylidenemethyl)-2,4-dimethyl-1H-pyrrole-3-carboxylic acid (2-diethylaminoethyl)amide, N-{2-chloro-4-[(6,7-dimethoxy-4-quinolyl)oxy]phenyl}-N'-(5-methyl-3-isoxazolyl)urea and 4-[(4-fluoro-2-methylindole-5-yl)oxy]-6-methoxy-7-[3-(pyrrolidine-1-yl)propoxy]quinazoline, a pharmacologically acceptable salt thereof or a solvate thereof.

The present invention further relates to an RET kinase inhibitor containing the compound represented by General Formula (I), a pharmacologically acceptable salt thereof or a solvate thereof.

It further relates to an RET kinase inhibitor containing at least one compound selected from 5-(5-fluoro-2-oxo-1,2-dihydroindole-3-ylidenemethyl)-2,4-dimethyl-1H-pyrrole-3-carboxylic acid(2-diethylaminoethyl)amide, N-{2-chloro-4-[(6,7-dimethoxy-4-quinolyl)oxy]phenyl}-N'-(5-methyl-3-isoxazolyl)urea and 4-[(4-fluoro-2-methylindole-5-yl)oxy]-6-methoxy-7-[3-(pyrrolidine-1-yl)propoxy]quinazoline, a pharmacologically acceptable salt thereof or a solvate thereof.

The present invention also relates to a therapeutic agent containing 4-(3-chloro-4-(cyclopropylaminocarbonyl)aminophenoxy)-7-methoxy-6-quinolinecarboxamide, a pharmacologically acceptable salt thereof or a solvate thereof for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It further relates to a therapeutic agent containing 4-(3-chloro-4-(cyclopropylaminocarbonyl)aminophenoxy)-7-methoxy-6-quinolinecarboxamide, a pharmacologically acceptable salt thereof or a solvate thereof for treating thyroid carcinoma.

It further relates to a pharmaceutical composition containing 4-(3-chloro-4-(cyclopropylaminocarbonyl)aminophenoxy)-7-methoxy-6-quinolinecarboxamide, a pharmacologically acceptable salt thereof or a solvate thereof for administering to an organism containing a cell expressing mutant RET.

It further relates to a method for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, the method including administering an effective amount of 4-(3-chloro-4-(cyclopropylaminocarbonyl)aminophenoxy)-7-methoxy-6-quinolinecarboxamide, a pharmacologically acceptable salt thereof or a solvate thereof to a patient.

It further relates to a method for treating thyroid carcinoma, including administering an effective amount of 4-(3-chloro-4-(cyclopropylaminocarbonyl)aminophenoxy)-7-methoxy-6-quinolinecarboxamide, a pharmacologically acceptable salt thereof or a solvate thereof to a patient.

It further relates to a method for treating a disease, including administering an effective amount of 4-(3-chloro-4-(cyclopropylaminocarbonyl)aminophenoxy)-7-methoxy-6-quinolinecarboxamide, a pharmacologically acceptable salt thereof or a solvate thereof to an organism containing a cell expressing mutant RET.

It further relates to use of 4-(3-chloro-4-(cyclopropylaminocarbonyl)aminophenoxy)-7-methoxy-6-quinolinecarboxamide, a pharmacologically acceptable salt thereof or a solvate thereof for producing a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It further relates to use of 4-(3-chloro-4-(cyclopropylaminocarbonyl)aminophenoxy)-7-methoxy-6-quinolinecarboxamide, a pharmacologically acceptable salt thereof or a solvate thereof for producing a therapeutic agent for treating thyroid carcinoma.

It further relates to use of 4-(3-chloro-4-(cyclopropylaminocarbonyl)aminophenoxy)-7-methoxy-6-quinolinecarboxamide, a pharmacologically acceptable salt thereof or a solvate thereof for producing a pharmaceutical composition containing an RET kinase inhibiting substance for administering to an organism containing a cell expressing mutant RET.

It further relates to 4-(3-chloro-4-(cyclopropylaminocarbonyl)aminophenoxy)-7-methoxy-6-quinolinecarboxamide, a pharmacologically acceptable salt thereof or a solvate thereof for a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

It further relates to 4-(3-chloro-4-(cyclopropylaminocarbonyl)aminophenoxy)-7-methoxy-6-quinolinecarboxamide, a pharmacologically acceptable salt thereof or a solvate thereof for a therapeutic agent for treating thyroid carcinoma.

It further relates to 4-(3-chloro-4-(cyclopropylaminocarbonyl)aminophenoxy)-7-methoxy-6-quinolinecarboxamide, a pharmacologically acceptable salt thereof or a solvate thereof for a pharmaceutical composition containing an RET kinase inhibiting substance for administering to an organism containing a cell expressing mutant RET.

It further relates to a method for predicting whether a patient is highly sensitive to 4-(3-chloro-4-(cyclopropylaminocarbonyl)aminophenoxy)-7-methoxy-6-quinolinecarboxamide, a pharmacologically acceptable salt thereof or a solvate thereof, the method including using the presence or the absence of RET mutation in the cell as an indication.

It further relates to a method for analyzing sensitivity of a cell to 4-(3-chloro-4-(cyclopropylaminocarbonyl)aminophenoxy)-7-methoxy-6-quinolinecarboxamide, a pharmacologically acceptable salt thereof or a solvate thereof, the method including determining the presence or the absence of RET mutation in the cell.

It further relates to a method for selecting a cell highly sensitive to 4-(3-chloro-4-(cyclopropylaminocarbonyl)aminophenoxy)-7-methoxy-6-quinolinecarboxamide, a pharmacologically acceptable salt thereof or a solvate thereof, the method including determining the presence or the absence of RET mutation in the cell.

It further relates to a method for selecting a patient highly sensitive to 4-(3-chloro-4-(cyclopropylaminocarbonyl)aminophenoxy)-7-methoxy-6-quinolinecarboxamide, a pharmacologically acceptable salt thereof or a solvate thereof, the method including determining the presence or the absence of RET mutation in the cell.

It further relates to a method for classifying a patient according to the result obtained from an analysis of sensitivity of the patient to 4-(3-chloro-4-(cyclopropylaminocarbonyl)aminophenoxy)-7-methoxy-6-quinolinecarboxamide, a pharmacologically acceptable salt thereof or a solvate thereof, the method including determining the presence or the absence of RET mutation in the cell.

It further relates to a method for selecting a patient intended for administration of 4-(3-chloro-4-(cyclopropylaminocarbonyl)aminophenoxy)-7-methoxy-6-quinolinecarboxamide, a pharmacologically acceptable salt thereof or a solvate thereof, the method including determining the presence or the absence of RET mutation in the cell and selecting a patient containing a cell expressing mutant RET from the determination results.

It further relates to a method for predicting a therapeutic effect of 4-(3-chloro-4-(cyclopropylaminocarbonyl)aminophenoxy)-7-methoxy-6-quinolinecarboxamide, a pharmacologically acceptable salt thereof or a solvate thereof on a patient, the method including determining the presence or the absence of RET mutation in a cell.

It further relates to a method for determining the presence or the absence of RET mutation in the cell from a patient, for predicting the sensitivity of the patient to 4-(3-chloro-4-(cyclopropylaminocarbonyl)aminophenoxy)-7-methoxy-6-quinolinecarboxamide, a pharmacologically acceptable salt thereof or a solvate thereof.

It further relates to an RET kinase inhibitor containing 4-(3-chloro-4-(cyclopropylaminocarbonyl)aminophenoxy)-7-methoxy-6-quinolinecarboxamide, a pharmacologically acceptable salt thereof or a solvate thereof.

The present invention provides a therapeutic agent and a method containing an RET kinase inhibiting substance for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, use of an RET kinase inhibiting substance for producing said therapeutic agent and an RET kinase inhibiting substance for said therapeutic agent.

The present invention also provides a therapeutic agent and a method containing an RET kinase inhibiting substance for treating thyroid carcinoma, use of an RET kinase inhibiting substance for producing said therapeutic agent and an RET kinase inhibiting substance for said therapeutic agent.

The present invention further provides a pharmaceutical composition containing an RET kinase inhibiting substance for administering to an organism having a cell expressing mutant RET, a method for treating a disease including administering to an organism having a cell expressing mutant RET, use of an RET kinase inhibiting substance for producing said pharmaceutical composition and an RET kinase inhibiting substance for said pharmaceutical composition.

The present invention also provides an RET kinase inhibitor.

In addition, the present invention provides a method for predicting the effect of an RET kinase inhibiting substance.

More specifically, the effect of an RET kinase inhibiting substance can be predicted by using the presence or the absence of RET mutation in the cell as an indication.

Since the method according to the invention enables one to predict the effect of the compound without administering the compound to the patient, it has become possible to select a patient who is expected to be more susceptible to the compound. Thus, contribution to the patient's QOL has become possible.

DETAILED DESCRIPTION OF THE INVENTION

Figure 1:
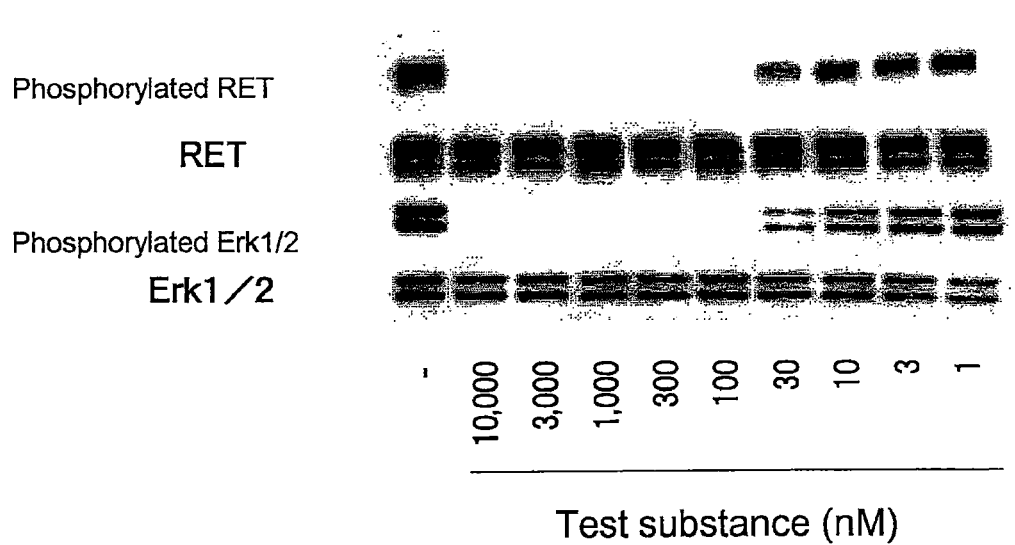
FIG. 1 shows an effect of 4-(3-chloro-4-(cyclopropylaminocarbonyl)aminophenoxy)-7-methoxy-6-quinolinecarboxamide on activations of RET kinase and Erk1/2 (indication being phosphorylation) in human medullary thyroid carcinoma cell line (TT) in culture. The leftmost lane is the determination of RET kinase and Erk1/2 activations (indication being phosphorylation) without addition of a test substance.

Hereinafter, embodiments of the present invention will be described. The following embodiments illustrate the present invention, which are not intended to limit the present invention. The present invention may be carried out in various embodiments without departing from the scope of the invention.

The documents, laid-open patent applications, patent publications and other patent documents cited herein are hereby incorporated by reference.

1. Therapeutic agent, pharmaceutical composition and therapeutic method of the invention (1) RET According to the present invention, RET is a protein encoded by ret proto-oncogene, for example, a polypeptide composed of an amino acid sequence represented by SEQ ID NO: 2 (GenBank Accession No:NM_020975) or SEQ ID NO: 4 (GenBank Accession No:NM_020630). The amino acid sequences represented by SEQ ID NO: 2 and SEQ ID NO: 4 have lengths 1114aa and 1072aa, respectively.

The ret proto-oncogene is, for example, a polynucleotide 181-3522 of the nucleotide sequence represented by SEQ ID NO: 1 (GenBank Accession No:NM_020975), or a polynucleotide 181-3396 of the nucleotide sequence represented by SEQ ID NO: 3 (GenBank Accession No:NM_020630).

Herein, these RETs may also be referred to as "wild-type RETs".

(2) Mutant RET

According to the present invention, mutant RET is a polypeptide containing a mutated version of the wild-type RET amino acid sequence, for example, an amino acid sequence having one or several amino acids deleted, substituted, added or varied by a combination thereof in the amino acid sequence represented by SEQ ID NO: 2 or 4. An example includes a polypeptide having RET kinase activity. Preferably, mutant RET may be, for example, a polypeptide having RET kinase activity and including an amino acid sequence having one amino acid substituted in the amino acid sequence of wild-type RET (e.g., the amino acid sequence represented by SEQ ID NO: 2 or 4).

Herein, "RET kinase activity" refers to a capacity of RET to phosphorylate a tyrosine residue of itself or other protein.

Examples of mutant RETs include polypeptides including the sequences described in (i)-(xix) below.

(i) An amino acid sequence having glycine at 321 substituted with other amino acid, preferably arginine, in the amino acid sequence represented by SEQ ID NO: 2 or 4 (Journal of Endocrinology Investigation, 28, 905-909, 2005.).

(ii) An amino acid sequence having glycine at 533 substituted with other amino acid, preferably cysteine, in the amino acid sequence represented by SEQ ID NO: 2 or 4 (Journal of Clinical Endocrinology and Metabolism, 88, 5438-5443, 2003.).

(iii) An amino acid sequence having cysteine at 609 substituted with other amino acid, preferably serine, in the amino acid sequence represented by SEQ ID NO: 2 or 4 (Clin Endocrinol, 63, 676-682, 2005.).

(iv) An amino acid sequence having cysteine at 611 substituted with other amino acid, preferably serine, tyrosine or phenylalanine, in the amino acid sequence represented by SEQ ID NO: 2 or 4 (European Journal of Human Genetics, 11, 364-368, 2003, Journal of Clinical Endocrinology and Metabolism, 86, 1104-1109, 2001.).

(v) An amino acid sequence having cysteine at 618 substituted with other amino acid, preferably arginine, serine, glycine or phenylalanine, in the amino acid sequence represented by SEQ ID NO: 2 or 4 (American Journal of Pathology, 168, 1262-1275, 2006, Journal of Clinical Endocrinology and Metabolism, 86, 1104-1109, 2001.).

(vi) An amino acid sequence having cysteine at 620 substituted with other amino acid, preferably arginine or serine, in the amino acid sequence represented by SEQ ID NO: 2 or 4 (American Journal of Pathology, 168, 1262-1275, 2006, Journal of Clinical Endocrinology and Metabolism, 86, 1104-1109, 2001.).

(vii) An amino acid sequence having cysteine at 630 substituted with other amino acid, preferably arginine or tyrosine, in the amino acid sequence represented by SEQ ID NO: 2 or 4 (Thyroid, 15, 668-671, 2005, Biochemical and Biophysical Research Communications, 255, 587-590, 1999.).

(viii) An amino acid sequence having aspartic acid at 631 substituted with other amino acid, preferably tyrosine, glycine, asparagine or alanine, in the amino acid sequence represented by SEQ ID NO: 2 or 4 (Biochemical and Biophysical Research Communications, 255, 587-590, 1999.).

(ix) An amino acid sequence having cysteine at 634 substituted with other amino acid, preferably arginine, glycine, tyrosine, phenylalanine, serine or tryptophan, in the amino acid sequence represented by SEQ ID NO: 2 or 4 (Biochemical and Biophysical Research Communications, 255, 587-590, 1999, Journal of Clinical Endocrinology and Metabolism, 86, 1104-1109, 2001, Biochemical and Biophysical Research Communications, 207, 1022-1028, 1995.).

(x) An amino acid sequence having glycine at 691 substituted with other amino acid, preferably serine, in the amino acid sequence represented by SEQ ID NO: 2 or 4 (Cancer Research, 66, 1177-1180, 2006.).

(xi) An amino acid sequence having glutamic acid at 768 substituted with other amino acid, preferably aspartic acid, in the amino acid sequence represented by SEQ ID NO: 2 or 4 (Clinical Chemistry, 50, 522-529, 2004. Journal of Clinical Endocrinology and Metabolism, 86, 1104-1109, 2001.).

(xii) An amino acid sequence having leucine at 790 substituted with other amino acid, preferably phenylalanine, in the amino acid sequence represented by SEQ ID NO: 2 or 4 (Journal of Clinical Endocrinology and Metabolism, 83, 770-774, 1998. Journal of Clinical Endocrinology and Metabolism, 86, 1104-1109, 2001.).

(xiii) An amino acid sequence having tyrosine at 791 substituted with other amino acid, preferably phenylalanine, in the amino acid sequence represented by SEQ ID NO: 2 or 4 (Journal of Clinical Endocrinology and Metabolism, 83, 770-774, 1998.).

(xiv) An amino acid sequence having valine at 804 substituted with other amino acid, preferably methionine, in the amino acid sequence represented by SEQ ID NO: 2 or 4 (Journal of Clinical Endocrinology and Metabolism, 86, 1104-1109, 2001.).

(xv) An amino acid sequence having tyrosine at 806 substituted with other amino acid, preferably cysteine, in the amino acid sequence represented by SEQ ID NO: 2 or 4 (Japanese Journal of Cancer Research, 90, 1-5, 1999.).

(xvi) An amino acid sequence having arginine at 844 substituted with other amino acid, preferably leucine, in the amino acid sequence represented by SEQ ID NO: 2 or 4 (Exp Clin Endocrinol Diabetes, 108, 128-132, 2000.).

(xvii) An amino acid sequence having alanine at 883 substituted with other amino acid, preferably phenylalanine or tyrosine, in the amino acid sequence represented by SEQ ID NO: 2 or 4 (European Journal of Endocrinology, 142, 573-575, 2000, Journal of Clinical Endocrinology and Metabolism, 89, 5823-5827, 2004.).

(xviii) An amino acid sequence having serine at 891 substituted with other amino acid, preferably alanine, in the amino acid sequence represented by SEQ ID NO: 2 or 4 (Journal of Clinical Endocrinology and Metabolism, 89, 4142-4145, 2004.).

(xix) An amino acid sequence having methionine at 918 substituted with other amino acid, preferably threonine, in the amino acid sequence represented by SEQ ID NO: 2 or 4 (Clinical Cancer Research, 8, 457-463, 2002.).

In addition, mutant RETs may be those including at least one of the substitutions indicated in (i)-(xix) above, specifically those including mutation sites where at least one amino acid selected from amino acids at codons 321, 533, 609, 611, 618, 620, 630, 631, 634, 691, 768, 790, 791, 804, 806, 844, 883, 891 and 918 is substituted with other amino acid, in the amino acid sequence represented by SEQ ID NO: 2 or 4. For example, a polypeptide including an amino acid sequence containing a mutation site where valine at position 804 is substituted with other amino acid and a mutation site where tyrosine at position 806 is substituted with other amino acid in the amino acid sequence represented by SEQ ID NO: 2 is contained in mutant RET. Herein, the number and the combination of the substitutions of (i)-(xix) above to be included in mutant RET are not particularly limited.

According to the present invention, mutant RET is preferably a polypeptide including a sequence represented by (iii), (iv), (v), (vi), (ix), (xi), (xii), (xiii), (xiv), (xviii) or (xix) above, more preferably a sequence represented by (ix) or (xix).

Herein, alphabetical notation of amino acids is expressed in generally used three-letter or single-letter codes. The alphabet preceding the number indicates single-letter code of the amino acid to be substituted, the alphabet following the number indicates single-letter code of the amino acid that replaces the original amino acid, and the number indicates the position of the amino acid in the amino acid sequence. For example, as indicated in (xix) above, when methionine at position 918 is substituted with threonine, it may be indicated as "M918T".

Moreover, the number following the codon may indicate the position of the amino acid in the amino acid sequence. For example, "an amino acid at codon 918" refers to 918th amino acid in the amino acid sequence.

According to the present invention, mutant RET may be a polypeptide having RET kinase activity and encoded by rearranged gene between gene encoding wild-type RET (hereinafter, also referred to as "RET gene") and other gene. Moreover, mutant RET of the invention is, for example, a polypeptide having RET kinase activity and encoded by a polynucleotide in which the polynucleotide having the nucleotide sequence represented by SEQ ID NO: 1 or 3 is partially rearranged with other gene. Furthermore, mutant RET of the invention is, for example, a polypeptide having RET kinase activity and encoded by a polynucleotide in which the polynucleotide 181-3522 of SEQ ID NO: 1 or polynucleotide 181-3396 of SEQ ID NO: 3 is rearranged with other gene.

Herein, "gene rearrangement" refers to recombination between genes that results in new gene.

Examples of mutant RETs include polypeptides of (i)-(xi) below. Embodiments of gene rearrangement for the polypeptides of (i)-(xi) below are described in the literature mentioned in parentheses.

(i) A polypeptide encoded by a rearranged gene (also referred to as "RET/PTC1") between RET gene and H4 (also referred to as CCDC6, coiled-coil domain containing 6 or D10S170; GenBank Accession No:NM_005436) gene (European Journal of Cancer, 41, 816-821, 2005, Cell, 60, 557-563, 1990.).

(ii) A polypeptide encoded by a rearranged gene (also referred to as "RET/PTC2") between RET gene and RIα (also referred to as PRKAR1A, cAMP-dependent regulatory type I alpha; GenBank Accession No:NM_212471) gene (Eur J Endocrinology, 147, 741-745, 2002.).

(iii) A polypeptide encoded by a rearranged gene (also referred to as "RET/PTC3") between RET gene and ELE1 (also referred to as NCOA4, nuclear receptor coactivator 4 or RFG; GenBank Accession No:NM_005437) gene (European Journal of Cancer, 41, 816-821, 2005.).

(iv) A polypeptide encoded by a rearranged gene (also referred to as "RET/PTC4") between RET gene and ELE1 (also referred to as NCOA4, nuclear receptor coactivator 4 or RFG; GenBank Accession No:NM_005437) gene (Oncogene, 13, 1093-1097, 1996.).

(v) A polypeptide encoded by a rearranged gene (also referred to as "RET/PTC5") between RET gene and RFG5 (also referred to as GOLGA5, golgin-84; GenBank Accession No:NM_005113) gene (Cancer Research, 58, 198-203, 1998.).

(vi) A polypeptide encoded by a rearranged gene (also referred to as "RET/PTC6") between RET gene and hTIF (also referred to as TRIM24, tripartite motif-containing 24 or PTC6; GenBank Accession No:NM_003852) gene (Oncogene, 18, 4388-4393, 1999.).

(vii) A polypeptide encoded by a rearranged gene (also referred to as "RET/PTC7") between RET gene and RFG7 (also referred to as TRIM33, tripartite motif-containing 33, PTC7; GenBank Accession No:NM_033020) gene (Cancer Research, 60, 2786-2789, 2000.).

(viii) A polypeptide encoded by a rearranged gene (also referred to as "RET/PTC8") between RET gene and kinectin (also referred to as KTN1, kinectin 1; GenBank Accession No:NM_182926) gene (Cancer Research, 60, 7028-7032, 2000. Cancer Research, 60, 2786-2789, 2000.).

(ix) A polypeptide encoded by a rearranged gene (also referred to as "RET/ELKS") between RET gene and ELKS (also referred to as RAB6IP2 or RAB6 interacting protein 2; GenBank Accession No:NM_178037) gene (Genes Chromosomes Cancer, 25, 97-103, 1999.).

(x) A polypeptide encoded by a rearranged gene (also referred to as "RET/PCM-1") between RET gene and PCM-1 (also referred to as PCM1 or pericentriolar material 1; GenBank Accession No:NM_006197) gene (Oncogene, 19, 4236-4242, 2000.).

(xi) A polypeptide encoded by a rearranged gene (also referred to as "RFP-RET") between RET gene and gene RFP (also referred to as ret finger protein; GenBank Accession No:NM_006510) (Endocrinology, 145, 5448-5451, 2004.).

The presence or the absence of RET mutation can be verified through analysis of sequence of RET gene or sequence of RET gene transcript, i.e., mRNA. Analysis procedure may, for example, be dideoxynucleotide chain termination method (Sanger et al. (1977), Proc. Natl. Acad. Sci. USA 74: 5463). The sequence can be analyzed using a suitable DNA sequencer.

Alternatively, the presence or the absence of RET mutation may be analyzed, for example, by a technique such as in situ hybridization, northern blot analysis, DNA microarray, RT-PCR or SSCP-PCR (Single-Strand Conformation Polymorphism-PCR). These techniques can be carried out according to routine procedures (Clinical Cancer Research, 8, 457-463, 2002.).

The presence or the absence of RET mutation may also be analyzed, for example, by an immunochemical method (e.g., immunohistochemical method, immunoprecipitation, western blot, flow cytometry, ELISA, RIA, etc.). These techniques can be carried out according to routine procedures.

The primer sequences for PCR to analyze the presence or the absence of mutant RET can be designed according to a routine procedure. For example, the primer sequences can be designed using Primer Expression (Perkin-Elmer Applied Biosystems).

In order to analyze the presence or the absence of mutant RET, for example, primers mentioned in Table 1 may be used. For example, for analyzing RET/PTC1, polynucleotides having the sequences represented by SEQ ID NOS: 5 and 6 can be employed as primers.

TABLE 1

| Mutant RET intended for analysis | Primer 1 | Primer 2 |
|---|---|---|
| RET/PTC1 | SEQ ID NO: 5 | SEQ ID NO: 6 |
| RET/PTC2 | SEQ ID NO: 7 | SEQ ID NO: 6 |
| RET/PTC3 | SEQ ID NO: 8 | SEQ ID NO: 9 |
| RET/PTC4 | SEQ ID NO: 10 | SEQ ID NO: 11 |
| RET/PTC5 | SEQ ID NO: 12 | SEQ ID NO: 13 |
| RET/PTC6 | SEQ ID NO: 12 | SEQ ID NO: 14 |
| RET/PTC7 | SEQ ID NO: 12 | SEQ ID NO: 15 |
| RET/PTC8 | SEQ ID NO: 12 | SEQ ID NO: 16 |
| RET/ELKS | SEQ ID NO: 17 | SEQ ID NO: 18 |
| RET/PCM-1 | SEQ ID NO: 19 | SEQ ID NO: 20 |

Table 1 indicates some of the exemplary primers for mutant RETs intended for analysis.

The nucleotide sequences represented by SEQ ID NOS: 5-20 are shown below.

```
ATT GTC ATC TCG CCG TTC         SEQ ID NO: 5

TGC TTC AGG ACG TTG AAC         SEQ ID NO: 6

TAT CGC AGG AGA GAC TGT GAT     SEQ ID NO: 7

TGG AGA AGA GAG GCT GTA TC      SEQ ID NO: 8

CGT TGC CTT GAC TTT TC          SEQ ID NO: 9

TGC CCC TTC AGT GTT CCT ACT     SEQ ID NO: 10

CTT GAT AAC ACT GGC AGG TT      SEQ ID NO: 11

GAG GCG TTC TCT TTC AGC AT      SEQ ID NO: 12

TGG AAG AAC TTC GGC ATG AG      SEQ ID NO: 13

GAA TTC ACA GCC ACC AAG TG      SEQ ID NO: 14

CTA CTT AGC TTT CCA AGT GG      SEQ ID NO: 15

GGG ACA GAC ACC TTT GGA AAT A   SEQ ID NO: 16

GTTGAAGGAGTCCTTGACTG            SEQ ID NO: 17
```

-continued

| | |
|---|---|
| CTTTCAGCATCTTCACGG | SEQ ID NO: 18 |
| AGTGAAGTTTCTACCATCC | SEQ ID NO: 19 |
| GGCGTTCTCTTTCAGCATCT | SEQ ID NO: 20 |

(3) Cell Expressing Mutant RET

According to the present invention, a cell expressing mutant RET is preferably a cell from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia or mucosal neuromas of the gastrointestinal tract. Alternatively, a cell expressing mutant RET, according to the present invention, is preferably a cell from thyroid carcinoma.

(4) RET Kinase Inhibiting Substance of the Invention

Herein, a "halogen atom" refers to a fluorine atom, a chlorine atom, a bromine atom or an iodine atom.

Preferable examples of a "halogen atom" include a fluorine atom and a chlorine atom.

Herein, "$C_{1-6}$ alkyl group" refers to linear or branched alkyl group with a carbon number of 1-6, specific examples being methyl group, ethyl group, 1-propyl group (n-propyl group), 2-propyl group (i-propyl group), 2-methyl-1-propyl group (1-butyl group), 2-methyl-2-propyl group (t-butyl group), 1-butyl group (n-butyl group), 2-butyl group (s-butyl group), 1-pentyl group, 2-pentyl group, 3-pentyl group, 2-methyl-1-butyl group, 3-methyl-1-butyl group, 2-methyl-2-butyl group, 3-methyl-2-butyl group, 2,2-dimethyl-1-propyl group, 1-hexyl group, 2-hexyl group, 3-hexyl group, 2-methyl-1-pentyl group, 3-methyl-1-pentyl group, 4-methyl-1-pentyl group, 2-methyl-2-pentyl group, 3-methyl-2-pentyl group, 4-methyl-2-pentyl group, 2-methyl-3-pentyl group, 3-methyl-3-pentyl group, 2,3-dimethyl-1-butyl group, 3,3-dimethyl-1-butyl group, 2,2-dimethyl-1-butyl group, 2-ethyl-1-butyl group, 3,3-dimethyl-2-butyl group and 2,3-dimethyl-2-butyl group.

Preferable examples of "$C_{1-6}$ alkyl group" include methyl group, ethyl group, 1-propyl group, 2-propyl group, 2-methyl-1-propyl group, 2-methyl-2-propyl group, 1-butyl group and 2-butyl group.

Herein, "$C_{1-6}$ alkylene group" refers to divalent group derived from "$C_{1-6}$ alkyl group" defined above by removing any one hydrogen atom therefrom, and specific examples include methylene group, 1,2-ethylene group, 1,1-ethylene group, 1,3-propylene group, tetramethylene group, pentamethylene group and hexamethylene group.

Herein, "$C_{2-6}$ alkenyl group" refers to linear or branched alkenyl group having one double bond and a carbon number of 2-6, and specific examples include ethenyl group (vinyl group), 1-propenyl group, 2-propenyl group (allyl group), 1-butenyl group, 2-butenyl group, 3-butenyl group, pentenyl group and hexenyl group.

Herein, "$C_{2-6}$ alkynyl group" refers to linear or branched alkynyl group having one triple bond and a carbon number of 2-6, and specific examples include ethinyl group, 1-propynyl group, 2-propynyl group, 1-butynyl group, 2-butynyl group, 3-butynyl group, pentynyl group and hexynyl group.

Herein, "$C_{3-8}$ cycloalkyl group" refers to monocyclic or bicyclic saturated aliphatic hydrocarbon group with a carbon number of 3-8, and specific examples include cyclopropyl group, cyclobutyl group, cyclopentyl group, cyclohexyl group, cycloheptyl group, cyclooctyl group, bicyclo[2.1.0] pentyl group, bicyclo[3.1.0]hexyl group, bicyclo[2.1.1]hexyl group, bicyclo[4.1.0]heptyl group, bicyclo[2.2.1]heptyl group (norbornyl group), bicyclo[3.3.0]octyl group, bicyclo [3.2.1]octyl group and bicyclo[2.2.2]octyl group.

Preferable examples of "$C_{3-8}$ cycloalkyl group" include cyclopropyl group, cyclobutyl group and cyclopentyl group.

Herein, "$C_{6-10}$ aryl group" refers to aromatic hydrocarbon cyclic group with a carbon number of 6-10, and specific examples include phenyl group, 1-naphthyl group, 2-naphthyl group, indenyl group and azulenyl group.

A preferable example of "$C_{6-10}$ aryl group" includes phenyl group.

Herein, "a heteroatom" refers to a nitrogen atom, an oxygen atom or a sulfur atom.

Herein, "5-10-membered heteroaryl group" refers to aromatic cyclic group having 5-10 atoms forming the ring including 1-5 heteroatoms, and specific examples include furyl group, thienyl group, pyrrolyl group, imidazolyl group, triazolyl group, tetrazolyl group, thiazolyl group, pyrazolyl group, oxazolyl group, isoxazolyl group, isothiazolyl group, furazanyl group, thiadiazolyl group, oxadiazolyl group, pyridyl group, pyrazinyl group, pyridazinyl group, pyrimidinyl group, triazinyl group, purinyl group, pteridinyl group, quinolyl group, isoquinolyl group, naphthyridinyl group, quinoxalinyl group, cinnolinyl group, quinazolinyl group, phthalazinyl group, imidazopyridyl group, imidazothiazolyl group, imidazoxazolyl group, benzothiazolyl group, benzoxazolyl group, benzimidazolyl group, indolyl group, isoindolyl group, indazolyl group, pyrrolopyridyl group, thienopyridyl group, furopyridyl group, benzothiadiazolyl group, benzoxadiazolyl group, pyridopyrimidinyl group, benzofuryl group, benzothienyl group and thienofuryl group.

Preferable examples of "5-10-membered heteroaryl group" include furyl group, thienyl group, pyrrolyl group, imidazolyl group, thiazolyl group, pyrazolyl group, oxazolyl group, isoxazolyl group, isothiazolyl group, pyridyl group and pyrimidinyl group.

Herein, "3-10-membered non-aromatic heterocyclic group":

(a) has 3-10 atoms forming the ring;
(b) has 1-2 heteroatoms included in the atoms forming the ring;
(c) may include 1-2 double bonds in the ring;
(d) may have 1-3 carbonyl groups, sulfinyl groups or sulfonyl groups in the ring; and
(e) is non-aromatic monocyclic or bicyclic group, where when a nitrogen atom is included in the atoms forming the ring, the nitrogen atom may have a binding hand.

Specific examples include aziridinyl group, azetidinyl group, pyrrolidinyl group, piperidinyl group, azepanyl group, azocanyl group, piperazinyl group, diazepanyl group, diazocanyl group, diazabicyclo[2.2.1]heptyl group, morpholinyl group, thiomorpholinyl group, 1,1-dioxothiomorpholinyl group, oxiranyl group, oxetanyl group, tetrahydrofuryl group, dioxoranyl group, tetrahydropyranyl group, dioxanyl group, tetrahydrothienyl group, tetrahydrothiopyranyl group, oxazolidinyl group and thiazolidinyl group.

Preferable examples of "3-10-membered non-aromatic heterocyclic group" include aziridinyl group, azetidinyl group, pyrrolidinyl group, piperidinyl group, azepanyl group, piperazinyl group, diazepanyl group, morpholinyl group, thiomorpholinyl group, 1,1-dioxothiomorpholinyl group, tetrahydrofuryl group and tetrahydropyranyl group.

Herein, "$C_{1-6}$ alkoxy group" refers to group in which an oxygen atom is bound to the terminal of "$C_{1-6}$ alkyl group" defined above, and specific examples include methoxy group, ethoxy group, 1-propoxy group (n-propoxy group), 2-propoxy group (1-propoxy group), 2-methyl-1-propoxy group (1-butoxy group), 2-methyl-2-propoxy group (t-butoxy group), 1-butoxy group (n-butoxy group), 2-butoxy group (s-butoxy group), 1-pentyloxy group, 2-pentyloxy group, 3-pentyloxy group, 2-methyl-1-butoxy group, 3-methyl-1-butoxy group, 2-methyl-2-butoxy group, 3-methyl-2-butoxy group, 2,2-dimethyl-1-propoxy group, 1-hexyloxy group, 2-hexyloxy group, 3-hexyloxy group, 2-methyl-1-pentyloxy group, 3-methyl-1-pentyloxy group, 4-methyl-1-pentyloxy group, 2-methyl-2-pentyloxy group, 3-methyl-2-pentyloxy group, 4-methyl-2-pentyloxy group, 2-methyl-3-pentyloxy group, 3-methyl-3-pentyloxy group, 2,3-dimethyl-1-butoxy group, 3,3-dimethyl-1-butoxy group, 2,2-dimethyl-1-butoxy group, 2-ethyl-1-butoxy group, 3,3-dimethyl-2-butoxy group and 2,3-dimethyl-2-butoxy group.

Preferable examples of "$C_{1-6}$ alkoxy group" include methoxy group, ethoxy group, 1-propoxy group, 2-propoxy group, 2-methyl-1-propoxy group, 2-methyl-2-propoxy group, 1-butoxy group and 2-butoxy group.

Herein, "$C_{1-6}$ alkylthio group" refers to group in which a sulfur atom is bound to the terminal of "$C_{1-6}$ alkyl group" defined above, and specific examples include methylthio group, ethylthio group, 1-propylthio group (n-propylthio group), 2-propylthio group (i-propylthio group), 2-methyl-1-propylthio group (1-butylthio group), 2-methyl-2-propylthio group (t-butylthio group), 1-butylthio group (n-butylthio group), 2-butylthio group (s-butylthio group), 1-pentylthio group, 2-pentylthio group, 3-pentylthio group, 2-methyl-1-butylthio group, 3-methyl-1-butylthio group, 2-methyl-2-butylthio group, 3-methyl-2-butylthio group, 2,2-dimethyl-1-propylthio group, 1-hexylthio group, 2-hexylthio group, 3-hexylthio group, 2-methyl-1-pentylthio group, 3-methyl-1-pentylthio group, 4-methyl-1-pentylthio group, 2-methyl-2-pentylthio group, 3-methyl-2-pentylthio group, 4-methyl-2-pentylthio group, 2-methyl-3-pentylthio group, 3-methyl-3-pentylthio group, 2,3-dimethyl-1-butylthio group, 3,3-dimethyl-1-butylthio group, 2,2-dimethyl-1-butylthio group, 2-ethyl-1-butylthio group, 3,3-dimethyl-2-butylthio group and 2,3-dimethyl-2-butylthio group.

Preferable examples of "$C_{1-6}$ alkylthio group" include methylthio group, ethylthio group, 1-propylthio group (n-propylthio group), 2-propylthio group (i-propylthio group), 2-methyl-1-propylthio group (1-butylthio group), 2-methyl-2-propylthio group (t-butylthio group), 1-butylthio group (n-butylthio group) and 2-butylthio group (s-butylthio group).

Herein, "$C_{3-8}$ cycloalkoxy group" refers to group in which an oxygen atom is bound to the terminal of "$C_{3-8}$ cycloalkyl group" defined above, and specific examples include cyclopropoxy group, cyclobutoxy group, cyclopentyloxy group, cyclohexyloxy group, cycloheptyloxy group, cyclooctyloxy group, bicyclo[2.1.0]pentyloxy group, bicyclo[3.1.0]hexyloxy group, bicyclo[2.1.1]hexyloxy group, bicyclo[4.1.0]heptyloxy group, bicyclo[2.2.1]heptyloxy group (norbornyloxy group), bicyclo[3.3.0]octyloxy group, bicyclo[3.2.1]octyloxy group and bicyclo[2.2.2]octyloxy group.

Preferable examples of "$C_{3-8}$ cycloalkoxy group" include cyclopropoxy group, cyclobutoxy group and cyclopentyloxy group.

Herein, "mono-$C_{1-6}$ alkylamino group" refers to group in which a hydrogen atom in amino group is substituted with "$C_{1-6}$ alkyl group" defined above, and specific examples include methylamino group, ethylamino group, 1-propylamino group (n-propylamino group), 2-propylamino group (i-propylamino group), 2-methyl-1-propylamino group (1-butylamino group), 2-methyl-2-propylamino group (t-butylamino group), 1-butylamino group (n-butylamino group), 2-butylamino group (s-butylamino group), 1-pentylamino group, 2-pentylamino group, 3-pentylamino group, 2-methyl-1-butylamino group, 3-methyl-1-butylamino group, 2-methyl-2-butylamino group, 3-methyl-2-butylamino group, 2,2-dimethyl-1-propylamino group, 1-hexylamino group, 2-hexylamino group, 3-hexylamino group, 2-methyl-1-pentylamino group, 3-methyl-1-pentylamino group, 4-methyl-1-pentylamino group, 2-methyl-2-pentylamino group, 3-methyl-2-pentylamino group, 4-methyl-2-pentylamino group, 2-methyl-3-pentylamino group, 3-methyl-3-pentylamino group, 2,3-dimethyl-1-butylamino group, 3,3-dimethyl-1-butylamino group, 2,2-dimethyl-1-butylamino group, 2-ethyl-1-butylamino group, 3,3-dimethyl-2-butylamino group and 2,3-dimethyl-2-butylamino group.

Herein, "di-$C_{1-6}$ alkylamino group" refers to group in which two hydrogen atoms in amino group are substituted with identical or different "$C_{1-6}$ alkyl group" defined above, and specific examples include N,N-dimethylamino group, N,N-diethylamino group, N,N-di-n-propylamino group, N,N-di-i-propylamino group, N,N-di-n-butylamino group, N,N-di-i-butylamino group, N,N-di-s-butylamino group, N,N-di-t-butylamino group, N-ethyl-N-methylamino group, N-n-propyl-N-methylamino group, N-i-propyl-N-methylamino group, N-n-butyl-N-methylamino group, N-i-butyl-N-methylamino group, N-s-butyl-N-methylamino group and N-t-butyl-N-methylamino group.

Herein, "$C_{2-7}$ acyl group" refers to carbonyl group bound with "$C_{1-6}$ alkyl group" defined above, and specific examples include acetyl group, propionyl group, isopropionyl group, butyryl group, isobutyryl group, valeryl group, isovaleryl group and pivaloyl group.

Herein, "$C_{2-7}$ alkoxycarbonyl group" refers to carbonyl group bound with "$C_{1-6}$ alkoxy group" defined above, and specific examples include methoxycarbonyl group, ethoxycarbonyl group, 1-propyloxycarbonyl group, 2-propyloxycarbonyl group and 2-methyl-2-propoxy carbonyl group.

Herein, "that may have a substituent" means "that may have one or more substituents at substitutable positions in any combination", and specific examples of the substituent include a halogen atom, hydroxyl group, thiol group, nitro group, cyano group, formyl group, carboxyl group, amino group, silyl group, methanesulfonyl group, $C_{1-6}$ alkyl group, $C_{2-6}$ alkenyl group, $C_{2-6}$ alkynyl group, $C_{3-8}$ cycloalkyl group, $C_{6-10}$ aryl group, 5-10-membered heteroaryl group, 3-10-membered non-aromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group and $C_{2-7}$ alkoxycarbonyl group. In this case, $C_{1-6}$ alkyl group, $C_{2-6}$ alkenyl group, $C_{2-6}$ alkynyl group, $C_{3-8}$ cycloalkyl group, $C_{6-40}$ aryl group, 5-10-membered heteroaryl group, 3-10-membered non-aromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group and $C_{2-7}$ alkoxycarbonyl group may each independently have 1-3 groups selected from the following substituent groups.

<Substituent Groups>

A halogen atom, hydroxyl group, thiol group, nitro group, cyano group, $C_{1-6}$ alkyl group, $C_{3-8}$ cycloalkyl group, $C_{2-6}$ alkenyl group, $C_{2-6}$ alkynyl group, $C_{6-10}$ aryl group, 5-10-membered heteroaryl group, 3-10-membered non-aromatic heterocyclic group, $C_{1-6}$ alkoxy group and $C_{1-6}$ alkylthio group.

According to the present invention, an RET kinase inhibiting substance may, for example, be a compound represented by General Formula (I)

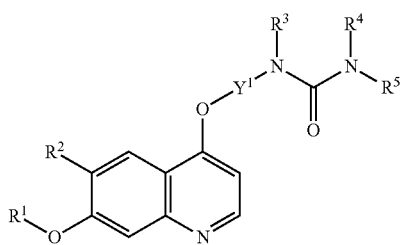

(i) $R^1$ $R^1$ represents a group represented by Formula —$V^1$—$V^2$—$V^3$ (wherein, $V^1$ represents $C_{1-6}$ alkylene group that may have a substituent; $V^2$ represents a single bond, an oxygen atom, a sulfur atom, carbonyl group, sulfinyl group, sulfonyl group, group represented by Formula —$CONR^6$—, group represented by Formula —$SO_2NR^6$—, group represented by Formula —$NR^6SO_2$—, group represented by Formula —$NR^6CO$— or group represented by Formula —$NR^6$— (wherein, $R^6$ represents a hydrogen atom, $C_{1-6}$ alkyl group that may have a substituent or $C_{3-8}$ cycloalkyl group that may have a substituent); $V^3$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent).

A preferable example of $R^1$ includes $C_{1-6}$ alkyl group. In this case, $R^1$ may have a substituent selected from 3-10-membered non-aromatic heterocyclic group which may have $C_{1-6}$ alkyl group, hydroxyl group, $C_{1-6}$ alkoxy group, amino group, mono-$C_{1-6}$ alkylamino group and di-$C_{1-6}$ alkylamino group.

More preferable examples of $R^1$ include methyl group and group represented by any one of the following Formulae

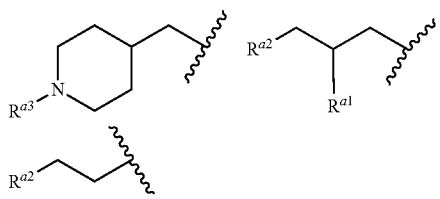

(wherein, $R^{a3}$ represents methyl group; $R^{a1}$ represents a hydrogen atom or hydroxyl group; $R^{a2}$ represents methoxy group, ethoxy group, 1-pyrrolidinyl group, 1-piperidinyl group, 4-morpholinyl group, dimethylamino group or diethylamino group).

Still more preferable examples of $R^1$ include methyl group and 2-methoxyethyl group.

(ii) $R^2$ $R^2$ represents cyano group, $C_{1-6}$ alkoxy group that may have a substituent, carboxyl group, $C_{2-7}$ alkoxycarbonyl group that may have a substituent or group represented by Formula —$CONV^{a11}V^{a12}$ (wherein, $V^{a11}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent; $V^{a12}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent, 3-10-membered non-aromatic heterocyclic group that may have a substituent, hydroxyl group, $C_{1-6}$ alkoxy group that may have a substituent or $C_{3-8}$ cycloalkoxy group that may have a substituent).

Preferable examples of $R^2$ include cyano group or group represented by Formula —$CONV^{a11}V^{a12}$ (wherein, $V^{a11}$ and $V^{a12}$ have the same meaning as defined above).

More preferable examples of $R^2$ include cyano group or group represented by Formula —$CONHV^{a16}$ (wherein, $V^{a16}$ represents a hydrogen atom, $C_{1-6}$ alkyl group, $C_{3-8}$ cycloalkyl group, $C_{1-6}$ alkoxy group or $C_{3-8}$ cycloalkoxy group, where $V^{a16}$ may have a substituent selected from a halogen atom, cyano group, hydroxyl group and $C_{1-6}$ alkoxy group).

Still more preferable example of $R^2$ includes a group represented by Formula —$CONHV^{a17}$ (wherein, $V^{a17}$ represents a hydrogen atom, $C_{1-6}$ alkyl group or $C_{1-6}$ alkoxy group).

The most preferable example of $R^2$ includes a group represented by Formula —$CONHV^{a18}$ (wherein, $V^{a18}$ represents a hydrogen atom, methyl group or methoxy group).

(iii) $Y^1$ $Y^1$ represents a group represented by Formula

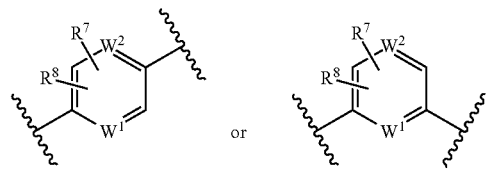

(wherein, $R^7$ and $R^8$ each independently represent a hydrogen atom, a halogen atom, cyano group, nitro group, amino group, $C_{1-6}$ alkyl group that may have a substituent, $C_{3-8}$ cycloalkyl group that may have a substituent, $C_{1-6}$ alkoxy group that may have a substituent, $C_{1-6}$ alkylthio group that may have a substituent, formyl group, $C_{2-7}$ acyl group that may have a substituent, $C_{2-7}$ alkoxycarbonyl group that may have a substituent or group represented by Formula —$CONV^{d1}V^{d2}$ (wherein, $V^{d1}$ and $V^{d2}$ each independently represent a hydrogen atom or $C_{1-6}$ alkyl group that may have a substituent); and $W^1$ and $W^2$ each independently represent a carbon atom or a nitrogen atom that may have a substituent).

A preferable example of $Y^1$ includes a group represented by Formula

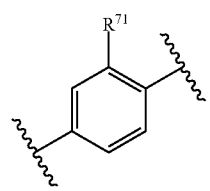

(wherein, $R^{71}$ represents a hydrogen atom or a halogen atom).

(iv) $R^3$ and $R^4$ $R^3$ and $R^4$ each independently represent a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{2-7}$ acyl group that may have a substituent or $C_{2-7}$ alkoxycarbonyl group that may have a substituent.

A preferable example of $R^3$ and $R^4$ includes a hydrogen atom.

(v) $R^5$ $R^5$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered non-aromatic heterocyclic group that may have a substituent.

Preferable examples of $R^3$ include a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent or 3-10-membered non-aromatic heterocyclic group that may have a substituent.

More preferable examples of $R^5$ include a hydrogen atom, $C_{1-6}$ alkyl group, $C_{3-8}$ cycloalkyl group and $C_{6-10}$ aryl group (where $R^5$ may have at least one substituent selected from a halogen atom and methanesulfonyl group).

More preferable examples of $R^5$ include methyl group, ethyl group or cyclopropyl group.

Moreover, preferable examples of the compound represented by General Formula (I) include:

N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropylurea;
N-(4-((6-cyano-7-(((2R)-3-(diethylamino)-2-hydroxypropyl)oxy)-4-quinolyl)oxy)phenyl)-N'-(4-fluorophenyl)urea;
N-(4-((6-cyano-7-(((2R)-2-hydroxy-3-(1-pyrrolidino)propyl)oxy)-4-quinolyl)oxy)phenyl)-N'-(4-fluorophenyl)urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-((2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropylurea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino) phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-(2R)-3-diethylamino-2-hydroxypropoxy)-6-quinolinecarboxamide;
N6-methyl-4-(3-chloro-4-(((ethylamino)carbonyl)amino)phenoxy)-7-(2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-(1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropylurea;
N-(4-(6-cyano-7-(3-(4-morpholino)propoxy)-4-quinolyl)oxyphenyl)-N'-(3-(methylsulfonyl)phenyl)urea;
4-(4-((cyclopropylamino)carbonyl)aminophenoxy)-7-methoxy-6-quinolinecarboxamide;
4-(3-fluoro-4-((2-fluoroethylamino)carbonyl)aminophenoxy)-7-methoxy-6-quinolinecarboxamide;
N6-(2-ethoxyethyl)-4-(3-chloro-4-(((methylamino)carbonyl)amino)phenoxy)-7-methoxy-6-quinolinecarboxamide;
4-(4-(3-ethylureido)-3-fluoro-phenoxy)-7-methoxyquinoline-6-carboxylic acid (2-cyanoethyl)amide; and
N-(4-(6-(2-cyanoethyl)carbamoyl-7-methoxy-4-quinolyl)oxy-2-fluorophenyl)-N'-cyclopropylurea.

More preferable examples of the compound represented by General Formula (I) include:

4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-((((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide.

A still more preferable example of the compound represented by General Formula (I) further includes 4-(3-chloro-4-(cyclopropylaminocarbonyl)aminophenoxy)-7-methoxy-6-quinolinecarboxamide (see Formula (II)).

The most preferable example of the RET kinase inhibiting substance includes methanesulfonate of 4-(3-chloro-4-(cyclopropylaminocarbonyl)aminophenoxy)-7-methoxy-6-quinolinecarboxamide.

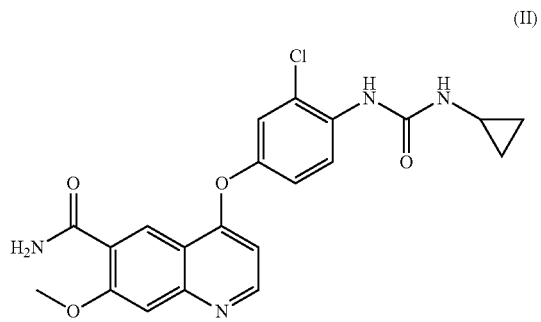 [SMILES: COc1cc2nccc(Oc3ccc(NC(=O)NC4CC4)c(Cl)c3)c2cc1C(N)=O]

(II)

The compound represented by General Formula (I) can be produced by a known method, for example, methods described in International publication No. 02/32872 pamphlet (WO02/32872) and International publication No. 2005/063713 pamphlet (WO2005/063713).

In addition, an RET kinase inhibiting substance of the invention is, for example: 5-(5-fluoro-2-oxo-1,2-dihydroindole-3-ylidenemethyl)-2,4-dimethyl-1H-pyrrole-3-carboxylic acid(2-diethylaminoethyl)amide (hereinafter, also referred to as "SU11248"; Clinical Cancer Research, 9, 327-337, 2003, Journal of Medicinal Chemistry, 46: 1116-9, 2003, WO01/060814) (see Formula (III))

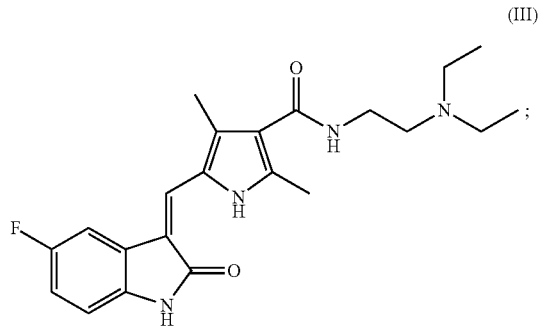 [SMILES: CCN(CC)CCNC(=O)c1c(C)[nH]c(/C=C2\C(=O)Nc3ccc(F)cc32)c1C]

(III)

N-{2-chloro-4-[(6,7-dimethoxy-4-quinolyl)oxy]phenyl}-N'-(5-methyl-3-isoxazolyl)urea (hereinafter, also referred to as "KRN951"; WO02/088110) (see Formula (IV))

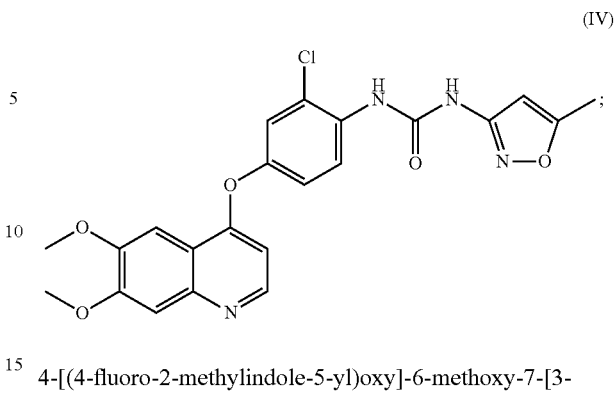

(IV)

4-[(4-fluoro-2-methylindole-5-yl)oxy]-6-methoxy-7-[3-(pyrrolidine-1-yl)propoxy]quinazoline (hereinafter, also referred to as "AZD2171"; Cancer Research. 65:4389-400, 2005, WO00/47212) (see Formula (V))

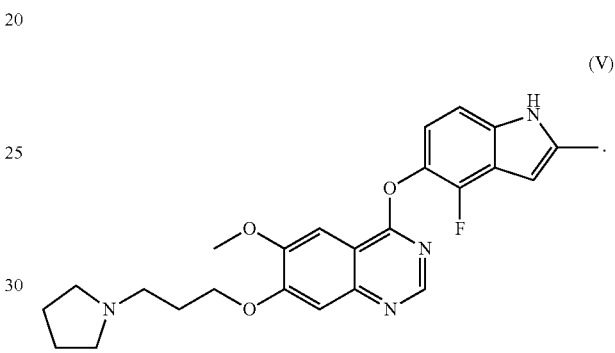

(V)

SU11248, KRN951 and AZD2171 can be produced according to a known method. They can be produced, for example, according to the methods described in the respective literatures.

According to the present invention, the RET kinase inhibiting substance may form a pharmacologically acceptable salt with acid or base. According to the present invention, the RET kinase inhibiting substance also includes such pharmacologically acceptable salts. Examples of salts formed with acid include inorganic acid salts such as hydrochloride, hydrobromate, sulfate and phosphate, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluenesulfonic acid and trifluoroacetic acid. Examples of salts formed with base include alkali metal salts such as sodium salt and potassium salt, alkaline earth metal salts such as calcium salt and magnesium salt, organic base salts such as trimethylamine, triethylamine, pyridine, picoline, dicyclohexylamine, N,N'-dibenzyl ethylenediamine, arginine and lysine and ammonium salt.

Furthermore, according to the present invention, the RET kinase inhibiting substance also includes, if any, solvates and enantiomers of these compounds. Examples of solvates include hydrates and nonhydrates, preferably hydrates. Examples of solvents include water, alcohols (for example, methanol, ethanol, n-propanol) and dimethylformamide.

Moreover, according to the present invention, the RET kinase inhibiting substance may be crystalline or amorphous. If a crystalline polymorph is present, it may be a single polymorph or a mixture of polymorphs in any crystalline shape.

According to the present invention, the RET kinase inhibiting substance includes RET kinase inhibiting substances susceptible to metabolism such as oxidation, reduction, hydrolysis and conjugation in vivo. The RET kinase inhibiting substance of the invention also includes compounds that generate an RET kinase inhibiting substance by undergoing metabolism such as oxidation, reduction and hydrolysis in vivo.

The RET kinase inhibiting substance of the invention has activity of inhibiting RET kinase activity (hereinafter, also referred to as "RET kinase-inhibiting activity"). The inhibition capacity of the RET kinase inhibiting substance of the invention is not limited as long as it inhibits kinase activity of RET. Examples of methods for determining the RET kinase-inhibiting activity of the RET kinase inhibiting substance include cell free kinase assay, western blotting, cell growth assay and viability assay. Examples of the cell growth assay include tritium thymidine uptake method, MTT method, XTT method (cell counting kit-8 (Dojindo Laboratories)), Alamar-Blue method, Neutral Red method, BrdU method, Ki67 staining and PCNA staining. Examples of the viability assay include TUNNEL staining, Caspase-3 cleavage detection and PARP cleavage detection. These methods may be carried out according to conventional techniques (Blood. 2005, 105, 2941-2948, Molecular Cancer Therapeutics. 2005, 4, 787-798).

Hereinafter, an example of a method for determining RET kinase-inhibiting activity will be described.

The RET kinase-inhibiting activity can be determined by cell free kinase assay. RET can be prepared by gene-engineering means according to a conventional method. For example, according to the method of Baculovirus Expression System, human recombinant GST fusion protein, human recombinant histidine-tag fusion protein or the like may be expressed in an insect cell (*Spodoptera frugiperda* 9 (Sf9)). Furthermore, the expressed recombinant protein can be purified by affinity chromatography (e.g., GSH-agarose (Sigma) or Ni-NTH-agarose (Qiagen)). The purity and identification of the protein can be confirmed by SDS-PAGE, silver staining and western blotting using an antibody specific to RET.

The cell free kinase assay can be carried out as follows.

First, to each well of a plate (e.g., 96-well, 384-well, etc.), a mixed solution including 20 μl of standard reaction solution, 5 μl of ATP solution, 5 μl of the test substance, and a mixed solution including 10 μl of solution containing 50 ng of RET recombinant protein and 10 μl of solution containing 125 ng of biotinylated Poly(Glu, Tyr)$_{4:1}$ can be added sequentially.

This kinase reaction solution (50 μl) may contain 60 mM HEPES-NaOH (pH7.5), 3 mM $MgCl_2$, 3 mM $MnCl_2$, 3 μM Na-orthovanadate, 1.2 mM DTT, 50 μg/ml $PEG_{20000}$ and 1 μM ATP. In this case, the ATP labeled with a radioactive isotope such as [γ-$^{32}$P]-ATP or [γ-$^{33}$P]-ATP may be used.

The reaction solution may be incubated for a certain period of time, and then 50 μl of 2% (v/v) $H_3PO_4$ solution may be added to terminate the reaction.

Each well may be subjected to an appropriate washing procedure.

RET kinase-inhibiting activity can be assessed by determining the amount of ATP incorporation. When the ATP labeled with a radioactive isotope is used, the amount of ATP incorporation can be assessed by determining radioactivity captured on the plate with a scintillation counter.

According to this method, the RET kinase-inhibiting activity of the compound can be assessed.

(5) Therapeutic Agent, Pharmaceutical Composition and Therapeutic Method

The therapeutic agent of the invention containing an RET kinase inhibiting substance is an agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract. Moreover, the therapeutic agent of the invention containing an RET kinase inhibiting substance is an agent for treating thyroid carcinoma. Preferably, the therapeutic agent of the invention is used for a disease including a cell expressing mutant RET.

The therapeutic agent of the invention may be administered to a living organism, i.e., a mammal (e.g., human, rat, rabbit, sheep, pig, bovine, cat, dog, monkey, etc.) that requires treatment of the disease.

The pharmaceutical composition of the invention contains an RET kinase inhibiting substance for administering to an organism including a cell expressing mutant RET.

The pharmaceutical composition of the invention can be used as a therapeutic agent for treating a disease expressing mutant RET. Examples of diseases expressing mutant RET include multiple endocrine neoplasia, type IIA, multiple endocrine neoplasia, type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

The pharmaceutical composition of the invention may be administered to a living organism, i.e., a mammal (e.g., human, rat, rabbit, sheep, pig, bovine, cat, dog, monkey, etc.). According to the present invention, said living organism includes a cell expressing mutant RET.

According to the present invention, the therapeutic agent contains an agent for improving prognosis of cancer, an agent for preventing cancer recurrence or the like. The therapeutic agent for treating cancer or tumor contains an antitumor agent, an agent for suppressing cancer metastasis or the like.

The effect of treatment may be verified by observation of an x-ray picture, CT or the like, by histopathological diagnosis of biopsy, or from a disease marker value.

Where a therapeutic agent or a pharmaceutical composition of the invention is used, the given dosage of the RET kinase inhibiting substance differs depending on the degree of the symptom, age, sex, weight and sensitivity difference of the patient, administration mode, administration period, administration interval, nature, prescription and the type of the pharmaceutical formulation, and the type of the active element. Usually, but without limitation, the dosage of the RET kinase inhibiting substance is 0.1-1000 mg/day, preferably 0.5-100 mg/day, more preferably 1-30 mg/day for an adult (weight 60 kg), which may be administered once to three times a day.

Although the therapeutic agent or the pharmaceutical composition containing the RET kinase inhibiting substance of the invention as an active element may be used alone, it is usually mixed with appropriate additives and made into a formulation.

Examples of such additive include excipients, binders, lubricants, disintegrants, colorants, flavoring agents, emulsifiers, surfactants, solubilizing agents, suspending agents, tonicity agents, buffers, antiseptic agents, antioxidant agents, stabilizers, absorption promoters and the like that are generally used for medicine. If required, they may be used in combination. Examples of such additive are as follows.

Excipients: lactose, sucrose, glucose, cornstarch, mannitol, sorbitol, starch, alpha-starch, dextrin, crystalline cellulose, light anhydrous silicic acid, aluminum silicate, calcium silicate, magnesium aluminometasilicate and calcium hydrogen phosphate.

Binders: for example, polyvinyl alcohol, methyl cellulose, ethyl cellulose, gum arabic, tragacanth, gelatin, shellac, hydroxypropyl methylcellulose, hydroxypropylcellulose, carboxymethylcellulose sodium, polyvinylpyrrolidone and macrogol.

Lubricants: magnesium stearate, calcium stearate, sodium stearyl fumarate, talc, polyethyleneglycol and colloid silica.

Disintegrants: crystalline cellulose, agar, gelatin, calcium carbonate, sodium hydrogen carbonate, calcium citrate, dextrin, pectin, low substituted hydroxypropylcellulose, carboxymethylcellulose, carboxymethylcellulose calcium, croscarmellose sodium, carboxymethyl starch and carboxymethyl starch sodium.

Colorants: ferric oxide, yellow ferric oxide, carmine, caramel, beta-carotene, titanium oxide, talc, riboflavin sodium phosphate, yellow aluminum lake and the like that are approved as additives in medicine.

Flavoring agents: cocoa powder, menthol, aromatic powder, peppermint oil, camphor and cinnamon powder.

Emulsifiers or surfactants: stearyl triethanolamine, sodium lauryl sulfate, laurylaminopropionate, lecithin, glycerine monostearate, sucrose fatty acid ester and glycerine fatty acid ester.

Solubilizing agents: polyethyleneglycol, propylene glycol, benzyl benzoate, ethanol, cholesterol, triethanolamine, sodium carbonate, sodium citrate, Polysorbate 80 and nicotine acid amide, Suspending agents: in addition to the surfactants mentioned above, hydrophilic polymers such as polyvinyl alcohol, polyvinylpyrrolidone, methylcellulose, hydroxymethylcellulose, hydroxyethylcellulose and hydroxypropylcellulose.

Tonicity agents: glucose, sodium chloride, mannitol and sorbitol.

Buffers: buffers made from phosphate, acetate, carbonate and citrate.

Antiseptic agents: methylparaben, propylparaben, chlorobutanol, benzyl alcohol, phenethyl alcohol, dehydroacetic acid and sorbic acid.

Antioxidant agents: hydrosulfate, ascorbic acid and alpha-tocopherol.

Stabilizers: those generally used for medicine.

Absorption promoters: those generally used for medicine.

If required, components such as vitamins and amino acids may be blended.

Examples of formulations include oral formulations such as tablets, dispersant, granule, fine granule, capsule, syrup, lozenge and inhaler; external formulations such as suppository, ointment, eye ointment, poultice strip, eye-drops, nasal drops, eardrops, skin patch and lotion; and injectable formulations.

The oral formulations mentioned above may be formulated by appropriately combining the additives mentioned above. If necessary, surface of these formulations may be coated.

The external formulations mentioned above may be formulated by appropriately combining the additives mentioned above, particularly excipients, binders, flavoring agents, emulsifiers, surfactants, solubilizing agents, suspending agent, tonicity agents, antiseptic agents, antioxidant agents, stabilizers and absorption promoters.

The injectable formulations mentioned above may be formulated by appropriately combining the additives mentioned above, particularly emulsifiers, surfactants, solubilizing agents, suspending agents, tonicity agents, buffers, antiseptic agents, antioxidant agents, stabilizers and absorption promoters. The injectable formulations may be used through means such as infusion, intramuscular injection, subcutaneous injection, intradermal injection and intravenous injection.

The present invention relates to a method for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract; the method including administering an effective amount of an RET kinase inhibiting substance to a patient. The present invention also relates to a method for treating thyroid carcinoma, including administering an effective amount of an RET kinase inhibiting substance to a patient.

The present invention further relates to a method for treating a disease, including administering an effective amount of an RET kinase inhibiting substance to an organism including a cell expressing mutant RET. According to the present invention, said disease is preferably at least one disease selected from multiple endocrine neoplasia, type IIA, multiple endocrine neoplasia, type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

According to the therapeutic method of the invention, the route and the method for administering the RET kinase inhibiting substance are not particularly limited and reference may be made to the description of the therapeutic agent or the pharmaceutical composition above.

The present invention includes use of an RET kinase inhibiting substance for producing a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract. The present invention also includes use of an RET kinase inhibiting substance for producing a therapeutic agent for treating thyroid carcinoma.

The present invention further includes use of an RET kinase inhibiting substance for producing a pharmaceutical composition containing the RET kinase inhibiting substance for administering to an organism including a cell expressing mutant RET. As to the use according to the invention, the pharmaceutical composition is effective as an agent for treating at least one disease selected from multiple endocrine neoplasia, type IIA, multiple endocrine neoplasia, type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

The present invention includes an RET kinase inhibiting substance for a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract. In addition, the present invention includes an RET kinase inhibiting substance for a therapeutic agent for treating thyroid carcinoma.

Furthermore, the present invention includes an RET kinase inhibiting substance for a pharmaceutical composition containing the RET kinase inhibiting substance for administering to an organism including a cell expressing mutant RET. According to the present invention, said pharmaceutical composition is useful as a therapeutic agent for treating at least one disease selected from multiple endocrine neoplasia, type IIA, multiple endocrine neoplasia, type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

The present invention also provides an RET kinase inhibitor containing the compound represented by General Formula (I), a pharmacologically acceptable salt thereof or a solvate thereof.

The compound represented by General Formula (I) is as mentioned above and preferably 4-(3-chloro-4-(cyclopropylaminocarbonyl)aminophenoxy)-7-methoxy-6-quinolinecarboxamide.

The present invention further provides an RET kinase inhibitor containing at least one compound selected from 5-(5-fluoro-2-oxo-1,2-dihydroindole-3-ylidenemethyl)-2,4-dimethyl-1H-pyrrole-3-carboxylic acid(2-diethylaminoethyl)amide (SU 11248), N-{2-chloro-4-[(6,7-dimethoxy-4-quinolyl)oxy]phenyl}-N'-(5-methyl-3-isoxazolyl)urea (KRN951) and 4-[(4-fluoro-2-methylindole-5-yl)oxy]-6-methoxy-7-[3-(pyrrolidine-1-yl)propoxy]quinazoline (AZD2171), a pharmacologically acceptable salt thereof or a solvate thereof.

The RET kinase-inhibiting activity of the RET kinase inhibitor of the invention can be determined as described above.

The compound may be used either alone or mixed with appropriate additives mentioned above and made into a formulation as the RET kinase inhibitor of the invention.

As to the usage and the dosage of the RET kinase inhibitor of the invention, reference may be made to the description of the therapeutic agent or the pharmaceutical composition above.

The present invention also includes use of at least one compound selected from the compound represented by General Formula (I), SU11248, KRN951 and AZD2171, a pharmacologically acceptable salt thereof or a solvate thereof, for producing an RET kinase inhibitor.

The present invention further includes a method for inhibiting RET kinase with at least one compound selected from the compound represented by General Formula (I), SU11248, KRN951 and AZD2171, a pharmacologically acceptable salt thereof or a solvate thereof. According to the method of the invention, the usage and the dosage of the compound are not particularly limited and reference may be made to the description of the therapeutic agent or the pharmaceutical composition above.

2. Method for Predicting Sensitivity

The present invention provides a method for predicting whether or not a patient is highly sensitive to an RET kinase inhibiting substance of the invention using the presence or the absence of RET mutation in the cell as an indication. Therapeutic effect of a RET kinase inhibiting substance is more prospective for patients highly sensitive to said RET kinase inhibiting substance.

According to the method of the invention, a patient is preferably a patient suffering from at least one disease selected from multiple endocrine neoplasia, type IIA, multiple endocrine neoplasia, type IIB, familial medullary thyroid carcinoma, thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract.

(1) Step of Determining the Presence or the Absence of RET Mutation in the Cell

In this step, the cell is preferably taken from the patient. The cell may be obtained, for example, by removing it from a patient by a surgical procedure (e.g., biopsy, etc.). Preferably, blood cells are used for genetic-variation-induced diseases such as multiple endocrine neoplasia, type IIA, multiple endocrine neoplasia, type IIB, familial medullary thyroid carcinoma, thyroid carcinoma, papillary thyroid carcinoma, Hirschsprung disease, pheochromocytoma, parathyroid hyperplasia and mucosal neuromas of the gastrointestinal tract.

The presence or the absence of RET mutation can be determined according to the method described above.

(2) Step of Predicting Whether or not Patient is Highly Sensitive to RET Kinase Inhibiting Substance In this step, whether a patient is highly sensitive to an RET kinase inhibiting substance can be predicted preferably using the presence or the absence of RET mutation in the cell determined in (1) as an indication. Specifically, when the cell determined is expressing mutant RET, the patient is judged to be highly sensitive to the RET kinase inhibiting substance.

Another aspect of the invention is a method for analyzing sensitivity of a cell to an RET kinase inhibiting substance using the determination result in (1) as an indication. Specifically, when the cell is expressing mutant RET based on the determination results in (1), this cell is judged to be more sensitive to the RET kinase inhibiting substance as compared to cells not expressing the mutant RET.

Yet another aspect of the invention is a method for selecting a cell or a patient highly sensitive to an RET kinase inhibiting substance using the determination result in (1) as an indication. Specifically, when a cell is expressing mutant RET as determined from the results in (1), this cell or a patient having this cell is judged to be highly sensitive to the RET kinase inhibiting substance. Thus, such cell or such patient can be selected as a cell or a patient highly sensitive to the RET kinase inhibiting substance.

Still yet another aspect of the invention is a method for classifying patients through analysis of sensitivity to an RET kinase inhibiting substance using the determination result in (1) as an indication. Specifically, according to the method of the invention, sensitivity of patients to an RET kinase inhibiting substance is analyzed based on the determination results in (1) as described above, and the patients having the cell of interest can be classified according to this result. For example, patients may be classified into a group including cells expressing mutant RET and a group without such cell. Alternatively, patients may be classified into a group highly sensitive to an RET kinase inhibiting substance and a group of others.

Still yet another aspect of the invention is a method for selecting a patient for administering an RET kinase inhibiting substance, the method including selecting a patient having a cell expressing mutant RET based on the results from the determination in (1). Patients having a cell expressing mutant RET can be a target intended for administering the RET kinase inhibiting substance.

Still yet another aspect of the invention is a method for predicting the therapeutic effect of the RET kinase inhibiting substance on a patient based on the results from the determination in (1). According to the method of the invention, when the cell is expressing mutant RET as determined from the results in (1), the cell is judged to be highly sensitive to the RET kinase inhibiting substance, and thus the therapeutic effect of this RET kinase inhibiting substance is predicted be high on the cell or a patient having this cell.

The present invention also relates to a method for determining the presence or the absence of RET mutation in the cell derived from a patient for predicting the sensitivity level of the patient to the RET kinase inhibiting substance. This determination method is as described in (1) above.

Determination of the presence or the absence of RET mutation enables prediction of the sensitivity level of a patient to the RET kinase inhibiting substance.

In this step, although the RET kinase inhibiting substance is as described above, it is preferably 4-(3-chloro-4-(cyclopropylaminocarbonyl)aminophenoxy)-7-methoxy-6-quinolinecarboxamide, a pharmacologically acceptable salt thereof or a solvate thereof.

The method of the invention can be employed to predict the level of the efficacy of the RET kinase inhibiting substance on a patient before administering the RET kinase inhibiting substance to the patient. Therefore, patients who are expected to be more susceptible to the RET kinase inhibiting substance can be selected for carrying out the treatment of the disease. Thus, the present invention is highly effective in clinical respect.

The present invention provides a test kit for determining the presence or the absence of RET mutation used for the method of the invention. The test kit of the invention contains the reagents mentioned above used for the determination. The test kit of the invention allows prediction of whether or not a patient is highly sensitive to the RET kinase inhibiting substance.

The present invention also relates to use of the test kit for the prediction mentioned above.

Hereinafter, the present invention will be illustrated by way of specific examples, although the invention should not be limited thereto.

EXAMPLE 1

Determination of RET Kinase-Inhibiting Activity of RET Kinase Inhibiting Substance RET kinase-inhibiting activity of test substances were tested by ProQinase (Freiburg, Germany, GmbH) upon our request. To be more precise, RET kinase-inhibiting activity was determined as follows.

1. Expression and Purification of RET

RET was expressed as human recombinant GST fusion protein (hereinafter, also referred to as "RET recombinant protein") in an insect cell (*Spodoptera frugiperda* 9 (Sf9)) according to the method of Baculovirus Expression System. The expressed RET recombinant protein was purified by affinity chromatography using GSH-agarose (Sigma) or Ni-NTH-agarose (Qiagen). The purity and identification of the protein can be confirmed by SDS-PAGE silver staining and western blotting using an antibody specific to RET.

2. Determination of Inhibitory Activity to RET Kinase Activity

First, to each well of streptavidin-coated 96-well Flash-Plate (Perkin Elmer/NEM), 20 µl of standard reaction solution, 5 µl of ATP solution (diluted with $H_2O$), 5 µl of the test substance (10% aqueous dimethylsulfoxide solution), and a mixed solution including 10 µl of solution containing 50 ng of RET recombinant protein and 10 µl of solution containing 125 ng of biotinylated Poly(Glu, Tyr)$_{4:1}$ were added sequentially. This kinase reaction solution (50 µL) contained 60 mM HEPES-NaOH (pH7.5), 3 mM $MgCl_2$, 3 mM $MnCl_2$, 3 µM Na-orthovanadate, 1.2 mM DTT, 50 µg/ml PEG$_{20000}$, and 1 µM [γ-$^{33}$P]-ATP.

4-(3-chloro-4-(cyclopropylaminocarbonyl)aminophenoxy)-7-methoxy-6-quinolinecarboxamide (methanesulfonate), 6-[2-(methylcarbamoyl)phenylsulfanyl]-3-E-[2-(pyridine-2-yl)ethenyl]indazole (hereinafter, also referred to as "AG013736"), SU11248, KRN951 or AZD2171 was used as the test substance.

4-(3-chloro-4-(cyclopropylaminocarbonyl)aminophenoxy)-7-methoxy-6-quinolinecarboxamide was produced according to the descriptions of International publication No. 02/32872 pamphlet (WO02/32872) and International publication No. 2005/063713 pamphlet (WO2005/063713).

AG013736 was produced based on the description of International publication No. 01/002369 pamphlet (WO01/002369). SU11248 was produced based on the description of International publication No. 01/060814 pamphlet (WO01/060814). KRN951 was produced based on the description of International publication No. 02/088110 pamphlet (WO02/088110). AZD2171 was produced based on the description of International publication No. 00/47212 pamphlet (WO00/47212).

Next, the reaction solution was incubated at 30° C. for 80 minutes, after which 50 µl of 2% (v/v) $H_3PO_4$ solution was added to terminate the reaction.

The 96-well plate was washed and aspirated twice with 200 µl of 0.9% (w/v) NaCl solution.

The amount of $^{33}P_i$ incorporation can be assessed by determining the radioactivity on the plate with a microplate scintillation counter (from Microbeta, Wallac).

The manipulation was performed with a BeckmanCoulter/Sagian robotic system.

The concentration of the test substance required for inhibiting RET kinase activity for 50% (IC$_{50}$) was calculated using specific radioactivity of $^{33}P$ at varying concentrations (10 points ranging from 10 µM to 0.0003 µM) with Prism 3.03 (Windows, Graphpad, San Diego, Calif., USA).

In this case, the value obtained for the case where substrate Poly(Glu, Tyr)$_{4:1}$ was solely added (without the addition of RET recombinant protein) was assumed 0% while the value obtained for the case where RET recombinant protein and substrate Poly(Glu, Tyr)$_{4:1}$ were added (without the addition of the test substance) was assumed 100%.

The kinase activity in the presence of the test substance at each concentration was assessed as percentage of the value obtained by subtracting the 0% value from the radioactivity value to the value obtained by subtracting the 0% value from the 100% value. Based on this percentage (%), the concentration of the test substance required to inhibit RET kinase activity for 50% (IC$_{50}$) was calculated.

As a result, 4-(3-chloro-4-(cyclopropylaminocarbonyl)aminophenoxy)-7-methoxy-6-quinolinecarboxamide was found to have RET kinase-inhibiting activity (IC$_{50}$=35 nM). In addition, SU11248, KRN951 and AZD2171 were also found to have RET kinase-inhibiting activity (IC$_{50}$=64, 92 and 75 nM, respectively). AG013736 had IC$_{50}$ of 5600 nM. Furthermore, the test substances differed in the level of RET kinase-inhibiting activity.

EXAMPLE 2

Effect of RET Kinase Inhibiting Substance on Ligand-Independent RET Phosphorylation in Human Medullary Thyroid Carcinoma Cell Line (TT)

1. Preparation of Cell Extract

Human medullary thyroid carcinoma cell line (TT, purchased from ATCC) was suspended in RPMI1640 medium containing 15% FBS (purchased from Sigma). TT is a cell expressing RET where cysteine at codon 634 in the wild-type RET amino acid sequence is mutated with tryptophan (Biochemical and Biophysical Research Communications, 207, 1022-1028, 1995). Two mL of this cell suspension per well ($4 \times 10^5$ cells/mL) was added to 6-well cell culture plate (purchased from FALCON), and cultured in a 5% $CO_2$ incubator (37° C.) overnight. After cultivation, supernatant was removed from each well and 1.8 mL of RPMI1640 medium containing 15% FBS was added. Then, 0.2 mL of test substance 4-(3-chloro-4-(cyclopropylaminocarbonyl)aminophenoxy)-7-methoxy-6-quinolinecarboxamide (methanesulfonate) (diluted in RPMI1640 medium containing 15% FBS) dissolved in dimethylsulfoxide was added and cultured in a 5% $CO_2$ incubator (37° C.) for an hour. Supernatant was removed from each well, which was then washed with 400 μL of PBS, and added with 100 μL of solubilizing buffer (50 mM Hepes (pH7.4), 150 mM NaCl, 10% (v/v) glycerol, 1% Triton X-100, 1.5 mM $MgCl_2$, 1 mM EDTA (pH 8.0), 100 mM NaF, 1 mM PMSF, 10 μg/mL, Aprotinin, 50 μg/mL Leupeptin, 1 μg/mL Pepstatin A and 1 mM $Na_3VO_4$). Cells in this solution were harvested with a scraper and treated at 15,000 rpm and 4° C. for 15 minutes. SDS buffer was added to the supernatant and subjected to treatment at 94° C. for 5 minutes to solubilize the protein, which was then prepared to 20 μg/10 μL as a cell extract.

2. Electrophoresis and Western Blotting

The cell extract (20 μg/10 μL) was subjected to electrophoresis on 4-20% gradient polyacrylamide gel (purchased from Daiichi Pure Chemicals), followed by transfer on a PVDF membrane (purchased from Amersham pharmacia biotech) by a conventional technique. Then, the transferred membrane was immunoblotted using anti-RET antibody (anti-RET, purchased from Cell Signaling), anti-phosphorylated RET antibody (anti-phospho RET (Tyr 905), purchased from Cell Signaling), anti-Erk1/2 antibody (anti-Erk1/2, purchased from Cell Signaling) or anti-phosphorylated Erk1/2 antibody (anti-phospho-Erk1/2, purchased from Cell Signaling) as primary antibody, and horse radish peroxidase-labeled anti-rabbit IgG antibody (anti-rabbit IgG; HRP-linked Antibody (purchased from Cell Signaling)) as secondary antibody. The membrane was washed and then treated with Super Signal (purchased from PIERCE) for color development.

RET autophosphorylation activity (%) of each lane was determined assuming the absorbance of the well added with test substance-free cell extract as 100% RET autophosphorylation activity. RET autophosphorylation activity (%) was determined while stepwise varying the concentration of the test substance to calculate the concentration of the test substance required for inhibiting RET autophosphorylation activity for 50% ($IC_{50}$).

As a result, 4-(3-chloro-4-(cyclopropylaminocarbonyl)aminophenoxy)-7-methoxy-6-quinolinecarboxamide inhibited RET phosphorylation in a concentration-dependent manner ($IC_{50}$=27 nM) (FIG. 1). In addition, 4-(3-chloro-4-(cyclopropylaminocarbonyl)aminophenoxy)-7-methoxy-6-quinolinecarboxamide was also found to inhibit phosphorylation of one of the downstream molecule of RET, Erk1/2, which is associated with cell growth signal, at a concentration similar to that for RET kinase (FIG. 1).

EXAMPLE 3

Effect of RET Kinase Inhibiting Substance on Cell Growth of Human Medullary Thyroid Carcinoma Cell Line (TT)

Human medullary thyroid carcinoma cell line (TT, purchased from ATCC) was suspended in RPMI1640 medium containing 15% FBS (purchased from Sigma). 0.1 mL per well of this cell suspension ($3 \times 10^4$ cells/mL) was added to 96-well cell culture plate (purchased from NUNC), and cultured in a 5% $CO_2$ incubator (37° C.) overnight. After cultivation, 0.1 mL of test substance 4-(3-chloro-4-(cyclopropylaminocarbonyl)aminophenoxy)-7-methoxy-6-quinolinecarboxamide (methanesulfonate) diluted in RPMI1640 medium containing 15% FBS was added to each well and further cultured in a 5% $CO_2$ incubator (37° C.) for 10 days. After cultivation, 10 μL of Cell Counting Kit-1 (purchased from DOJINDO) was added to each well, treated in 5% $CO_2$ incubator (37° C.) for color development and absorbance of each well was determined with plate reader MTP-500 (Corona Electric) at measurement wavelength of 415 nm and reference wavelength of 660 nm. Percentage (%) of the absorbance of each well with the test substance was determined compared to the absorbance of well without the test substance, based on which concentration of the test substance required for inhibiting cell growth for 50% ($IC_{50}$) was calculated.

As a result, 4-(3-chloro-4-(cyclopropylaminocarbonyl)aminophenoxy)-7-methoxy-6-quinolinecarboxamide was found to have inhibitory activity of $IC_{50}$=78 nM against growth of human medullary thyroid carcinoma cell line (TT).

EXAMPLE 4

Antitumor Effect of RET Kinase Inhibiting Substance in Model for Subcutaneous Transplantation of Human Medullary Thyroid Carcinoma Cell Line (TT)

Human medullary thyroid carcinoma cell line (TT, purchased from ATCC) was cultured at 37° C. in RPMI1640 (containing 15% FBS) in a 5% carbon dioxide incubator to about 80% confluence, and cells were harvested with trypsin-EDTA according to a general method. The cells were suspended in a phosphate buffer to prepare $1 \times 10^8$ cells/mL suspension. 0.1 mL each of the resulting cell suspension was subcutaneously transplanted to a nude mouse at the side of its body (purchased from Charles River).

Once the tumor volume became approximately 100-200 $mm^3$ after transplantation, the test substance 4-(3-chloro-4-(cyclopropylaminocarbonyl)aminophenoxy)-7-methoxy-6-quinolinecarboxamide (methanesulfonate) was orally administered for 10 mg/kg, 30 mg/kg or 100 mg/kg, once a day, for four weeks. The major and minor axes of tumors were measured with Digimatic caliper (Mitsutoyo), and tumor volumes were calculated according to the following formula.

Tumor Volume (TV)=Major axis of tumor (mm)×(Minor axis of tumor)$^2$ ($mm^2$)/2

Figure 2:
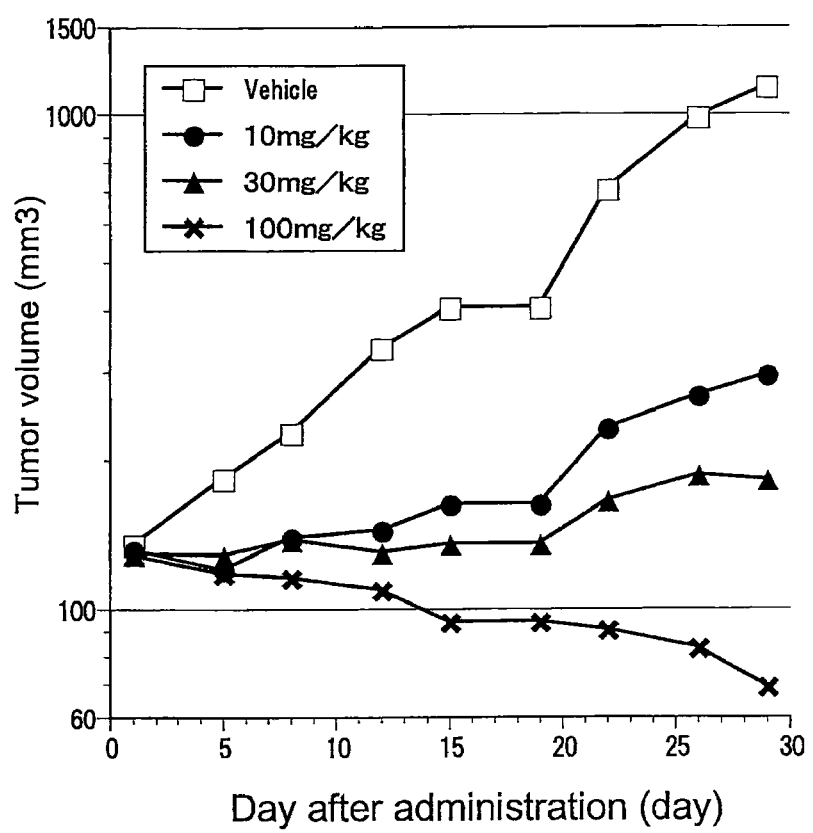
FIG. 2 shows an antitumor effect of 4-(3-chloro-4-(cyclopropylaminocarbonyl)aminophenoxy)-7-methoxy-6-quinolinecarboxamide in a model for subcutaneous transplantation of human medullary thyroid carcinoma cell line (TT).

As a result, 4-(3-chloro-4-(cyclopropylaminocarbonyl)aminophenoxy)-7-methoxy-6-quinolinecarboxamide was found to have dose-dependent antitumor effect in the model for subcutaneous transplantation of human medullary thyroid carcinoma cell line (TT) (FIG. 2).

EXAMPLE 5

Effect of RET Kinase Inhibiting Substance on RET Phosphorylation in Model for Subcutaneous Transplantation of Human Medullary Thyroid Carcinoma Cell Line (TT)

Human medullary thyroid carcinoma cell line (TT, purchased from ATCC) was cultured at 37° C. in RPMI1640 (containing 15% FBS) in a 5% carbon dioxide incubator to about 80% confluence, and cells were harvested with trypsin-EDTA according to a general method. The cells were suspended in a phosphate buffer to prepare $1 \times 10^8$ cells/mL suspension. 0.1 mL each of the resulting cell suspension was subcutaneously transplanted to a nude mouse at the side of its body (purchased from Charles River).

Once the tumor volume became approximately 100-200 mm$^3$ after transplantation, the test substance 4-(3-chloro-4-(cyclopropylaminocarbonyl)aminophenoxy)-7-methoxy-6-quinolinecarboxamide (methanesulfonate) was orally administered for 10 mg/kg, 30 mg/kg or 100 mg/kg. Tumors were resected 2, 8, 12 or 24 hours after administration, to which solubilizing buffer (50 mM Hepes (pH7.4), 150 mM NaCl, 10% (v/v) glycerol, 1% Triton X-100, 1.5 mM MgCl$_2$, 1 mM EDTA (pH 8.0), 100 mM NaF, 1 mM PMSF, 10 μg/mL Aprotinin, 50 μg/mL Leupeptin, 1 μg/mL Pepstatin A, 1 mM Na$_3$VO$_4$), 25 mM β-glycerophosphate, and phosphatase inhibitor cocktail II (SIGMA)) were added and homogenized. Treatment at 15,000 rpm and 4° C. for 15 minutes and addition of SDS buffer to the supernatant were followed by treatment at 94° C. for 5 minutes to solubilize protein to 20 μg/10 μL to prepare cell extract. The cell extract was subjected to electrophoresis and immunoblotting in the same manner as in Example 2.

Figure 3:
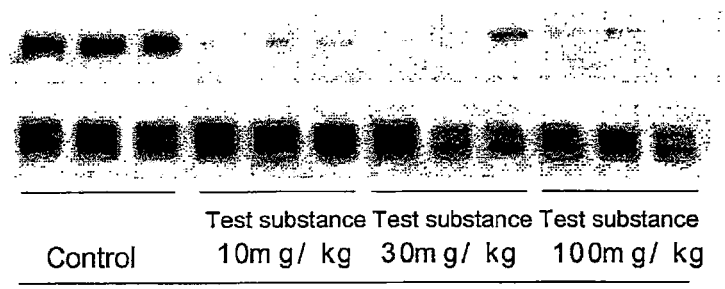
FIG. 3 shows an effect of 4-(3-chloro-4-(cyclopropylaminocarbonyl)aminophenoxy)-7-methoxy-6-quinolinecarboxamide on an RET kinase in a tumor tissue of a model for subcutaneous transplantation of human medullary thyroid carcinoma cell line (TT). (A) shows the effect on RET phosphorylation 2 hours after oral administration of the test substance at each dosage (10, 30 or 100 mg/kg) while (B) shows the effect on RET phosphorylation 2, 8, 12 or 24 hours after administration of the test substance at 100 mg/kg.
Figure 3:
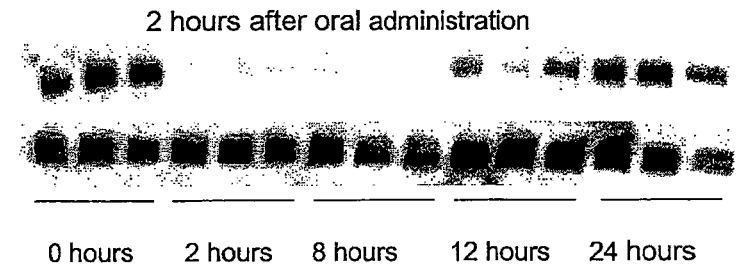

As a result, 4-(3-chloro-4-(cyclopropylaminocarbonyl) aminophenoxy)-7-methoxy-6-quinolinecarboxamide was found to have RET autophosphorylation inhibitory activity at the dose found to exert antitumor effect in the model for subcutaneous transplantation of human medullary thyroid carcinoma cell line (TT) (FIG. 3).

From these results, it was shown that the RET kinase inhibiting substance of the invention was expected to be more effective to organisms containing cells expressing mutant RET. The RET kinase inhibiting substance of the invention was also demonstrated to be useful as a therapeutic agent for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract as well as thyroid carcinoma.

Reference Example

Hereinafter, a method for producing a formulation of one of the RET kinase inhibiting substances, 4-(3-chloro-4-(cyclopropylaminocarbonyl)aminophenoxy)-7-methoxy-6-quinolinecarboxamide will be described as a reference example.
(Production of Pharmaceutical Composition)
(1) 1 mg Tablet
24 g of crystal (C) of methanesulfonate of 4-(3-chloro-4-(cyclopropylaminocarbonyl)aminophenoxy)-7-methoxy-6-quinolinecarboxamide (hereinafter, also referred to as "crystal (C)", which was produced according to the method described in Example 7 of WO2005/063713) and 192 g of light anhydrous silicic acid (antigelling agent sold under the trade name of AEROSIL (registered trademark) 200, Nippon Aerosil) were mixed with 20 L Super Mixer, and then 1236 g of D-mannitol (excipient, Towa-Kasei), 720 g of crystalline cellulose (excipient sold under the trade name of Avicel PH101, Asahi Kasei) and 72 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then size-regulated using Power Mill to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed and mixed together in a 20 L tumbler mixer, and molded with a tablet machine to obtain tablets with a total mass of 100 mg per tablet. Furthermore, the tablets were coated using aqueous 10% Opadry yellow (OPADRY 03F42069 YELLOW, Colorcon Japan) solution as a coating solution with a tablet coating machine, thereby obtaining coated tablets with a total mass of 105 mg per tablet.
(2) 10 mg Tablet
60 g of crystal (C) and 192 g of light anhydrous silicic acid (antigelling agent sold under the trade name of AEROSIL (registered trademark) 200, Nippon Aerosil) were mixed with 20 L Super Mixer, and then 1200 g of D-mannitol (excipient, Towa-Kasei), 720 g of crystalline cellulose (excipient sold under the trade name of Avicel PH101, Asahi Kasei) and 72 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then size-regulated using Power Mill to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed and mixed together in a 20 L tumbler mixer, and molded with a tablet machine to obtain tablets with a total mass of 400 mg per tablet. Furthermore, the tablets were coated using aqueous 10% Opadry yellow (OPADRY 03F42069 YELLOW, Colorcon Japan) solution as a coating solution with a tablet coating machine, thereby obtaining coated tablets with a total mass of 411 mg per tablet,
(3) 100 mg Tablet
31.4 g of crystal (C) and 4 g of light anhydrous silicic acid (antigelling agent sold under the trade name of AEROSIL (registered trademark) 200, Nippon Aerosil) were mixed with 1 L Super Mixer, and then 40.1 g of anhydrous calcium hydrogen phosphate (excipient, Kyowa Chemical Industry), 10 g of low substituted hydroxypropylcellulose (binder sold under the trade name of L-HPC (LH-21), Shin-Etsu Chemical) and 3 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then granulated using Power Mill to obtain granules. Together with the granules, 10 g of croscarmellose sodium (disintegrant sold under the trade name of Ac-Di-Sol, FMC International Inc.) and 1.5 g of sodium stearyl fumarate (lubricant, JRS Pharma LP) were mixed and molded with a tablet machine to obtain tablets with a total mass of 400 mg per tablet.

The present invention provides a therapeutic agent and a method containing an RET kinase inhibiting substance for treating at least one disease selected from multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, use of RET kinase inhibiting substance for producing said therapeutic agent and an RET kinase inhibiting substance for said therapeutic agent.

The present invention also provides a therapeutic agent and a method containing an RET kinase inhibiting substance for treating thyroid carcinoma, use of an RET kinase inhibiting substance for producing said therapeutic agent and an RET kinase inhibiting substance for said therapeutic agent.

Moreover, the present invention provides a pharmaceutical composition containing an RET kinase inhibiting substance for administering to an organism including a cell expressing mutant RET, a method for treating a disease including administration to an organism including a cell expressing mutant RET, use of RET kinase inhibiting substance for producing said pharmaceutical composition and an RET kinase inhibiting substance for said pharmaceutical composition.

The present invention also provides an RET kinase inhibitor.

Furthermore, the present invention provides a method for predicting the effect of an RET kinase inhibiting substance.

More specifically, the effect of an RET kinase inhibiting substance can be predicted using the presence or the absence of RET mutation in the cell as an indication.

Since the method according to the invention enables one to predict the effect of the compound without administering the compound to the patient, it has become possible to select a patient who is expected to be more susceptible to the compound. Thus, contribution to the patient's QOL has become possible.

Sequence Listing Free Text
SEQ ID NOS: 5-20 Primers

What is claimed is:

1. A method for treating at least one disease selected from the group consisting of multiple endocrine neoplasia, type IIA, multiple endocrine neoplasia, type IIB, familial medullary thyroid carcinoma, papillary thyroid carcinoma, sporadic medullary thyroid carcinoma, Hirschsprung disease, pheochromocytoma, parathyroid hyperplasia and mucosal neuromas of the gastrointestinal tract, the method comprising the step of administering an effective amount of an RET kinase inhibiting substance to a patient in need thereof, wherein said RET kinase inhibiting substance is 4-(3-chloro-4-(cyclopropylaminocarbonyl)aminophenoxy)-7-methoxy-6-quinolinecarboxamide or a pharmacologically acceptable salt thereof.

2. The method according to claim 1, wherein the RET kinase inhibiting substance is a mesylate salt of the compound 4-(3-chloro-4-(cyclopropylaminocarbonyl)aminophenoxy)-7-methoxy-6-quinolinecarboxamide.

3. A method for treating thyroid carcinoma, comprising administering an effective amount of an RET kinase inhibiting substance to a patient in need thereof, wherein said RET kinase inhibiting substance is 4-(3-chloro-4-(cyclopropylaminocarbonyl)aminophenoxy)-7-methoxy-6-quinolinecarboxamide or a pharmacologically acceptable salt thereof.

4. The method according to claim 3, wherein the RET kinase inhibiting substance is a mesylate salt of the compound 4-(3-chloro-4-(cyclopropylaminocarbonyl)aminophenoxy)-7-methoxy-6-quinolinecarboxamide.

5. A method for treating a disease, comprising the step of administering an effective amount of an RET kinase inhibiting substance to an organism comprising a cell expressing mutant RET, wherein said RET kinase inhibiting substance is 4-(3-chloro-4-(cyclopropylaminocarbonyl)aminophenoxy)-7-methoxy-6-quinolinecarboxamide or a pharmacologically acceptable salt thereof.

6. The method according to claim 5, wherein the RET kinase inhibiting substance is a mesylate salt of the compound 4-(3-chloro-4-(cyclopropylaminocarbonyl)aminophenoxy)-7-methoxy-6-quinolinecarboxamide.

* * * * *

SEQUENCE LISTING

```
<160> NUMBER OF SEQ ID NOS: 20

<210> SEQ ID NO 1
<211> LENGTH: 4757
<212> TYPE: DNA
<213> ORGANISM: Homo sapiens

<400> SEQUENCE: 1
ccgaagcagg gcgcgcagca gcgctgagtg ccccggaacg tgcgtcgcgc ccccagtgtc      60
cgtcgcgtcc gccgcgcccc gggcggggat ggggcggcca gactgagcgc cgcacccgcc     120
atccagaccc gccggcccta gccgcagtcc ctccagccgt ggccccagcg cgcacgggcg     180
atggcgaagg cgacgtccgg tgccgcgggg ctgcgtctgc tgttgctgct gctgctgccg     240
ctgctaggca aagtggcatt gggcctctac ttctcgaggg atgcttactg ggagaagctg     300
tatgtggacc aggcggccgg cacgcccttg ctgtacgtcc atgccctgcg ggacgcccct     360
gaggaggtgc ccagcttccg cctgggccag catctctacg gcacgtaccg cacacgcgtg     420
catgagaaca actggatctg catccaggag gacaccggcc tcctctacct taaccggagc     480
ctggaccata gctcctggga aagctcagt gtccgcaacc gcggctttcc cctgctcacc     540
gtctacctca aggtcttcct gtcacccaca tcccttcgtg agggcgagtg ccagtggcca     600
ggctgtgccc gcgtatactt ctccttcttc aacacctcct ttcagcctg cagctccctc     660 aagccccggg agctctgctt cccagagaca aggccctcct tccgcattcg ggagaaccga     720
cccccaggca ccttccacca gttccgcctg ctgcctgtgc agttcttgtg ccccaacatc     780
agcgtggcct acaggctcct ggagggtgag ggtctgccct tccgctgcgc cccggacagc     840
ctggaggtga gcacgcgctg ggccctggac cgcgagcagc gggagaagta cgagctggtg     900
gccgtgtgca ccgtgcacgc cggcgcgcgc gaggaggtgg tgatggtgcc cttcccggtg     960
accgtgtacg acgaggacga ctcggcgccc accttccccg cgggcgtcga caccgccagc    1020
gccgtggtgg agttcaagcg gaaggaggac accgtggtgg ccacgctgcg tgtcttcgat    1080
gcagacgtgg tacctgcatc aggggagctg gtgaggcggt acacaagcac gctgctcccc    1140
ggggacacct gggcccagca gaccttccgg gtggaacact ggcccaacga gacctcggtc    1200
caggccaacg gcagcttcgt gcgggcgacc gtacatgact ataggctggt tctcaaccgg    1260
```

-continued

```
aacctctcca tctcggagaa ccgcaccatg cagctggcgg tgctggtcaa tgactcagac    1320
ttccagggcc caggagcggg cgtcctcttg ctccacttca cgtgtcggt gctgccggtc     1380 agcctgcacc tgcccagtac ctactccctc tccgtgagca ggagggctcg ccgatttgcc    1440
cagatcggga aagtctgtgt ggaaaactgc caggcattca gtggcatcaa cgtccagtac   1500
aagctgcatt cctctggtgc caactgcagc acgctagggg tggtcacctc agccgaggac   1560
acctcgggga tcctgtttgt gaatgacacc aaggccctgc ggcggcccaa gtgtgccgaa    1620
cttcactaca tggtggtggc caccgaccag cagacctcta ggcaggccca ggcccagctg    1680
cttgtaacag tggaggggtc atatgtggcc gaggaggcgg gctgccccct gtcctgtgca    1740
gtcagcaaga gacggctgga gtgtgaggag tgtggcggcc tgggctcccc aacaggcagg    1800
tgtgagtgga ggcaaggaga tggcaaaggg atcaccagga acttctccac ctgctctccc    1860
agcaccaaga cctgccccga cggccactgc gatgttgtgg agacccaaga catcaacatt    1920
tgccctcagg actgcctccg gggcagcatt gttgggggac acgagcctgg ggagccccgg    1980
gggattaaag ctggctatgg cacctgcaac tgcttccctg aggaggagaa gtgcttctgc    2040
gagcccgaag acatccagga tccactgtgc gacgagctgt gccgcacggt gatcgcagcc    2100
gctgtcctct tctccttcat cgtctcggtg ctgctgtctg ccttctgcat ccactgctac    2160
cacaagtttg cccacaagcc acccatctcc tcagctgaga tgaccttccg gaggcccgcc    2220
caggccttcc cggtcagcta ctcctcttcc ggtgcccgcc ggccctcgct ggactccatg    2280
gagaaccagg tctccgtgga tgccttcaag atcctggagg atccaaagtg ggaattccct    2340
cggaagaact tggttcttgg aaaaactcta ggagaaggcg aatttggaaa agtggtcaag    2400
gcaacggcct ccatctgaa aggcagagca gggtacacca cggtggccgt gaagatgctg    2460
aaagagaacg cctccccgag tgagctgcga gacctgctgt cagagttcaa cgtcctgaag    2520
caggtcaacc acccacatgt catcaaattg tatgggcct gcagccagga tggcccgctc    2580
ctcctcatcg tggagtacgc caaatacggc tccctgcggg gcttcctccg cgagagccgc    2640
aaagtggggc ctggctacct gggcagtgga ggcagccgca actccagctc cctggaccac    2700
ccggatgagc gggccctcac catgggcgac ctcatctcat ttgcctggca gatctcacag    2760
gggatgcagt atctggccga gatgaagctc gttcatcggg acttggcagc cagaaacatc    2820
ctggtagctg aggggcggaa gatgaagatt tcggatttcg gcttgtcccg agatgtttat    2880
gaagaggatt cctacgtgaa gaggagccag ggtcggattc cagttaaatg gatggcaatt    2940
gaatcccttt tgatcatat ctacaccacg caaagtgatg tatggtcttt tggtgtcctg    3000
ctgtgggaga tcgtgaccct aggggaaac ccctatcctg ggattcctcc tgagcggctc    3060
ttcaaccttc tgaagaccgg ccaccggatg gagaggccag caactgcag cgaggagatg    3120 taccgcctga tgctgcaatg ctggaagcag agccggaca aaaggccggt gtttgcggac    3180
atcagcaaag acctggagaa gatgatggtt aagaggagag actacttgga ccttgcggcg    3240
tccactccat ctgactccct gatttatgac gacggcctct cagaggagga gacaccgctg    3300
gtggactgta ataatgcccc cctccctcga gccctcccct tccacatgga tgaaaacaaa    3360
ctctatggca tgtcagaccc gaactggcct ggagagagtc ctgtaccact cacgagagct    3420
gatggcacta acactgggtt ccaagatat ccaaatgata gtgtatatgc taactggatg    3480 ctttcacccct cagcggcaaa attaatggac acgtttgata gttaacattt ctttgtgaaa    3540
ggtaatggac tcaaggggg aagaaacatg ctgagaatgg aaagtctacc ggccttttct    3600
ttgtgaacgt cacattggcc gagccgtgtt cagttcccag gtggcagact cgttttttggt    3660
```

-continued

```
agtttgtttt aacttccaag gtggttttac ttctgatagc cggtgatttt ccctcctagc    3720
agacatgcca caccgggtaa gagctctgag tcttagtggt taagcattcc tttctcttca    3780
gtgcccagca gcacccagtg ttggtctgtg tccatcagtg accaccaaca ttctgtgttc    3840
acatgtgtgg gtccaacact tactacctgg tgtatgaaat tggacctgaa ctgttggatt    3900
tttctagttg ccgccaaaca aggcaaaaaa atttaaacat gaagcacaca cacaaaaaag    3960
gcagtaggaa aaatgctggc cctgatgacc tgtccttatt cagaatgaga gactgcgggg    4020
ggggcctggg ggtagtgtca atgcccctcc agggctggag gggaagaggg ccccgagga    4080 tgggcctggg ctcagcattc gagatcttga gaatgatttt tttttaatca tgcaaccttt    4140
ccttaggaag acatttggtt ttcatcatga ttaagatgat tcctagattt agcacaatgg    4200
agagattcca tgccatcttt actatgtgga tggtggtatc agggaagagg gctcacaaga    4260
cacatttgtc ccccgggccc accacatcat cctcacgtgt tcggtactga gcagccacta    4320
cccctgatga gaacagtatg aagaaagggg gctgttggag tcccagaatt gctgacagca    4380
gaggctttgc tgctgtgaat cccacctgcc accagcctgc agcacacccc acagccaagt    4440
agaggcgaaa gcagtggctc atcctacctg ttaggagcag gtaggcttg tactcacttt    4500 aatttgaatc ttatcaactt actcataaag ggacaggcta gctagctgtg ttagaagtag    4560
caatgacaat gaccaaggac tgctacacct ctgattacaa ttctgatgtg aaaaagatgg    4620
tgtttggctc ttatagagcc tgtgtgaaag gcccatggat cagctcttcc tgtgtttgta    4680
atttaatgct gctacaaggt gtttctgttt cttagattct gaccatgact cataagcttc    4740
ttgtcattct tcattgc                                                   4757
```

<210> SEQ ID NO 2
<211> LENGTH: 1114
<212> TYPE: PRT
<213> ORGANISM: Homo sapiens

<400> SEQUENCE: 2

Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

```
Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Val Val Met Val
                245                 250                 255

Pro Phe Pro Val Thr Val Tyr Asp Glu Asp Ser Ala Pro Thr Phe
                260                 265                 270

Pro Ala Gly Val Asp Thr Ala Ser Ala Val Glu Phe Lys Arg Lys
                275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
                340                 345                 350

Asp Tyr Arg Leu Val Leu Asn Arg Asn Leu Ser Ile Ser Glu Asn Arg
                355                 360                 365

Thr Met Gln Leu Ala Val Leu Val Asn Asp Ser Asp Phe Gln Gly Pro
                370                 375                 380

Gly Ala Gly Val Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
                420                 425                 430

Phe Ser Gly Ile Asn Val Gln Tyr Lys Leu His Ser Ser Gly Ala Asn
                435                 440                 445

Cys Ser Thr Leu Gly Val Val Thr Ser Ala Glu Asp Thr Ser Gly Ile
                450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
                500                 505                 510

Ala Gly Cys Pro Leu Ser Cys Ala Val Ser Lys Arg Arg Leu Glu Cys
                515                 520                 525

Glu Glu Cys Gly Gly Leu Gly Ser Pro Thr Gly Arg Cys Glu Trp Arg
                530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
                580                 585                 590
```

```
Gly His Glu Pro Gly Glu Pro Arg Gly Ile Lys Ala Gly Tyr Gly Thr
        595                 600                 605
Cys Asn Cys Phe Pro Glu Glu Lys Cys Phe Cys Glu Pro Glu Asp
        610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Ser Ala Phe Cys
                645                 650                 655
Ile His Cys Tyr His Lys Phe Ala His Lys Pro Pro Ile Ser Ser Ala
                660                 665                 670
Glu Met Thr Phe Arg Arg Pro Ala Gln Ala Phe Pro Val Ser Tyr Ser
            675                 680                 685
Ser Ser Gly Ala Arg Arg Pro Ser Leu Asp Ser Met Glu Asn Gln Val
        690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
                725                 730                 735
Lys Val Val Lys Ala Thr Ala Phe His Leu Lys Gly Arg Ala Gly Tyr
            740                 745                 750
Thr Thr Val Ala Val Lys Met Leu Lys Glu Asn Ala Ser Pro Ser Glu
        755                 760                 765
Leu Arg Asp Leu Leu Ser Glu Phe Asn Val Leu Lys Gln Val Asn His
    770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
                805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
        835                 840                 845
Gly Asp Leu Ile Ser Phe Ala Trp Gln Ile Ser Gln Gly Met Gln Tyr
    850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
                885                 890                 895
Arg Asp Val Tyr Glu Glu Asp Ser Tyr Val Lys Arg Ser Gln Gly Arg
            900                 905                 910
Ile Pro Val Lys Trp Met Ala Ile Glu Ser Leu Phe Asp His Ile Tyr
        915                 920                 925
Thr Thr Gln Ser Asp Val Trp Ser Phe Gly Val Leu Leu Trp Glu Ile
    930                 935                 940
Val Thr Leu Gly Gly Asn Pro Tyr Pro Gly Ile Pro Glu Arg Leu
945                 950                 955                 960
Phe Asn Leu Leu Lys Thr Gly His Arg Met Glu Arg Pro Asp Asn Cys
                965                 970                 975
Ser Glu Glu Met Tyr Arg Leu Met Leu Gln Cys Trp Lys Gln Glu Pro
            980                 985                 990
Asp Lys Arg Pro Val Phe Ala Asp  Ile Ser Lys Asp Leu  Glu Lys Met
        995                 1000                 1005
Met Val  Lys Arg Arg Asp Tyr  Leu Asp Leu Ala Ala  Ser Thr Pro
```

```
                      1010                 1015                 1020
Ser  Asp  Ser  Leu  Ile  Tyr  Asp  Asp  Gly  Leu  Ser  Glu  Glu  Thr
        1025                 1030                 1035

Pro  Leu  Val  Asp  Cys  Asn  Asn  Ala  Pro  Leu  Pro  Arg  Ala  Leu  Pro
    1040                 1045                 1050

Ser  Thr  Trp  Ile  Glu  Asn  Lys  Leu  Tyr  Gly  Met  Ser  Asp  Pro  Asn
    1055                 1060                 1065

Trp  Pro  Gly  Glu  Ser  Pro  Val  Pro  Leu  Thr  Arg  Ala  Asp  Gly  Thr
    1070                 1075                 1080

Asn  Thr  Gly  Phe  Pro  Arg  Tyr  Pro  Asn  Asp  Ser  Val  Tyr  Ala  Asn
    1085                 1090                 1095

Trp  Met  Leu  Ser  Pro  Ser  Ala  Ala  Lys  Leu  Met  Asp  Thr  Phe  Asp
    1100                 1105                 1110

Ser

<210> SEQ ID NO 3
<211> LENGTH: 4161
<212> TYPE: DNA
<213> ORGANISM: Homo sapiens

<400> SEQUENCE: 3
ccgaagcagg gcgcgcagca gcgctgagtg ccccggaacg tgcgtcgcgc ccccagtgtc      60
cgtcgcgtcc gccgcgcccc gggcggggat ggggcggcca gactgagcgc cgcacccgcc     120
atccagaccc gccggcccta gccgcagtcc ctccagccgt ggcccagcg cgcacgggcg      180 atggcgaagg cgacgtccgg tgccgcgggg ctgcgtctgc tgttgctgct gctgctgccg     240
ctgctaggca aagtggcatt gggcctctac ttctcgaggg atgcttactg ggagaagctg     300
tatgtggacc aggcggccgg cacgcccttg ctgtacgtcc atgccctgcg ggacgcccct     360
gaggaggtgc ccagcttccg cctgggccag catctctacg gcacgtaccg cacacggctg     420
catgagaaca actggatctg catccaggag gacaccggcc tcctctacct taaccggagc     480
ctggaccata gctcctggga agctcagt gtccgcaacc gcggctttcc cctgctcacc       540
gtctacctca aggtcttcct gtcacccaca tcccttcgtg agggcgagtg ccagtggcca     600
ggctgtgccc gcgtatactt ctccttcttc aacacctcct ttccagcctg cagctccctc     660
aagccccggg agtctgcttc ccagagaca aggccctcct tccgcattcg ggagaaccga      720 ccccaggca ccttccacca gttccgcctg ctgcctgtgc agttcttgtg ccccaacatc      780
agcgtggcct acaggctcct ggagggtgag gtctgccct tccgctgcgc cccggacagc      840
ctggaggtga gcacgcgctg ggccctggac cgcgagcagc gggagaagta cgagctggtg     900
gccgtgtgca cctgtcacgc cggcgcgcgc gaggaggtgg tgatggtgcc cttcccggtg     960
accgtgtacg acgaggacga ctcggcgccc accttccccg cgggcgtcga caccgccagc    1020
gccgtggtgg agttcaagcg gaaggaggac accgtggtgg ccacgctgcg tgtcttcgat    1080
gcagacgtgg tacctgcatc aggggagctg gtgaggcggt acacaagcac gctgctcccc    1140
ggggacacct gggcccagca gaccttccgg gtggaacact ggcccaacga gacctcggtc    1200
caggccaacg gcagcttcgt gcgggcgacc gtacatgact ataggctggt tctcaaccgg    1260
aacctctcca tctcggagaa ccgcaccatg cagctggcgg tgctggtcaa tgactcagac    1320
ttccagggcc caggagcggg cgtcctcttg ctccacttca cgtgtcggt gctgccggtc     1380 agcctgcacc tgcccagtac ctactcccctc tccgtgagca gggggctcg ccgatttgcc    1440 cagatcggga aagtctgtgt ggaaaactgc caggcattca gtggcatcaa cgtccagtac    1500
```

-continued

```
aagctgcatt cctctggtgc caactgcagc acgctagggg tggtcacctc agccgaggac   1560
acctcgggga tcctgtttgt gaatgacacc aaggccctgc ggcggcccaa gtgtgccgaa   1620
cttcactaca tggtggtggc caccgaccag cagacctcta ggcaggccca ggcccagctg   1680
cttgtaacag tggaggggtc atatgtggcc gaggaggcgg gctgcccccT gtcctgtgca   1740
gtcagcaaga gacggctgga gtgtgaggag tgtggcggcc tgggctcccc aacaggcagg   1800
tgtgagtgga ggcaaggaga tggcaaaggg atcaccagga acttctccac ctgctctccc   1860
agcaccaaga cctgccccga cggccactgc gatgttgtgg agacccaaga catcaacatt   1920
tgccctcagg actgcctccg gggcagcatt gttgggggac acgagcctgg ggagccccgg   1980
gggattaaag ctggctatgg cacctgcaac tgcttccctg aggaggagaa gtgcttctgc   2040
gagcccgaag acatccagga tccactgtgc gacgagctgt gccgcacggt gatcgcagcc   2100
gctgtcctct tctccttcat cgtctcggtg ctgctgtctg ccttctgcat ccactgctac   2160
cacaagtttg cccacaagcc acccatctcc tcagctgaga tgaccttccg gaggcccgcc   2220
caggccttcc cggtcagcta ctcctcttcc ggtgcccgcc ggccctcgct ggactccatg   2280
gagaaccagg tctccgtgga tgccttcaag atcctggagg atccaaagtg gaattccct   2340
cggaagaact tggttcttgg aaaaactcta ggagaaggcg aatttggaaa agtggtcaag   2400
gcaacggcct ccatctgaa aggcagagca gggtacacca cggtggccgt gaagatgctg   2460
aaagagaacg cctccccgag tgagctgcga gacctgctgt cagagttcaa cgtcctgaag   2520
caggtcaacc acccacatgt catcaaattg tatgggcct gcagccagga tggcccgctc   2580
ctcctcatcg tggagtacgc caaatacggc tccctgcggg gcttcctccg cgagagccgc   2640
aaagtggggc ctggctacct gggcagtgga ggcagccgca actccagctc cctggaccac   2700
ccggatgagc gggccctcac catgggcgac ctcatctcat ttgcctggca gatctcacag   2760
gggatgcagt atctggccga gatgaagctc gttcatcggg acttggcagc cagaaacatc   2820
ctggtagctg aggggcggaa gatgaagatt tcggatttcg gcttgtcccg agatgtttat   2880
gaagaggatt cctacgtgaa gaggagccag ggtcggattc cagttaaatg gatggcaatt   2940
gaatcccttt ttgatcatat ctacaccacg caaagtgatg tatggtcttt tggtgtcctg   3000
ctgtgggaga tcgtgaccct agggggaaac ccctatcctg ggattcctcc tgagcggctc   3060
ttcaaccttc tgaagaccgg ccaccggatg gagaggccag acaactgcag cgaggagatg   3120
taccgcctga tgctgcaatg ctggaagcag gagccggaca aaaggccggt gtttgcggac   3180
atcagcaaag acctggagaa gatgatggtt aagaggagag actacttgga ccttgcggcg   3240
tccactccat ctgactccct gatttatgac gacggcctct cagaggagga gacaccgctg   3300
gtggactgta taatgccccc cctccctcga gccctcccTt ccacatggat tgaaaacaaa   3360
ctctatggta gaatttccca tgcatttact agattctagc accgctgtcc cctctgcact   3420
atccttcctc tctgtgatgc ttttTaaaaa tgtttctggt ctgaacaaaa ccaaagtctg   3480
ctctgaacct tttTatttgt aaatgtctga ctttgcatcc agtttacatt taggcattat   3540
tgcaactatg ttttTctaaa aggaagtgaa aataagtgta attaccacat tgcccagcaa   3600
cttaggatgg tagaggaaaa aacagatcag ggcggaactc tcaggggaga ccaagaacag   3660
gttgaataag gcgcttctgg ggtgggaatc aagtcatagt acttctactt taactaagtg   3720
gataaatata caaatctggg gaggtattca gttgagaaag gagccaccag caccactcag   3780
cctgcactgg gagcacagcc aggttccccc agacccctcc tgggcaggca ggtgcctctc   3840
```

```
agaggccacc cggcactggc gagcagccac tggccaagcc tcagccccag tcccagccac    3900
atgtcctcca tcaggggtag cgaggttgca ggagctggct ggccctggga ggacgcaccc    3960
ccactgctgt tttcacatcc tttcccttac ccaccttcag gacggttgtc acttatgaag    4020
tcagtgctaa agctggagca gttgcttttt gaaagaacat ggtctgtggt gctgtggtct    4080
tacaatggac agtaaatatg gttcttgcca aaactccttc ttttgtcttt gattaaatac    4140
tagaaattta aaaaaaaaaa a                                              4161

<210> SEQ ID NO 4
<211> LENGTH: 1072
<212> TYPE: PRT
<213> ORGANISM: Homo sapiens

<400> SEQUENCE: 4

Met Ala Lys Ala Thr Ser Gly Ala Ala Gly Leu Arg Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
                35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
                115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
                180                 185                 190

Val Gln Phe Leu Cys Pro Asn Ile Ser Val Ala Tyr Arg Leu Leu Glu
                195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
                260                 265                 270

Pro Ala Gly Val Asp Thr Ala Ser Ala Val Val Glu Phe Lys Arg Lys
                275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320
```

```
Gly Asp Thr Trp Ala Gln Gln Thr Phe Arg Val Glu His Trp Pro Asn
            325                 330                 335

Glu Thr Ser Val Gln Ala Asn Gly Ser Phe Val Arg Ala Thr Val His
        340                 345                 350

Asp Tyr Arg Leu Val Leu Asn Arg Asn Leu Ser Ile Ser Glu Asn Arg
    355                 360                 365

Thr Met Gln Leu Ala Val Leu Val Asn Asp Ser Asp Phe Gln Gly Pro
370                 375                 380

Gly Ala Gly Val Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735
```

```
Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
                820                 825                 830

Arg Asn Ser Ser Ser Leu Asp His Pro Asp Glu Arg Ala Leu Thr Met
            835                 840                 845

Gly Asp Leu Ile Ser Phe Ala Trp Gln Ile Ser Gln Gly Met Gln Tyr
850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
                915                 920                 925

Thr Thr Gln Ser Asp Val Trp Ser Phe Gly Val Leu Leu Trp Glu Ile
930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu Glu Lys Met
            995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Arg Ile  Ser His Ala
    1055                1060                1065

Phe Thr  Arg Phe
    1070

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
attgtcatct cgccgttc                                                   18
```

```
<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
tgcttcagga cgttgaac                                                       18

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
tatcgcagga gagactgtga t                                                   21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tggagaagag aggctgtatc                                                     20

<210> SEQ ID NO 9
<211> LENGTH: 17
<212> TYPE: DNA
<213> ORGANISM: Artificial
<220> FEATURE:
<223> OTHER INFORMATION: primer

<400> SEQUENCE: 9
cgttgccttg actttc                                                         17

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tgccccttca gtgttcctac t                                                   21

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
cttgataaca ctggcaggtt                                                     20

<210> SEQ ID NO 12
<211> LENGTH: 20
<212> TYPE: DNA
<213> ORGANISM: Artificial
<220> FEATURE:
<223> OTHER INFORMATION: primer
```

<400> SEQUENCE: 12
gaggcgttct ctttcagcat                                           20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
tggaagaact tcggcatgag                                           20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
gaattcacag ccaccaagtg                                           20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ctacttagct ttccaagtgg                                           20

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
gggacagaca cctttggaaa ta                                        22

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
gttgaaggag tccttgactg                                           20

<210> SEQ ID NO 18
<211> LENGTH: 18
<212> TYPE: DNA
<213> ORGANISM: Artificial
<220> FEATURE:
<223> OTHER INFORMATION: primer

<400> SEQUENCE: 18
ctttcagcat cttcacgg                                             18

<210> SEQ ID NO 19
<211> LENGTH: 19

```
<212> TYPE: DNA
<213> ORGANISM: Artificial
<220> FEATURE:
<223> OTHER INFORMATION: primer

<400> SEQUENCE: 19
agtgaagttt ctaccatcc                                               19

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ggcgttctct ttcagcatct                                              20
```